US011723935B2

(12) United States Patent
Miller et al.

(10) Patent No.: US 11,723,935 B2
(45) Date of Patent: Aug. 15, 2023

(54) METHODS AND COMPOSITIONS FOR TREATING AND DIAGNOSING PANCREATIC CANCERS

(71) Applicant: New York University, New York, NY (US)

(72) Inventors: George Miller, Englewood, NJ (US); Deepak Saxena, New York, NY (US); Smruti Pushalkar, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 116 days.

(21) Appl. No.: 16/484,080

(22) PCT Filed: Feb. 6, 2018

(86) PCT No.: PCT/US2018/017052
§ 371 (c)(1),
(2) Date: Aug. 6, 2019

(87) PCT Pub. No.: WO2018/145082
PCT Pub. Date: Aug. 9, 2018

(65) Prior Publication Data
US 2020/0113951 A1    Apr. 16, 2020

Related U.S. Application Data

(60) Provisional application No. 62/455,424, filed on Feb. 6, 2017.

(51) Int. Cl.
*A61K 35/742*    (2015.01)
*A61K 9/00*    (2006.01)
*A61K 35/745*    (2015.01)
*A61K 35/747*    (2015.01)
*A61P 35/00*    (2006.01)

(52) U.S. Cl.
CPC .......... *A61K 35/742* (2013.01); *A61K 9/0019* (2013.01); *A61K 35/745* (2013.01); *A61K 35/747* (2013.01); *A61P 35/00* (2018.01)

(58) Field of Classification Search
CPC .. A61K 35/742; A61K 35/745; A61K 35/747; A61K 9/0019; A61P 35/00
See application file for complete search history.

(56) References Cited

U.S. PATENT DOCUMENTS

| 10,632,160 | B2* | 4/2020 | Chen | A61K 35/747 |
| 10,869,923 | B2* | 12/2020 | Lu | A61K 9/0053 |
| 11,096,971 | B2* | 8/2021 | Possemiers | A61K 35/744 |
| 11,213,552 | B2* | 1/2022 | Kovarik | A61K 38/1709 |
| 2014/0378531 | A1* | 12/2014 | Miller | A61K 31/7088 514/44 A |
| 2016/0120915 | A1* | 5/2016 | Blaser | A61K 31/7004 424/93.4 |
| 2016/0354416 | A1* | 12/2016 | Gajewski | A61P 31/04 |
| 2019/0290707 | A1* | 9/2019 | Chen | C12N 1/205 |
| 2020/0113951 | A1* | 4/2020 | Miller | A61K 35/742 |
| 2021/0069327 | A1* | 3/2021 | Lu | A61K 45/06 |
| 2021/0213073 | A1* | 7/2021 | Zeng | A61P 35/00 |
| 2021/0260092 | A1* | 8/2021 | Miller | A61P 31/10 |
| 2021/0315947 | A1* | 10/2021 | Lynch | A61K 9/0053 |
| 2021/0346438 | A1* | 11/2021 | Zitvogel | C12Q 1/689 |
| 2021/0353694 | A1* | 11/2021 | Possemiers | A61P 1/14 |
| 2022/0016188 | A1* | 1/2022 | Wargo | A61K 35/74 |

FOREIGN PATENT DOCUMENTS

| WO | 2015075688 A1 | 5/2015 | |
| WO | WO-2016172657 A2 * | 10/2016 | .............. A23L 33/10 |
| WO | WO-2018145082 A1 * | 8/2018 | ........... A61K 31/337 |
| WO | WO-2020243705 A1 * | 12/2020 | |
| WO | WO-2020243731 A2 * | 12/2020 | ........... A61B 17/244 |

OTHER PUBLICATIONS

Akshintala et al, Clinical Gastroenterology and HEpatology, Jan. 2019. 17/2:290-295. abstract only (Year: 2019).*
Chen et al, Scientific Reports. 2020, 10:20319, 11 pages, published online: Nov. 23, 2020 (Year: 2020).*
Gopalakrishnan et al, Immuno-Oncology Technology. 2020,Volime 6/Issue C:9-17. available online: May 20, 2020 (Year: 2020).*
Highlander et al, Cancer Research, (Dec. 2019) vol. 79, No. 24, Supp. Supplement. Abstract No. B24. abstract only (Year: 2019).*
THomas et al Nature Reviews/Gastroenterology & Hepatology, Jan. 2020, 17:53-64.published online:Dec. 6, 2019 (Year: 2020).*
Zhou et al, J. Translational Medicine, 2021, 19:215. 12 pages, published online: May 18, 2021 (Year: 2021).*
Shah et al. Trends in Food Science & Technology. 102 (2020) 178-192. available online Jun. 23, 2020 (Year: 2020).*
Routy et al. European Urology 74 (2018) 521-526 (Year: 2018).*
Routy et al, Nature Reviews, Clinical Oncology. Jun. 2018, 15:385-396. published online: Apr. 10, 2018 (Year: 2018).*
Messaoudene et al. Cancer Research (Aug. 2020) vol. 80, No. 16 Suppl. Abstract No. 5730 (Year: 2020).*
Janda et al. "16S rRNA Gene Sequencing for Bacterial Identification in the Diagnostic Laboratory: Pluses, Perils, and Pitfalls", Sep. 2007, Journal of Clinical Microbiology, vol. 45 No. 9, p. 2761-2764. (Year: 2007).*
Jiang et al. "Targeting focal adhesion kinase renders pancreatic cancers responsive to checkpoint immunotherapy", Aug. 2016, Nature Medicine, vol. 22 No. 8, p. 851-860. (Year: 2016).*

(Continued)

*Primary Examiner* — Gary B Nickol
*Assistant Examiner* — Amelia Nicole Dickens
(74) *Attorney, Agent, or Firm* — Troutman Pepper Hamilton Sanders LLP

(57) ABSTRACT

The application relates to methods based on modulating mammalian intestinal and/or pancreatic microbiota and related probiotic, prebiotic, and anti-bacterial compositions. Specifically, the application relates to the use of microbiome for prevention, treatment and diagnosis of pancreatic cancers or tumors, such as pancreatic ductal adenocarcinoma.

14 Claims, 35 Drawing Sheets
(35 of 35 Drawing Sheet(s) Filed in Color)
Specification includes a Sequence Listing.

(56) References Cited

OTHER PUBLICATIONS

Dingemanse et al. "Akkermansia muciniphila and Helicobacter typhlonius modulate intestinal tumor development in mice", 2015, Carcinogenesis, vol. 36, No. 11, p. 1388-1396 (Year: 2015).*
Communication (International Search Report) issued by the International Searching Authority in International Application No. PCT/US2018/017052, dated May 8, 2018, 4 pages total.
Communication (Written Opinion) issued by the International Searching Authority in International Application No. PCT/US2018/017052, dated May 8, 2018, 12 pages total.
Hamada, S. et al., "Differences in Gut Microbiota Profiles between Autoimmune Pancreatitis and Chronic Pancreatitis" The Tohoku Journal of Experimental Medicine (2018) vol. 244, Issue 2, pp. 113-117.
Leal-Lopes, C. et al., "Roles of Commensal Microbiota in Pancreas Homeostasis and Pancreatic Pathologies" Journal of Diabetes Research (2015) vol. 2015, No. 284680, 20 pages total.
Pushalkar, S. et al., "The Pancreatic Cancer Microbiome Promotes Oncogenesis by Induction of Innate and Adaptive Immune Suppression" Cancer Discovery (2018) vol. 8, No. 4, pp. 403-416.
Afshar-Kharghan, V. The role of the complement system in cancer. J. Clin. Invest. 127, 780-789 (2017).
Brown, J.H., Whitham, T.G., Morgan Ernest, S.K. & Gehring, C.A. Complex Species Interactions and the Dynamics of Ecological Systems: Long-Term Experiments. Science 293, 643-650 (2001).
Caporaso, J. G. et al. QIIME allows analysis of high-throughput community sequencing data. Nat. Methods 7, 335-336 (2010).
Caporaso, J.G., et al. Ultra-high-throughput microbial community analysis on the Illumina HiSeq and MiSeq platforms. The ISME Journal 6, 1621-1624 (2012).
Cho, M. S. et al. Autocrine effects of tumor-derived complement. Cell Reports 6, 1085-1095 (2014).
Edgar, R.C. Search and clustering orders of magnitude faster than BLAST. Bioinformatics 26, 2460-2461 (2010).
Farrell, J.J., et al. Variations of oral microbiota are associated with pancreatic diseases including pancreatic cancer. Gut 61, 582-588 (2012).
Haas, B.J., et al. Chimeric 16S rRNA sequence formation and detection in Sanger and 454-pyrosequenced PCR amplicons. Genome Research 21, 494-504 (2011).
Herlemann, D.P.R., et al. Transitions in bacterial communities along the 2000km salinity gradient of the Baltic Sea. ISME J 5, 1571-1579 (2011).
Hingorani, S. R. et al. Preinvasive and invasive ductal pancreatic cancer and its early detection in the mouse. Cancer Cell 4, 437-450 (2003).
Hingorani, S. R. et al. Trp53R172H and KrasG12D cooperate to promote chromosomal instability and widely metastatic pancreatic ductal adenocarcinoma in mice. Cancer Cell 7, 469-483 (2005).
Hruban, R. H. et al. Pancreatic intraepithelial neoplasia: a new nomenclature and classification system for pancreatic duct lesions. Am. J. Surg. Pathol. 25, 579-586 (2001).
Ino, Y., et al. Immune cell infiltration as an indicator of the immune microenvironment of pancreatic cancer. British journal of cancer 108, 914-923 (2013).
Ishikawa, T. et al. Identification of distinct ligands for the C-type lectin receptors mincle and dectin-2 in the pathogenic fungus Malassezia. Cell Host Microbe 13, 477-488 (2013).
Kamada, N., Seo, S.-U., Chen, G.Y. & Nunez, G. Role of the gut microbiota in immunity and inflammatory disease. Nat Rev Immunol 13, 321-335 (2013).
Klindworth, A., et al. Evaluation of general 16S ribosomal RNA gene PCR primers for classical and next-generation sequencing-based diversity studies. Nucleic Acids Research 41, e1-e1 (2013).
Masella, A.P., Bartram, A.K., Truszkowski, J.M., Brown, D.G. & Neufeld, J.D. PANDAseq: paired-end assembler for illumina sequences. BMC Bioinformatics 13, 31-31 (2012).
Mi, H., Muruganujan, A., Casagrande, J.T. & Thomas, P.D. Large-scale gene function analysis with the PANTHER classification system. Nature protocols 8, 1551-1566 (2013).
Michaud, D.S., Joshipura, K., Giovannucci, E. & Fuchs, C.S. A Prospective Study of Periodontal Disease and Pancreatic Cancer in US Male Health Professionals. Journal of the National Cancer Institute 99, 171-175 (2007).
Mitsuhashi, K., et al. Association of *Fusobacterium* species in pancreatic cancer tissues with molecular features and prognosis. Oncotarget; vol. 6, No. 9 (2015).
Navas-Molina, J.A., et al. Advancing our understanding of the human microbiome using QIIME. Methods in Enzymology 531, 371-444 (2013).
Plottel, C.S. & Blaser, M.J. Microbiome and Malignancy. Cell host & microbe 10, 324-335 (2011).
Price, M.N., Dehal, P.S. & Arkin, A.P. FastTree: Computing Large Minimum Evolution Trees with Profiles instead of a Distance Matrix. Molecular Biology and Evolution 26, 1641-1650 (2009).
Pushalkar, S., et al. Comparison of oral microbiota in tumor and non-tumor tissues of patients with oral squamous cell carcinoma. BMC Microbiology 12, 144-144 (2012).
Pushalkar, S., et al. Oral microbiota and host innate immune response in bisphosphonate-related osteonecrosis of the jaw. In J Oral Sci 6, 219-226 (2014).
Reikvam, D. H. et al. Depletion of murine intestinal microbiota: effects on gut mucosa and epithelial gene expression. PLoS One 6, e17996 (2011).
Rutkowski, M.R., et al. Microbially driven TLR5-dependent signaling governs distal malignant progression through tumor-promoting inflammation. Cancer cell 27, 27-40 (2015).
Sam, Q. H., Chang, M. W. & Chai, L. Y. The fungal mycobiome and its interaction with gut bacteria in the host. Int. J. Mol. Sci. 18, 330 (2017).
Schwabe, R.F. & Jobin, C. The microbiome and cancer. Nature reviews. Cancer 13, 800-812 (2013).
Segata, N., et al. Metagenomic biomarker discovery and explanation. Genome Biology 12, R60-R60 (2011).
Seifert, L. et al. The necrosome promotes pancreatic oncogenesis via CXCL1 and Mincle-induced immune suppression. Nature 532, 245-249 (2016).
Seifert, L., et al. Radiation Therapy Induces Macrophages to Suppress Immune Responses Against Pancreatic Tumors in Mice. Gastroenterology (2016).
Skalski, J. H. et al. Expansion of commensal fungus Wallemia mellicola in the gastrointestinal mycobiota enhances the severity of allergic airway disease in mice. PLoS Pathog. 14, e1007260 (2018).
Van Asbeck, E. C., Hoepelman, A. I., Scharringa, J., Herpers, B. L. & Verhoef, J. Mannose binding lectin plays a crucial role in innate immunity against yeast by enhanced complement activation and enhanced uptake of polymorphonuclear cells. BMC Microbiol. 8, 229 (2008).
Walters, W. et al. Improved bacterial 16S rRNA gene (V4 and V4-5) and fungal internal transcribed spacer marker gene primers for microbial community surveys. mSystems 1, e00009-15 (2015).
Zambirinis, C.P., et al. TLR9 ligation in pancreatic stellate cells promotes tumorigenesis. The Journal of Experimental Medicine 212, 2077-2094 (2015).
Communication (International Preliminary Report of Patentability) issued by the International Searching Authority in International Application No. PCT/US2018/017052, dated Aug. 6, 2019, 13 pages total.
Pushalkar, S., et al. The Pancreatic Cancer Microbiome Promotes Oncogenesis by Induction of Innate and Adaptive Immune Suppression, Cancer Discov. (2018) vol. 8, No. 4, pp. 403-416.

* cited by examiner

METHODS AND COMPOSITIONS FOR TREATING AND DIAGNOSING PANCREATIC CANCERS

CROSS-REFERENCE TO RELATED APPLICATIONS

This application is a U.S. National Phase application under 35 U.S.C. § 371 of International Patent Application No. PCT/US2018/017052, filed on Feb. 6, 2018, which claims priority to U.S. Provisional Patent Application No. 62/455,424, filed on Feb. 6, 2017, each of which are incorporated herein by reference in their entirety.

STATEMENT AS TO FEDERALLY SPONSORED RESEARCH

This invention was made with government support under Grant Nos. CA206105, CA168611, CA155649, OD010995, and DK034987 awarded by the National Institute of Health and a Department of Defense Peer Reviewed Medical Research Program Grant. The government has certain rights in the invention.

SEQUENCE LISTING

The instant application contains a Sequence Listing which has been submitted electronically in ASCII format and is hereby incorporated by reference in its entirety. Said ASCII copy, created on Aug. 6, 2019, is named PCTUS1817052_SL.txt and is 855 bytes in size.

FIELD

The application relates to methods based on modulating mammalian gastrointestinal (GI) and pancreatic microbiota and related probiotic, prebiotic, and anti-bacterial compositions. Specifically, the application relates to the use of probiotic, prebiotic, and anti-bacterial compositions, for modulating the GI and/or pancreatic microbiomes, as well as for treatment, prevention and diagnosis of pancreatic ductal adenocarcinoma (PDA) at both early and advanced stages.

BACKGROUND

Pancreatic ductal adenocarcinoma (PDA) is the fifth leading cancer diagnosis in the USA and is highly lethal, with ~95% of patients dying within 5 years of diagnosis. PDA is the third most lethal cancer in the United States and accounts for 85% of all pancreatic malignancies. There are no effective means to prevent or delay cancer onset and few effective treatment options exist once transformation has occurred.

Bacteria dysbiosis is emerging as an accomplice to carcinogenesis in extra-pancreatic malignancies such as colon and liver cancer. The average human body, consisting of about $10^{13}$ cells, has about ten times that number of microorganisms. The ~$10^{14}$ microbes that live in and on each of our bodies belong to all three domains of life on earth-bacteria, archaea and eukarya. The major sites for our indigenous microbiota are the intestinal tract, skin and mucosal surfaces such as nasal mucosa and vagina as well as the oropharynx. The gut microbiome has emerged as an important regulator in the balance between health and disease, including oncogenesis[1,2]. The gut microbiome, however, has not been directly linked to PDA[3-6]. Moreover, the role of bacterial microbiota in disease states in non-GI organs such as the pancreas has not been clearly understood or appreciated. Thus, there remains a need for methods for diagnosing, treating and preventing conditions such as PDA based on the gut microbiome.

SUMMARY OF THE INVENTION

As specified in the Background section above, there is a great need in the art for diagnosing, preventing and/or treating pancreatic ductal adenocarcinoma (PDA). The present application addresses these and other needs.

In one aspect, the invention provides a method for treating a pancreatic cancer or tumor in a subject in need thereof, comprising administering to the subject an effective amount of a probiotic or a prebiotic composition or a combination thereof, wherein the composition(s) stimulates growth and/or activity of one or more strains of bacteria from one or more phyla selected from the group consisting of *Actinobacteria* and *Firmicutes* in the pancreatic microbiota of the subject.

In another aspect, the invention provides a method for treating a pancreatic cancer or tumor in a subject in need thereof, comprising administering to the subject an effective amount of a probiotic or a prebiotic composition or a combination thereof, wherein the composition(s) stimulates growth and/or activity of one or more strains of bacteria from one or more phyla selected from the group consisting of *Actinobacteria, Bacteroidetes, Firmicutes, Spirochaetes, Tenericutes,* 7TM7, and *Verrucomicrobia* in the gastrointestinal (GI) microbiota of the subject.

In another aspect, the invention provides a method for treating a pancreatic cancer or tumor in a subject in need thereof, comprising administering to the subject an effective amount of a probiotic or a prebiotic composition or a combination thereof, wherein the composition(s) stimulates growth and/or activity of one or more strains of bacteria from one or more classes selected from the group consisting of *Actinobacteria* and *Clostridia* in the pancreatic microbiota of the subject.

In another aspect, the invention provides a method for treating a pancreatic cancer or tumor in a subject in need thereof, comprising administering to the subject an effective amount of a probiotic or a prebiotic composition or a combination thereof, wherein the composition(s) stimulates growth and/or activity of one or more strains of bacteria from one or more classes selected from the group consisting of *Actinobacteria, Bacteroidia, Bacilli, Brachyspirae, Clostridia, Erysipelotrichi, Mollicutes,* RF3, TM7-3, and *Verrucomicrobiae* in the gastrointestinal (GI) microbiota of the subject.

In another aspect, the invention provides a method for treating a pancreatic cancer or tumor in a subject in need thereof, comprising administering to the subject an effective amount of a probiotic or a prebiotic composition or a combination thereof, wherein the composition(s) stimulates growth and/or activity of one or more strains of bacteria from one or more orders selected from the group consisting of *Actinomycetales, Bifidobacteriales,* and *Clostridiales* in the pancreatic microbiota of the subject.

In another aspect, the invention provides a method for treating a pancreatic cancer or tumor in a subject in need thereof, comprising administering to the subject an effective amount of a probiotic or a prebiotic composition or a combination thereof, wherein the composition(s) stimulates growth and/or activity of one or more strains of bacteria from one or more orders selected from the group consisting of *Bacteroidales, Bifidobacteriales, Brachyspirales, Clostridiales, Erysipelotrichales, Lactobacillales,* ML615J-

28, *Mycoplasmatales*, RF39, TM7 CW040, and *Verrucomicrobiales* in the gastrointestinal (GI) microbiota of the subject.

In another aspect, the invention provides a method for treating a pancreatic cancer or tumor in a subject in need thereof, comprising administering to the subject an effective amount of a probiotic or a prebiotic composition or a combination thereof, wherein the composition(s) stimulates growth and/or activity of one or more strains of bacteria from one or more families selected from the group consisting of *Bifidobacteriaceae, Propionibacteriaceae*, and *Ruminococcaceae* in the pancreatic microbiota of the subject.

In another aspect, the invention provides a method for treating a pancreatic cancer or tumor in a subject in need thereof, comprising administering to the subject an effective amount of a probiotic or a prebiotic composition or a combination thereof, wherein the composition(s) stimulates growth and/or activity of one or more strains of bacteria from one or more families selected from the group consisting of *Bifidobacteriaceae, Bacteroidaceae, Brachyspiraceae, Clostridiaceae, Erysipelotrichaceae, Lachnospiraceae, Lactobacillaceae, Mycoplasmataceae, Peptoniphilaceae, Porphyromonadaceae, Prevotellaceae, Ruminococcaceae, Selenomonadaceae (Veillonellaceae)*, TM7 F16, and *Verrucomicrobiaceae* in the gastrointestinal (GI) microbiota of the subject.

In another aspect, the invention provides a method for treating a pancreatic cancer or tumor in a subject in need thereof, comprising administering to the subject an effective amount of a probiotic or a prebiotic composition or a combination thereof, wherein the composition(s) stimulates growth and/or activity of one or more strains of bacteria from one or more genera selected from the group consisting of *Bifidobacterium, Faecalibacterium*, and *Propionibacterium* in the pancreatic microbiota of the subject.

In another aspect, the invention provides a method for treating a pancreatic cancer or tumor in a subject in need thereof, comprising administering to the subject an effective amount of a probiotic or a prebiotic composition or a combination thereof, wherein the composition(s) stimulates growth and/or activity of one or more strains of bacteria from one or more genera selected from the group consisting of *Akkermansia, Bacteroides, Bifidobacterium, Blautia, Brachyspira, Candidatus arthromitus, Dorea, Eubacterium, Faecalibacterium, Gallicola, Lactobacillus, Megamonas, Mollicutes* RF39, *Mycoplasma, Parabacteroides, Prevotella, Ruminococcus, Tenericutes* ML615J-28, and *Ureaplasma* in the gastrointestinal (GI) microbiota of the subject.

In another aspect, the invention provides a method for treating a pancreatic cancer or tumor in a subject in need thereof, comprising administering to the subject an effective amount of a probiotic or a prebiotic composition or a combination thereof, wherein the composition(s) stimulates growth and/or activity of one or more strains of bacteria from one or more species selected from the group consisting of *Bifidobacterium pseudolongum, Faecalibacterium prausnitzii*, and *Propionibacterium acnes* in the pancreatic microbiota of the subject.

In another aspect, the invention provides a method for treating a pancreatic cancer or tumor in a subject in need thereof, comprising administering to the subject an effective amount of a probiotic or a prebiotic composition or a combination thereof, wherein the composition(s) stimulates growth and/or activity of one or more strains of bacteria from one or more species selected from the group consisting of *Akkermansia muciniphila, Bacteroides eggerthii, Bacteroides fragilis, Bifidobacterium adolescentis, Blautia producta, Candidatus Arthromitus, Eubacterium biforme, Faecalibacterium prausnitzii, Lactobacillus reuteri, Lactobacillus ruminis, Parabacteroides distasonis, Prevotella copri, Ruminococcus gnavus*, and TM7 in the gastrointestinal (GI) microbiota of the subject.

In some embodiments, the method comprises administering a composition comprising one or more strains of bacteria from one or more genera selected from the group consisting of *Bifidobacteriaceae, Propionibacteriaceae*, and *Ruminococcaceae*. In some embodiments, the composition comprises one or more strains of bacteria from one or more genera selected from the group consisting of *Akkermansia, Bacteroides, Bifidobacterium, Blautia, Brachyspira, Candidatus arthromitus, Dorea, Eubacterium, Faecalibacterium, Gallicola, Lactobacillus, Megamonas, Mollicutes* RF39, *Mycoplasma, Parabacteroides, Prevotella, Ruminococcus, Tenericutes* ML615J-28, and *Ureaplasma*.

In some embodiments, the method comprises administering a composition comprising one or more strains of bacteria from one or more species selected from the group consisting of *Bifidobacterium pseudolongum, Faecalibacterium prausnitzii*, and *Propionibacterium acnes*. In some embodiments, the composition comprises one or more strains of bacteria from one or more species selected from the group consisting of *Akkermansia muciniphila, Bacteroides eggerthii, Bacteroides fragilis, Bifidobacterium adolescentis, Blautia producta, Candidatus Arthromitus, Eubacterium biforme, Faecalibacterium prausnitzii, Lactobacillus reuteri, Lactobacillus ruminis, Parabacteroides distasonis, Prevotella copri, Ruminococcus gnavus*, and TM7.

In some embodiments, the method further comprises administering to the subject an effective amount of a compound or composition that inhibits growth and/or activity of one or more strains of bacteria. In certain embodiments, the compound or composition inhibits growth and/or activity of one or more strains of bacterial taxa listed in Table 2. In certain embodiments, the compound or composition inhibits growth and/or activity of one or more strains of bacteria from one or more genera selected from the group consisting of *Bacteroides, Bifidobacterium, Chryseobacterium, Delftia, Elizabethkingia, Lactobacillus, Mucispirillum, Pseudomonas, Streptococcus*, and *Viellonella* in the pancreatic microbiota of the subject. In certain embodiments, the compound or composition inhibits growth and/or activity of one or more strains of bacteria from one or more genera selected from the group consisting of *Akkermansia, Bacteroides, Bifidobacterium, Desulfovibrio, Elizabethkingia, Escherichia, Lactobacillus, Mucispirillum, Oxalobacter, Parabacteroides, Peptostreptococcus, Prevotella, Pyramidobacter, Rothia, Streptococcus*, and *Viellonella* in the gastrointestinal (GI) microbiota of the subject. In certain embodiments, the compound or composition inhibits growth and/or activity of one or more strains of bacteria from one or more species selected from the group consisting of *Bacteroides acidifaciens, Bifidobacterium pseudolongum, Elizabethkingia meningoseptica, Lactobacillus reuteri, Mucispirillum schaedleri, Streptococcus anginosus*, and *Veillonella dispar* in the pancreatic microbiota of the subject. In certain embodiments, the compound or composition inhibits growth and/or activity of one or more strains of bacteria from one or more species selected from the group consisting of *Akkermansia muciniphila, Bacteroides acidifaciens, Bifidobacterium animalis, Bifidobacterium pseudolongum, Desulfovibrio* D168, *Elizabethkingia meningoseptica, Escherichia coli, Lactobacillus reuteri, Mucispirillium schaedleri, Oxalobacter formigenes, Parabacteroides dista-* soni, *Peptostreptococcus anaerobius, Prevotella melaninogenica, Prevotella stercorea, Pyramidobacter piscolens, Rothia mucilaginosa, Streptococcus anginosus*, and *Veillonella dispar* in the gastrointestinal (GI) microbiota of the subject.

In certain embodiments, the compound or composition that inhibits growth and/or activity of one or more strains of bacteria is administered before administration of a probiotic and/or prebiotic or combination thereof that stimulates growth and/or activity of one or more strains of bacteria. In certain embodiments, the compound or composition that inhibits growth and/or activity of one or more strains of bacteria is administered after administration of the probiotic and/or prebiotic or combination thereof that stimulates growth and/or activity of one or more strains of bacteria. In certain embodiments, the compound or composition that inhibits growth and/or activity of one or more strains of bacteria is administered simultaneously with the administration of the probiotic and/or prebiotic or combination thereof that stimulates growth and/or activity of one or more strains of bacteria.

In one aspect, the invention provides a method for treating a pancreatic cancer or tumor in a subject in need thereof, the method comprising administering to the subject an effective amount of a compound or composition, wherein the compound or composition inhibits growth and/or activity of one or more strains of bacteria from one or more phyla selected from the group consisting of *Actinobacteria, Bacteroidetes, Firmicutes, Fusobacteria*, and *Proteobacteria* in the pancreatic microbiota of the subject.

In one aspect, the invention provides a method for treating a pancreatic cancer or tumor in a subject in need thereof, the method comprising administering to the subject an effective amount of a compound or composition, wherein the compound or composition inhibits growth and/or activity of one or more strains of bacteria from one or more phyla selected from the group consisting of *Actinobacteria, Bacteroidetes, Deferribacteres, Euryarchaeota, Firmicutes, Fusobacteria, Proteobacteria, Synergistetes*, TM7, and *Verrucomicrobia* in the gastrointestinal (GI) microbiota of the subject.

In one aspect, the invention provides a method for treating a pancreatic cancer or tumor in a subject in need thereof, the method comprising administering to the subject an effective amount of a compound or composition, wherein the compound or composition inhibits growth and/or activity of one or more strains of bacteria from one or more classes selected from the group consisting of *Bacilli, Clostridia, Flavobacteriia*, and *Gammaproteobacteria* in the pancreatic microbiota of the subject.

In one aspect, the invention provides a method for treating a pancreatic cancer or tumor in a subject in need thereof, the method comprising administering to the subject an effective amount of a compound or composition, wherein the compound or composition inhibits growth and/or activity of one or more strains of bacteria from one or more classes selected from the group consisting of *Actinobacteria, Bacilli, Bacteroidia, Betaproteobacteria, Clostridia, Deferribacteres, Deltaproteobacteria, Flavobacteria, Gammaproteobacteria, Synergistia* and *Verrucomicrobiae* in the gastrointestinal (GI) microbiota of the subject.

In one aspect, the invention provides a method for treating a pancreatic cancer or tumor in a subject in need thereof, the method comprising administering to the subject an effective amount of a compound or composition, wherein the compound or composition inhibits growth and/or activity of one or more strains of bacteria from one or more orders selected from the group consisting of *Clostridiales, Flavobacteriales, Lactobacillales*, and *Pseudomonadales* in the pancreatic microbiota of the subject.

In one aspect, the invention provides a method for treating a pancreatic cancer or tumor in a subject in need thereof, the method comprising administering to the subject an effective amount of a compound or composition, wherein the compound or composition inhibits growth and/or activity of one or more strains of bacteria from one or more orders selected from the group consisting of *Actinomycetales, Bacteroidales, Bifidobacteriales, Burkholderiales, Clostridiales, Deferribacterales, Desulfovibrionales, Enterobacteriales, Flavobacteriales, Lactobacillales, Synergistales* and *Verrucomicrobiales* in the gastrointestinal (GI) microbiota of the subject.

In one aspect, the invention provides a method for treating a pancreatic cancer or tumor in a subject in need thereof, the method comprising administering to the subject an effective amount of a compound or composition, wherein the compound or composition inhibits growth and/or activity of one or more strains of bacteria from one or more families selected from the group consisting of *Enterobacteriaceae, Enterococcaceae, Pseudomonadaceae, Streptococcaceae, Veillonellaceae*, and *Weeksellaceae* in the pancreatic microbiota of the subject.

In one aspect, the invention provides a method for treating a pancreatic cancer or tumor in a subject in need thereof, the method comprising administering to the subject an effective amount of a compound or composition, wherein the compound or composition inhibits growth and/or activity of one or more strains of bacteria from one or more families selected from the group consisting of *Bacteroidaceae, Bifidobacteriaceae, Deferribacteraceae, Desulfovibrionaceae, Dethiosulfovibrionaceae, Enterobacteriaceae, Helicobacteraceae, Lactobacillaceae, Micrococcaceae, Mogibacteriaceae, Mycoplasmataceae, Oxalobacteraceae, Peptostreptococcaceae, Porphyromonadaceae, Prevotellaceae, Streptococcaceae, Veillonellaceae, Verrucomicrobiaceae*, and *Weeksellaceae* and in the gastrointestinal (GI) microbiota of the subject.

In one aspect, the invention provides a method for treating a pancreatic cancer or tumor in a subject in need thereof, the method comprising administering to the subject an effective amount of a compound or composition, wherein the compound or composition inhibits growth and/or activity of one or more strains of bacteria from one or more genera selected from the group consisting of *Bacteroides, Bifidobacterium, Chryseobacterium, Delftia, Elizabethkingia, Lactobacillus, Mucispirillum, Pseudomonas, Streptococcus*, and *Veillonella* in the pancreatic microbiota of the subject.

In one aspect, the invention provides a method for treating a pancreatic cancer or tumor in a subject in need thereof, the method comprising administering to the subject an effective amount of compound or composition, wherein the compound or composition inhibits growth and/or activity of one or more strains of bacteria from one or more genera selected from the group consisting of *Akkermansia, Bacteroides, Bifidobacterium, Desulfovibrio, Elizabethkingia, Escherichia, Lactobacillus, Mucispirillum, Oxalobacter, Parabacteroides, Peptostreptococcus, Prevotella, Pyramidobacter, Rothia, Streptococcus*, and *Veillonella* in the gastrointestinal (GI) microbiota of the subject.

In one aspect, the invention provides a method for treating a pancreatic cancer or tumor in a subject in need thereof, the method comprising administering to the subject an effective amount of a compound or composition, wherein the compound or composition inhibits growth and/or activity of one or more strains of bacteria from one or more species selected from the group consisting of *Bacteroides acidifaciens, Bifidobacterium pseudolongum, Elizabethkingia meningoseptica, Lactobacillus reuteri, Mucispirillum schaedleri Streptococcus anginosus*, and *Veillonella dispar* in the pancreatic microbiota of the subject.

In one aspect, the invention provides a method for treating a pancreatic cancer or tumor in a subject in need thereof, the method comprising administering to the subject an effective amount of a compound or composition, wherein the compound or composition inhibits growth and/or activity of one or more strains of bacteria from one or more species selected from the group consisting of *Akkermansia muciniphila, Bacteroides acidifaciens, Bifidobacterium animalis, Bifidobacterium pseudolongum, Desulfovibrio* D168, *Elizabethkingia meningoseptica, Escherichia coli, Lactobacillus reuteri, Mucispirillum schaedleri, Oxalobacter formigenes, Parabacteroides distasoni, Peptostreptococcus anaerobius, Prevotella melaninogenica, Prevotella stercorea, Pyramidobacter piscolens, Rothia mucilaginosa, Streptococcus anginosus*, and *Veillonella dispar* in the gastrointestinal (GI) microbiota of the subject.

In certain embodiments, the method comprises a compound or composition comprising an antibiotic or natural product that inhibits microbial growth. In certain embodiments, the composition is a probiotic composition which comprises one or more strains of bacteria from one or more genera selected from the group consisting of *Bifidobacteriaceae, Propionibacteriaceae*, and *Ruminococcaceae* that inhibits microbial growth of other bacterial strains. In certain embodiments, the composition is a probiotic composition which comprises one or more strains of bacteria from one or more genera selected from the group consisting of *Akkermansia, Bacteroides, Bifidobacterium, Blautia, Brachyspira, Candidatus arthromitus, Dorea, Eubacterium, Faecalibacterium, Gallicola, Lactobacillus, Megamonas, Mollicutes* RF39, *Mycoplasma, Parabacteroides, Prevotella, Ruminococcus, Tenericutes* ML615J-28, and *Ureaplasma* that inhibits microbial growth of other bacterial strains. In certain embodiments, the composition is a probiotic composition which comprises one or more strains of bacteria from one or more species selected from the group consisting of *Bifidobacterium pseudolongum, Faecalibacterium prausnitzii*, and *Propionibacterium acnes* that inhibits microbial growth of other bacterial strains. In certain embodiments, the composition is a probiotic composition which comprises one or more strains of bacteria from one or more species selected from the group consisting of *Akkermansia muciniphila, Bacteroides eggerthii, Bacteroides fragilis, Bifidobacterium adolescentis, Blautia producta, Candidatus arthromitus, Eubacterium biforme, Faecalibacterium prausnitzii, Lactobacillus reuteri, Lactobacillus ruminis, Parabacteroides distasonis, Prevotella copri, Ruminococcus gnavus*, and TM7 that inhibits microbial growth of other bacterial strains.

In some embodiments, the effective amount is sufficient to inhibit Toll-like receptor (TLR) activity in the cancer cells of the subject. In some embodiments, the effective amount is sufficient to induce recruitment of T cells to the cancer cells of the subject. In some embodiments, the effective amount is sufficient to induce differentiation of the $CD4^+$ T cells. In some embodiments, the effective amount is sufficient to induce expansion and/or activation of the $CD8^+$ T cells. In some embodiments, the effective amount is sufficient to induce recruitment of myeloid derived suppressor cells to the cancer cells of the subject.

In yet another aspect, the invention provides a probiotic composition comprising (i) bacteria from one or more strains of one or more species selected from the group consisting of *Bifidobacterium pseudolongum, Faecalibacterium prausnitzii*, and *Propionibacterium acnes* or a closely related OTU which has at least 90% sequence identity to 16S rRNA of the species over its entire length or has at least 90% sequence identity to any single V region of 16S rRNA of the species, and (ii) a carrier and/or excipient and/or one or more prebiotic agents which stimulate growth and/or activity and/or preserves viability of one or more bacteria present in the composition. In another aspect, the invention provides a probiotic composition comprising (i) bacteria from one or more strains of one or more species selected from the group consisting of *Akkermansia muciniphila, Bacteroides eggerthii, Bacteroides fragilis, Bifidobacterium adolescentis, Blautia producta, Candidatus Arthromitus, Eubacterium biforme, Faecalibacterium prausnitzii, Lactobacillus reuteri, Lactobacillus ruminis, Parabacteroides distasonis, Prevotella copri, Ruminococcus gnavus*, and TM7 or a closely related OTU which has at least 90% sequence identity to 16S rRNA of the species over its entire length or has at least 90% sequence identity to any single V region of 16S rRNA of the species, and (ii) a carrier and/or excipient and/or one or more prebiotic agents which stimulate growth and/or activity and/or preserves viability of one or more bacteria present in the composition. In certain embodiments, the species has at least 95% sequence identity to the 16S rRNA over its entire length or at least 95% sequence identity to any single V region of the 16S rRNA. In certain embodiments, the species has at least 97% sequence identity to the 16S rRNA over its entire length or at least 97% sequence identity to any single V region of the 16S rRNA. In certain embodiments, the species has at least 99% sequence identity to the 16S rRNA over its entire length or at least 99% sequence identity to any single V region of the 16S rRNA. In certain embodiments, the V region of 16S rRNA is the V4 region.

In certain embodiments, the probiotic composition comprises one or more components selected from the group consisting of live bacterial cells, spores, conditionally lethal bacterial cells, inactivated bacterial cells, killed bacterial cells, recombinant carrier strains, cell extract, and bacterially-derived products. In certain embodiments, the probiotic composition stimulates growth and/or activity of one or more strains of bacteria. In certain embodiments, the probiotic composition inhibits growth and/or activity of one or more strains of bacteria.

In certain embodiments, the probiotic comprises strains from two or more different species. In certain embodiments, the probiotic comprises strains from three or more different species. In certain embodiments, the probiotic comprises strains from four or more different species.

In certain embodiments, the probiotic composition is formulated for administration by a route selected from the group consisting of oral, rectal, sublingual, intravenous, and via naso/oro-gastric gavage. In certain embodiments, the probiotic composition is formulated for administration directly to the pancreas.

In yet another aspect, the invention provides a pharmaceutical dosage form comprising the probiotic composition as described above, wherein the probiotic composition is present in an amount effective for treating a pancreatic cancer or tumor. In certain embodiments, the pancreatic cancer is pancreatic ductal adenocarcinoma (PDA). In certain embodiments, the dosage form is in the form of a suspension, a pill, a tablet, a capsule, a powder, a liquid, or a suppository. In certain embodiments, the contents of the suspension, pill, tablet, capsule, or powder are formulated to be released in the intestine of the subject following oral administration of the pill, the tablet, the capsule, or the powder or the liquid to the subject.

In yet another aspect, the invention provides a method for treating a pancreatic cancer or tumor in a subject in need thereof, the method comprising administering to the subject an effective amount of the probiotic composition as described above. In certain embodiments, the method comprises administering to the subject the dosage form as described above.

In another aspect, the compound or composition is administered by a route selected from the group consisting of oral, rectal, sublingual, intravenous, and via naso/oro-gastric gavage. In some embodiments, the compound or composition is administered directly to the pancreas.

In some embodiments, the GI microbiota is selected from the group consisting of cecal, ileal, colonic, and fecal microbiota. In some embodiments, the GI microbiota is fecal microbiota.

In yet another aspect, the pancreatic cancer is pancreatic ductal adenocarcinoma (PDA).

In some embodiments, the method comprises administering an additional cancer therapy. In some embodiments, the additional cancer therapy is selected from the group consisting of surgery, radiotherapy, chemotherapy, immunotherapy, and any combinations thereof. In some embodiments, the chemotherapy is selected from the group consisting of FOLFIRINOX (folinic acid, fluorouracil, irinotecan, and oxaliplatin) gemcitabine, ABRAXANE (albumin-bound paclitaxel), and a combination thereof.

In another aspect, the method further comprises administering a programmed cell death protein 1 (PD-1) inhibitor. In some embodiments, the PD-1 inhibitor is an antibody. In some embodiments, the antibody is pembrolizumab or nivolumab.

In certain embodiments, the subject is human.

In yet another aspect, the invention provides a method for diagnosing predisposition or determining the likelihood of development of pancreatic cancer or tumor in a subject, the method comprising (a) determining the level of at least one strain of bacteria from one or more species in the pancreatic microbiota of the subject, and (b) comparing the level determined in step (a) to the level of the same bacteria in the pancreatic microbiota of healthy controls, and (c) identifying that the subject is predisposed to a pancreatic cancer or tumor wherein the level of at least one of the strains measured in step (a) is at least 35% different than in healthy controls. In certain embodiments, the level of at least one of the strains measured in step (a) is at least 50% different than in healthy controls.

In yet another aspect, the invention provides a method for diagnosing predisposition or determining the likelihood of development of pancreatic cancer or tumor in a subject, the method comprising (a) determining the level of at least one strain of bacteria from one or more species selected from the group consisting of *Bifidobacterium pseudolongum, Faecalibacterium prausnitzii*, and *Propionibacterium acnes* or a closely related OTU within the same genus which has at least 90% sequence identity to 16S rRNA of the species over its entire length or has at least 90% sequence identity to any single V region of 16S rRNA of the species in the pancreatic microbiota of the subject, and (b) comparing the level determined in step (a) to the level of the same bacteria in the pancreatic microbiota of healthy controls, and (c) identifying that the subject is predisposed to a pancreatic cancer or tumor wherein the level of at least one of the strains measured in step (a) is at least 35% lower than in healthy controls. In certain embodiments, the level of at least one of the strains measured in step (a) is at least 50% lower than in healthy controls.

In yet another aspect, the invention provides a method for diagnosing predisposition or determining the likelihood of development of pancreatic cancer or tumor in a subject, the method comprising (a) determining the level of at least one strain of bacteria from one or more species selected from the group consisting of *Akkermansia muciniphila, Bacteroides eggerthii, Bacteroides fragilis, Bifidobacterium adolescentis, Blautia producta, Candidatus Arthromitus, Eubacterium biforme, Faecalibacterium prausnitzii, Lactobacillus reuteri, Lactobacillus ruminis, Parabacteroides distasonis, Prevotella copri, Ruminococcus gnavus*, and TM7 or a closely related OTU within the same genus which has at least 90% sequence identity to 16S rRNA of the species over its entire length or has at least 90% sequence identity to any single V region of 16S rRNA of the species in the gastrointestinal (GI) microbiota of the subject, and (b) comparing the level determined in step (a) to the level of the same bacteria in the gastrointestinal (GI) microbiota of healthy controls, and (c) identifying that the subject is predisposed to a pancreatic cancer or tumor wherein the level of at least one of the strains measured in step (a) is at least 35% lower than in healthy controls.

In certain embodiments, the level of at least one of the strains measured in step (a) is at least 50% lower than in healthy controls.

In yet another aspect, the invention provides a method for diagnosing predisposition or determining the likelihood of development of pancreatic cancer or tumor in a subject further comprising (d) determining the level of at least one strain of bacteria from one or more species selected from the group consisting of *Bacteroides acidifaciens, Bifidobacterium pseudolongum, Elizabethkingia meningoseptica, Lactobacillus reuteri, Mucispirillum schaedleri, Streptococcus anginosus*, and *Veillonella dispar* or a closely related OTU within the same genus which has at least 90% sequence identity to 16S rRNA of the species over its entire length or has at least 90% sequence identity to any single V region of 16S rRNA of the species in the pancreatic microbiota of the subject, and (e) comparing the level determined in step (d) to the level of the same bacteria in the pancreatic microbiota of healthy controls, and (f) identifying that the subject is predisposed to a pancreatic cancer or tumor wherein the level of at least one of the strains measured in step (d) is at least 35% higher than in healthy controls. In certain embodiments, the level of at least one of the strains measured in step (d) is at least 50% higher than in healthy controls.

In yet another aspect, the invention provides a method for diagnosing predisposition or determining the likelihood of development of pancreatic cancer or tumor in a subject further comprising (d) determining the level of at least one strain of bacteria from one or more species selected from the group consisting of *Akkermansia muciniphila, Bacteroides acidifaciens, Bifidobacterium animalis, Bifidobacterium pseudolongum, Desulfovibrio* D168, *Elizabethkingia meningoseptica, Escherichia coli, Lactobacillus reuteri, Mucispirillium schaedleri, Oxalobacter formigenes, Parabacteroides distasoni, Peptostreptococcus anaerobius, Prevotella melaninogenica, Prevotella stercorea, Pyramidobacter piscolens, Rothia mucilaginosa, Streptococcus anginosus*, and *Veillonella dispar* or a closely related OTU within the same genus which has at least 90% sequence identity to 16S rRNA of the species over its entire length or has at least 90% sequence identity to any single V region of 16S rRNA of the species in the gastrointestinal (GI) microbiota of the subject, and (e) comparing the level determined in step (d) to the level of the same bacteria in the gastrointestinal (GI) microbiota of healthy controls, and (f) identifying that the subject is predisposed to a pancreatic cancer or tumor wherein the level of at least one of the strains measured in step (d) is at least 35% higher than in healthy controls. In certain embodiments, the level of at least one of the strains measured in step (d) is at least 50% higher than in healthy controls.

In yet another aspect, the invention provides a method for diagnosing predisposition or determining the likelihood of development of pancreatic cancer or tumor in a subject, the method comprising (a) determining the level of at least one strain of bacteria from one or more species selected from the group consisting of *Bacteroides acidifaciens, Bifidobacterium pseudolongum, Elizabethkingia meningoseptica, Lactobacillus reuteri, Mucispirillum schaedleri, Streptococcus anginosus*, and *Veillonella dispar* or a closely related OTU within the same genus which has at least 90% sequence identity to 16S rRNA of the species over its entire length or has at least 90% sequence identity to any single V region of 16S rRNA of the species in the pancreatic microbiota of the subject, and (b) comparing the level determined in step (a) to the level of the same bacteria in the pancreatic microbiota of healthy controls, and (c) identifying that the subject is predisposed to a pancreatic cancer or tumor wherein the level of at least one of the strains measured in step (a) is at least 35% higher than in healthy controls. In certain embodiments, the level of at least one of the strains measured in step (a) is at least 50% higher than in healthy controls.

In yet another aspect, the invention provides a method for diagnosing predisposition or determining the likelihood of development of pancreatic cancer or tumor in a subject, the method comprising (a) determining the level of (i) at least one strain of bacteria from one or more species selected from the group consisting of *Akkermansia muciniphila, Bacteroides acidifaciens, Bifidobacterium animalis, Bifidobacterium pseudolongum, Desulfovibrio* D168, *Elizabethkingia meningoseptica, Escherichia coli, Lactobacillus reuteri, Mucispirillum schaedleri, Oxalobacter formigenes, Parabacteroides distasoni, Peptostreptococcus anaerobius, Prevotella melaninogenica, Prevotella stercorea, Pyramidobacter piscolens, Rothia mucilaginosa, Streptococcus anginosus*, and *Veillonella dispar* or a closely related OTU within the same genus which has at least 90% sequence identity to 16S rRNA of the species over its entire length or has at least 90% sequence identity to any single V region of 16S rRNA of the species in the gastrointestinal (GI) microbiota of the subject, and (b) comparing the level determined in step (a) to the level of the same bacteria in the gastrointestinal (GI) microbiota of healthy controls, and (c) identifying that the subject is predisposed to a pancreatic cancer or tumor wherein the level of at least one of the strains measured in step (a) is at least 35% higher than in healthy controls. In certain embodiments, the level of at least one of the strains measured in step (a) is at least 50% higher than in healthy controls.

In certain embodiments, the invention provides a method for diagnosing predisposition or determining the likelihood of development of pancreatic cancer or tumor in a subject wherein the species has at least 95%, at least 97%, or at least 99% sequence identity to the 16S rRNA over its entire length or at least 95% at least 97%, or at least 99% sequence identity to any single V region of the 16S rRNA. In certain embodiments, the invention provides a method for diagnosing predisposition or determining the likelihood of development of pancreatic cancer or tumor in a subject wherein the V region of 16S rRNA is the V4 region.

In certain embodiments, the level of bacteria is determined by a method selected from the group consisting of quantitative PCR (qPCR), high-throughput sequencing, transcriptomic analysis, bacterial genotype pattern based fingerprinting (DNA fingerprinting) and proteomic analysis.

In certain embodiments, the invention provides a method for diagnosing predisposition or determining the likelihood of development of pancreatic cancer or tumor in a subject further comprising administering a pancreatic cancer or tumor treatment to the subject. In certain embodiments, the treatment comprises administering to the subject an effective amount of the probiotic composition or the dosage form as described above. In certain embodiments, the treatment comprises a cancer therapy selected from the group consisting of surgery, radiotherapy, chemotherapy, immunotherapy, and any combinations thereof. In certain embodiments, the method further comprises recruiting the subject in a clinical trial.

In certain embodiments, the subject is identified as predisposed to a pancreatic cancer or tumor. In certain embodiments, the pancreatic cancer or tumor is pancreatic ductal adenocarcinoma (PDA). In certain embodiments, the subject is human.

These and other aspects of the present invention will be apparent to those of ordinary skill in the art in the following description, claims and drawings.

BRIEF DESCRIPTION OF THE DRAWINGS

This application contains at least one drawing executed in color corresponding to these drawings. These figures were also submitted in color in U.S. Provisional Patent Application No. 62/455,424, which is incorporated herein by reference in its entirety.

DETAILED DESCRIPTION

Figure 1A:
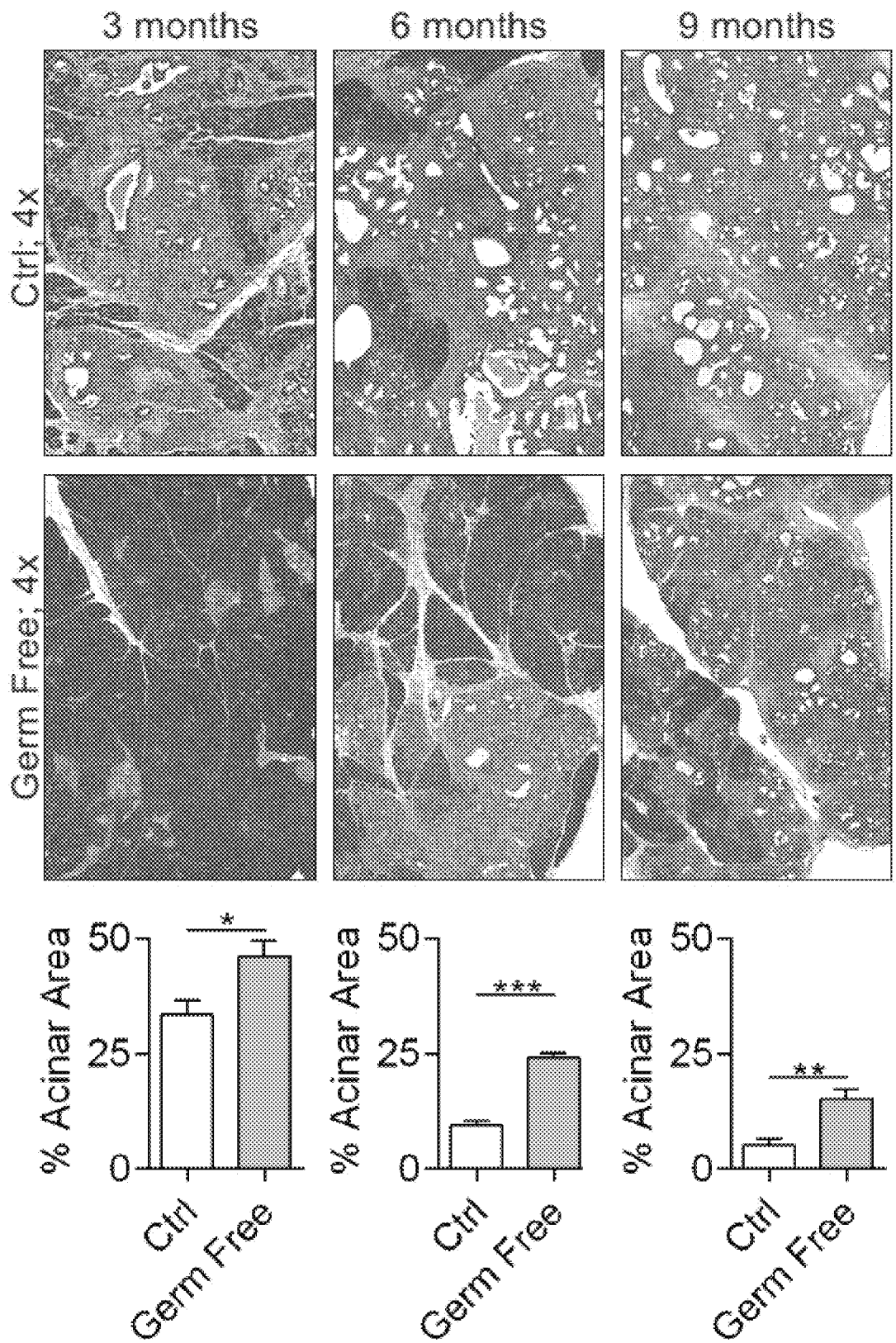
FIGS. 1A-1D. Bacterial ablation is protective against PDA. (1A-1C) Control and germ-free KC mice were sacrificed at 3, 6, or 9 months of age. Representative (1A) H&E- and (1B) trichrome-stained sections are shown and (1C) pancreatic weights were recorded. The percentage of ducts exhibiting normal morphology, acinoductal metaplasia (ADM), or graded PanIN lesions were determined based on H&E staining. The fraction of fibrotic area per pancreas was calculated based on trichrome staining (n=5-11 mice/data point). (1D) WT mice were treated with an ablative oral antibiotic regimen and then orthotopically inoculated with KPC-derived PDA cells. Animals were sacrificed at 3 weeks and their tumor weights were recorded (n=5/group; *$p<0.05$, $p<0.01$, *$p<0.001$, ****$p<0.0001$).

The present invention provides methods and compositions for diagnosing and treating (including preventing) pancreatic cancers such as PDA.

The present invention is based on an unexpected discovery that pancreas has its own microbiome and that both pancreatic and gastrointestinal (GI) microbiomes are important regulators of PDA development in genetically predisposed animal hosts and in human patients. Data in support of each of these findings is presented in the Examples section, below. For instance, it was found that intraluminal bacteria can directly access the pancreas. Also, it was found that the relative abundance of specific bacteria was higher in the gut and/or pancreas of PDA subjects than cancer-free subjects and vice versa. For example, using a mouse model that spontaneously develops PDA, the Example below demonstrated that in the pre-morbid state the intestinal microbiome is similar in mice bearing pancreas-specific oncogenic mutations and in controls; however, as mice age, the PDA-bearing hosts develop a unique gut microbiome including expansion of *Actinobacteria* and *Deferribacteres*. Further, genotypically identical PDA-bearing mice that exhibit divergent disease phenotypes harbor stage-specific microbiomes suggesting that microbial structure is associated with disease aggressiveness. Germ-free or antibiotic treated mice were also protected against PDA; however, endo-luminal administration of pathogenic bacteria accelerates tumorigenesis in genetically predisposed mice. As disclosed herein, the microbiome can be used as a biomarker and therapeutic target in PDA.

As disclosed herein, GI and/or pancreatic microbiome contribute to immune-suppression in PDA. Bacterial ablation was associated with innate and adaptive immunogenic reprogramming of the PDA tumor microenvironment including a marked reduction in myeloid-derived suppressor cells and immune-suppressive macrophages, increased Th1 differentiation of CD4+ T cells, and expansion and activation of cytotoxic CD8+ T cells. In addition, the data herein demonstrates that gut bacterial ablation and PD-1 blockade offer synergistic efficacy. Toll-like receptors (TLRs), which transduce inflammation in response to microbial pathogens, are highly expressed in the pancreatic tumor microenvironment, and that TLR activation accelerates tumorigenesis whereas mice deficient in selected TLRs have slower progression of pancreatic tumorigenesis[8]. Based on these data, the inventors postulated that select pathogenic gut bacteria drive pancreatic carcinogenesis in at-risk hosts via TLR activation, resulting in pathogen-induced immune suppression.

Definitions

As used herein, the terms "microbe" or "microorganism" encompass both prokaryotic organisms including bacteria and archaea, and eukaryotic organisms, including fungi, present in mammalian microbiota, and viruses.

The terms "gastrointestinal microbiota", "GI microbiota", "intestinal microbiota", "intestinal flora", and "intestinal microbiome" are used interchangeably and refer to the microorganisms that colonize the intestines.

The terms "pancreatic microbiota", "pancreatic flora", and "pancreatic microbiome" are used interchangeably and refer to the microorganisms that colonize the pancreas.

As used herein, the term "dysbiosis" refers to a microbial imbalance on or inside the body. Dysbiosis can result from, e.g., antibiotic exposure as well as other causes, e.g., infections with pathogens including viruses, bacteria and eukaryotic parasites.

Specific taxa and changes in GI and pancreatic microbiota discussed herein can be detected using various methods, including without limitation quantitative PCR or high-throughput sequencing methods which detect over- and under-represented genes in the total bacterial population (e.g., 454-sequencing for community analysis; screening of microbial 16S ribosomal RNAs (16S rRNA), etc.), or transcriptomic or proteomic studies that identify lost or gained microbial transcripts or proteins within total bacterial populations. See, e.g., U.S. Patent Publication No. 2010/0074872; Eckburg et al., Science, 2005, 308:1635-8; Costello et al., Science, 2009, 326:1694-7; Grice et al., Science, 2009, 324:1190-2; Li et al., Nature, 2010, 464: 59-65; Bjursell et al., Journal of Biological Chemistry, 2006, 281: 36269-36279; Mahowald et al., PNAS, 2009, 14:5859-5864; Wikoff et al., PNAS, 2009, 10:3698-3703.

As used herein, the term "16S rRNA sequencing" refers to the sequencing of 16S ribosomal RNA (rRNA) gene sequences by using primers such as universal primers and/or species-specific primers to identify the bacteria present in a sample. 16S rRNA genes contain both highly conserved sites and hypervariable regions that can provide species-specific signature sequences useful for identification of bacteria. Such universal primers are well known in the art.

As used herein, the term "operational taxonomic unit" or "OTU" refers to group of bacterial sequences that differ among each other in <97% identity. A "type" or a plurality of "types" of bacteria includes an OTU or a plurality of different OTUs, and also encompasses differences in species, genus, family or order of bacteria. The specific genetic sequence may be the 16S rRNA sequence or a portion of the 16S rRNA sequence or it may be a functionally conserved housekeeping gene found broadly across the eubacterial kingdom.

As used herein, the term "probiotic" refers to a substantially pure bacteria (i.e., a single isolate, of, e.g., live bacterial cells, conditionally lethal bacterial cells, inactivated bacterial cells, killed bacterial cells, spores, recombinant carrier strains), or a mixture of desired bacteria, bacteria components or bacterial extract, or bacterially-derived products (natural or synthetic bacterially-derived products such as, e.g., bacterial antigens or metabolic products) and may also include any additional components that can be administered to a mammal. Such compositions are also referred to herein as bacterial inoculants" or "microbiota inoculants". Probiotics or bacterial inoculant compositions of the invention may be administered with a buffering agent to allow the bacteria to survive in the acidic environment of the stomach, i.e., to resist low pH and to grow in the intestinal environment. Such buffering agents include sodium bicarbonate, juice, milk, yogurt, infant formula, and other dairy products.

As used herein, the term "prebiotic" refers to an agent that simulates the growth (e.g., increases the number) and/or activity of one or more desired bacteria. Non-limiting examples of prebiotics useful in the methods of the present invention include fructooligosaccharides (e.g., oligofructose, inulin, inulin-type fructans), galactooligosaccharides, human milk oligosaccharides (HMO), Lacto-N-neotetraose, D-Tagatose, xylo-oligosaccharides (XOS), arabinoxylan-oligosaccharides (AXOS), N-acetylglucosamine, N-acetylgalactosamine, glucose, other five- and six-carbon sugars (such as arabinose, maltose, lactose, sucrose, cellobiose, etc.), amino acids, alcohols, resistant starch (RS), water-soluble cellulose derivatives (most preferably, methylcellulose, methyl ethyl cellulose, hydroxyethyl cellulose, ethyl hydroxyethyl cellulose, cationic hydroxyethyl cellulose, hydroxypropyl cellulose, hydroxyethyl methylcellulose, hydroxypropyl methylcellulose, and carboxymethyl cellulose), water-insoluble cellulose derivatives (most preferably, ethyl cellulose), and mixtures thereof. See, e.g., Ramirez-Farias et al., Br J Nutr (2008) 4:1-10; Pool-Zobel and Sauer, J Nutr (2007), 137:2580S-2584S.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

As used herein, the term "therapeutically effective amount" refers to the amount of a bacterial inoculant or a compound (e.g., a prebiotic or a probiotic) that, when administered to a subject for treating (e.g., preventing or ameliorating) a state, disorder or condition, is sufficient to effect such treatment. The "therapeutically effective amount" will vary depending, e.g., on the compound, bacteria or analogues administered as well as the disease, its severity, and physical conditions and responsiveness of the subject to be treated.

As used herein, the phrase "pharmaceutically acceptable" refers to molecular entities and compositions that are generally regarded as physiologically tolerable.

As used herein, the term "combination" of a bacterial inoculant, probiotic, analogue, or prebiotic compound and at least a second pharmaceutically active ingredient means at least two, but any desired combination of compounds can be delivered simultaneously or sequentially (e.g., within a 24 hour period).

Within the meaning of the present invention, the term "conjoint administration" is used to refer to administration of a probiotic and a prebiotic simultaneously in one composition, or simultaneously in different compositions, or sequentially (preferably, within a 24 hour period).

The terms "patient", "individual", "subject", and "animal" are used interchangeably herein and refer to mammals, including, without limitation, human and veterinary animals (e.g., cats, dogs, cows, horses, sheep, pigs, etc.) and experimental animal models. In a preferred embodiment, the subject is a human.

As used herein, the term "stimulate" when used in connection with growth and/or activity of bacteria encompasses the term "enhance".

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The terms "a," "an," and "the" do not denote a limitation of quantity, but rather denote the presence of "at least one" of the referenced item.

The practice of the present invention employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J. Additional techniques are explained, e.g., in U.S. Pat. No. 7,912,698 and U.S. Patent Appl. Pub. Nos. 2011/0202322 and 2011/0307437.

Probiotic Therapeutic Methods of the Invention

In one aspect, the invention provides a method for treating (including preventing) pancreatic cancer or tumors in a subject in need thereof, said method comprising administering a probiotic and/or a prebiotic composition, wherein the composition(s) stimulate growth and/or activity of one or more strains of bacteria. In certain embodiments, the pancreatic cancer is pancreatic ductal adenocarcinoma (PDA).

In one embodiment of any of the above methods of the invention, the probiotic is administered to the subject by a route selected from the group consisting of oral, rectal (e.g., by enema), mucosal, sublingual, and via naso/oro-gastric gavage. In one embodiment, the probiotic is administered directly to the pancreas of the subject.

In some embodiments, the probiotic comprises one or more strains of bacteria from the taxa listed Table 1. In certain embodiments, the probiotic comprises at least 2, 3, 4, 5, 6, 7, 8, 9, 10, 20, 50 or more strains from the taxa listed in Table 1. In some embodiments, only nonpathogenic species within the taxa qualify for use in the compositions or methods herein.

TABLE 1

Taxa for Inclusion in Compositions and Methods for Treating (Including Preventing) PDA

| Phylum | | |
|---|---|---|
| Actinobacteria | Bacteroidetes | Firmicutes |
| Spirochaetes | Tenericutes | TM7 |
| Verrucomicrobia | | |

| Class | | |
|---|---|---|
| Actinobacteria | Bacteroidia | Bacilli |
| Brachyspirae | Clostridia | Erysipelotrichi |
| Mollicutes | RF3 | TM7-3 |
| Verrucomicrobiae | | |

| Order | | |
|---|---|---|
| Actinomycetales | Bacteroidales | Bifidobacteriales |
| Brachyspirales | Clostridiales | Erysipelotrichales |
| Lactobacillales | ML615J-28 | Mycoplasmatales |
| RF39 | TM7 CW040 | Verrucomicrobiales |

| Family | | |
|---|---|---|
| Bifidobacteriaceae | Bacteroidaceae | Brachyspiraceae |
| Clostridiaceae | Erysipelotrichaceae | Lachnospiraceae |
| Lactobacillaceae | Mycoplasmataceae | Peptoniphilaceae |
| Porphyromonadaceae | Prevotellaceae | Propionibacteriaceae |
| Ruminococcaceae | Selenomonadaceae (Veillonellaceae) | TM7 F16 |
| Verrucomicrobiaceae | | |

| Genera | | |
|---|---|---|
| Akkermansia | Bacteroides | Bifidobacterium |
| Blautia | Brachyspira | Candidatus arthromitus |
| Dorea | Eubacterium | Faecalibacterium |
| Gallicola | Lactobacillus | Megamonas |
| Mollicutes RF39 | Mycoplasma | Parabacteroides |
| Prevotella | Propionibacterium | Ruminococcus |
| Tenericutes | ML615J-28 | Ureaplasma |

| Species | | |
|---|---|---|
| Akkermansia muciniphila | Bacteroides eggerthii | Bacteroides fragilis |
| Bifidobacterium adolescentis | Bifidobacterium pseudolongum | Blautia producta |

TABLE 1-continued

Taxa for Inclusion in Compositions and Methods for Treating (Including Preventing) PDA

| | | |
|---|---|---|
| Candidatus arthromitus | Eubacterium biforme | Faecalibacterium prausnitzii |
| Lactobacillus reuteri | Lactobacillus ruminis | Parabacteroides distasonis |
| Prevotella copri | Propionibacterium acnes | Ruminococcus gnavus |
| TM7 | | |

In some embodiments of any of the above methods involving administration of a probiotic composition, said probiotic composition comprises one or more OTUs which are independently characterized by, i.e., at least 95%, 96%, 97%, 98%, 99% or including 100% sequence identity to 16S rRNA sequences of the bacteria recited in Table 1. In another embodiment, the OTUs may be characterized by one or more of the variable regions of the 16S rRNA sequence (V1-V9). These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. (See, e.g., Brosius et al., Complete nucleotide sequence of a 16S ribosomal RNA gene from *Escherichia coli*, PNAS 75(10):4801-4805 (1978)). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU.

In some embodiments, the probiotic is administered to the subject in an effective amount sufficient to inhibit Toll-like receptor (TLR) activity in the cancer cells of the subject. In some embodiments, the probiotic is administered to the subject in an effective amount sufficient to induce T cells to the cancer or tumor cells of the subject. In some embodiments, the CD4+ T cells are differentiated. In some embodiments, the CD8+ T cells are expanded, activated, or both. In some embodiments, the probiotic is administered to the subject in an effective amount sufficient to induce recruitment of myeloid derived suppressor cells to the cancer or tumor cells of the subject.

In some embodiments, the method comprises administering to the subject an effective amount of a probiotic or a prebiotic composition or a combination thereof, wherein said composition(s) stimulates growth and/or activity of one or more strains of bacteria from the taxa listed in Table 1 in the pancreatic microbiota of the subject. In certain embodiments, the composition comprises at least 2, 3, 4, 5, 6, 7, 8, 9, 10, 20, 50 or more strains from the taxa listed in Table 1.

In certain embodiments, the method comprises administered to the subject an effective amount of a probiotic or a prebiotic composition or a combination thereof, wherein said composition(s) stimulates growth and/or activity or includes of one or more strains of bacteria from one or more phyla selected from the group consisting of *Actinobacteria* and *Firmicutes* in the pancreatic microbiota of the subject. In certain embodiments, the composition comprises at least 2, 3, 4, 5, 6, 7, 8, 9, 10, 20, 50 or more strains from this taxa.

In certain embodiments, the method comprises administered to the subject an effective amount of a probiotic or a prebiotic composition or a combination thereof, wherein said composition(s) stimulates growth and/or activity or includes of one or more strains of bacteria from one or more classes selected from the group consisting of *Actinobacteria* and *Clostridia* in the pancreatic microbiota of the subject. In certain embodiments, the composition comprises at least 2, 3, 4, 5, 6, 7, 8, 9, 10, 20, 50 or more strains from this taxa.

In certain embodiments, the method comprises administered to the subject an effective amount of a probiotic or a prebiotic composition or a combination thereof, wherein said composition(s) stimulates growth and/or activity or includes of one or more strains of bacteria from one or more orders selected from the group consisting of *Actinomycetales, Bifidobacteriales*, and *Clostridiales* in the pancreatic microbiota of the subject. In certain embodiments, the composition comprises at least 2, 3, 4, 5, 6, 7, 8, 9, 10, 20, 50 or more strains from this taxa.

In certain embodiments, the method comprises administered to the subject an effective amount of a probiotic or a prebiotic composition or a combination thereof, wherein said composition(s) stimulates growth and/or activity or includes of one or more strains of bacteria from one or more families selected from the group consisting of *Propionibacteriaceae, Bifidobacteriaceae*, and *Ruminococcaceae* in the pancreatic microbiota of the subject. In certain embodiments, the composition comprises at least 2, 3, 4, 5, 6, 7, 8, 9, 10, 20, 50 or more strains from this taxa.

In certain embodiments, the method comprises administered to the subject an effective amount of a probiotic or a prebiotic composition or a combination thereof, wherein said composition(s) stimulates growth and/or activity or includes of one or more strains of bacteria from one or more genera selected from the group consisting of *Bifidobacterium, Faecalibacterium*, and *Propionibacterium* in the pancreatic microbiota of the subject. In certain embodiments, the composition comprises at least 2, 3, 4, 5, 6, 7, 8, 9, 10, 20, 50 or more strains from this taxa.

In certain embodiments, the method comprises administered to the subject an effective amount of a probiotic or a prebiotic composition or a combination thereof, wherein said composition(s) stimulates growth and/or activity or includes of one or more strains of bacteria from one or more species selected from the group consisting of *Bifidobacterium pseudolongum, Faecalibacterium prausnitzii*, and *Propionibacterium acnes* in the pancreatic microbiota of the subject. In certain embodiments, the composition comprises at least 2, 3, 4, 5, 6, 7, 8, 9, 10, 20, 50 or more strains from this taxa.

In some embodiments, the method comprises administering to the subject an effective amount of a probiotic or a prebiotic composition or a combination thereof, wherein said composition(s) stimulates growth and/or activity of one or more strains of bacteria from the taxa listed in Table 1 in the gastrointestinal (GI) microbiota of the subject. In certain embodiments, the composition comprises at least 2, 3, 4, 5, 6, 7, 8, 9, 10, 20, 50 or more strains from the taxa listed in Table 1. In certain embodiments, the GI microbiota is selected from the group consisting of cecal, ileal, colonic, and fecal microbiota. In certain embodiments, the GI microbiota is fecal microbiota.

In certain embodiments, the method comprises administered to the subject an effective amount of a probiotic or a prebiotic composition or a combination thereof, wherein said composition(s) stimulates growth and/or activity or includes of one or more strains of bacteria from one or more phyla selected from the group consisting of *Actinobacteria, Bacteroidetes, Firmicutes, Spirochaetes, Tenericutes*, TM7, and *Verrucomicrobia* in the gastrointestinal (GI) microbiota of the subject. In certain embodiments, the composition comprises at least 2, 3, 4, 5, 6, 7, 8, 9, 10, 20, 50 or more strains from this taxa.

In certain embodiments, the method comprises administered to the subject an effective amount of a probiotic or a prebiotic composition or a combination thereof, wherein said composition(s) stimulates growth and/or activity or includes of one or more strains of bacteria from one or more classes selected from the group consisting of *Actinobacteria, Bacteroidia, Bacilli, Brachyspirae, Clostridia, Erysipelotrichi, Mollicutes*, RF3, TM7-3, and *Verrucomicrobiae* in the gastrointestinal (GI) microbiota of the subject. In certain embodiments, the composition comprises at least 2, 3, 4, 5, 6, 7, 8, 9, 10, 20, 50 or more strains from this taxa.

In certain embodiments, the method comprises administered to the subject an effective amount of a probiotic or a prebiotic composition or a combination thereof, wherein said composition(s) stimulates growth and/or activity or includes of one or more strains of bacteria from one or more orders selected from the group consisting of *Bacteroidales, Bifidobacteriales, Brachyspirales, Clostridiales, Erysipelotrichales, Lactobacillales*, ML615J-28, *Mycoplasmatales*, RF39, TM7 CW040, and *Verrucomicrobiales* in the gastrointestinal (GI) microbiota of the subject. In certain embodiments, the composition comprises at least 2, 3, 4, 5, 6, 7, 8, 9, 10, 20, 50 or more strains from this taxa.

In certain embodiments, the method comprises administered to the subject an effective amount of a probiotic or a prebiotic composition or a combination thereof, wherein said composition(s) stimulates growth and/or activity or includes of one or more strains of bacteria from one or more families selected from the group consisting of *Bifidobacteriaceae, Bacteroidaceae, Brachyspiraceae, Clostridiaceae, Erysipelotrichaceae, Lachnospiraceae, Lactobacillaceae, Mycoplasmataceae, Peptoniphilaceae, Porphyromonadaceae, Prevotellaceae, Ruminococcaceae, Selenomonadaceae (Veillonellaceae)*, TM7 F16, and *Verrucomicrobiaceae* in the gastrointestinal (GI) microbiota of the subject. In certain embodiments, the composition comprises at least 2, 3, 4, 5, 6, 7, 8, 9, 10, 20, 50 or more strains from this taxa.

In certain embodiments, the method comprises administered to the subject an effective amount of a probiotic or a prebiotic composition or a combination thereof, wherein said composition(s) stimulates growth and/or activity or includes of one or more strains of bacteria from one or more genera selected from the group consisting of *Akkermansia, Bacteroides, Bifidobacterium, Blautia, Brachyspira, Candidatus arthromitus, Dorea, Eubacterium, Faecalibacterium, Gallicola, Lactobacillus, Megamonas, Mollicutes* RF39, *Mycoplasma, Parabacteroides, Prevotella, Ruminococcus, Tenericutes* ML615J-28, and *Ureaplasma* in the gastrointestinal (GI) microbiota of the subject. In certain embodiments, the composition comprises at least 2, 3, 4, 5, 6, 7, 8, 9, 10, 20, 50 or more strains from this taxa.

In certain embodiments, the method comprises administered to the subject an effective amount of a probiotic or a prebiotic composition or a combination thereof, wherein said composition(s) stimulates growth and/or activity or includes of one or more strains of bacteria from one or more species selected from the group consisting of *Akkermansia muciniphila, Bacteroides eggerthii, Bacteroides fragilis, Bifidobacterium adolescentis, Blautia producta, Candidatus Arthromitus, Eubacterium biforme, Faecalibacterium prausnitzii, Lactobacillus reuteri, Lactobacillus ruminis, Parabacteroides distasonis, Prevotella copri, Ruminococcus gnavus*, and TM7 in the gastrointestinal (GI) microbiota of the subject. In certain embodiments, the composition comprises at least 2, 3, 4, 5, 6, 7, 8, 9, 10, 20, 50 or more strains from this taxa.

Within a given composition, different bacterial strains can be contained in equal amounts (even combination) or in various proportions (uneven combinations) needed for achieving the maximal biological activity. For example, in a bacterial composition with two bacterial strains, the strains may be present in from a 1:10,000 ratio to a 1:1 ratio, from a 1:10,000 ratio to a 1:1,000 ratio, from a 1:1,000 ratio to a 1:100 ratio, from a 1:100 ratio to a 1:50 ratio, from a 1:50 ratio to a 1:20 ratio, from a 1:20 ratio to a 1:10 ratio, from a 1:10 ratio to a 1:1 ratio. For bacterial compositions comprising at least three bacterial strains, the ratio of strains may be chosen pairwise from ratios for bacterial compositions with two strains. For example, in a bacterial composition comprising bacterial strains A, B, and C, at least one of the ratios between strain A and B, the ratio between strain B and C, and the ratio between strain A and C may be chosen, independently, from the pairwise combinations above. In one specific embodiment, the invention encompasses administering two or more bacteria-containing compositions to the same subject. Such compositions can be administered simultaneously or sequentially.

In one embodiment of any of the above methods of the invention, the probiotic is administered in a therapeutically effective amount. The dosages of the microbiota inoculum and/or probiotic composition administered in the methods of the invention will vary widely, depending upon the subject's physical parameters, the frequency of administration, the manner of administration, the clearance rate, and the like. The initial dose may be larger, and might be followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve colonization, e.g. $10^6$, $10^7$, $10^8$, $10^9$, and $10^{10}$ CFU for example, can be administered in a single dose. Lower doses can also be effective, e.g., $10^4$, and $10^5$ CFU.

The probiotic composition useful in any of the above methods can comprise, without limitation, e.g., live bacterial cells, conditionally lethal bacterial cells, inactivated bacterial cells, killed bacterial cells, spores (e.g., germination-competent spores), recombinant carrier strains, cell extract, and bacterially-derived products (natural or synthetic bacterially-derived products such as, e.g., bacterial antigens or bacterial metabolic products).

Bacterial strains administered in probiotic compositions according to the methods of the present invention can comprise live bacteria. One or several different bacterial inoculants can be administered simultaneously or sequentially (including administering at different times). Such bacteria can be isolated from gastrointestinal (GI) or pancreatic microbiota and grown in culture. The present invention also comprises administering "bacterial analogues", such as recombinant carrier strains expressing one or more heterologous genes derived from the relevant bacterial species. The use of such recombinant bacteria may allow the use of lower therapeutic amounts due to higher protein expression. Non-limiting examples of recombinant carrier strains useful in the methods of the present invention include *E. coli* and *Lactobacillus, Bacteroides* and *Oxalobacter*. Methods describing the use of bacteria for heterologous protein delivery are described, e.g., in U.S. Pat. No. 6,803,231.

Methods for producing bacterial compositions of the invention may include three main processing steps, combined with one or more mixing steps. The steps are: organism banking, organism production, and preservation. For banking, the strains included in the bacterial compositions of the invention may be (1) isolated directly from a specimen or taken from a banked stock, (2) optionally cultured on a nutrient agar or broth that supports growth to generate viable biomass, and (3) the biomass optionally preserved in multiple aliquots in long-term storage. The bacterial suspension can be freeze-dried to a powder and titrated. After drying, the powder may be blended to an appropriate potency, and mixed with other cultures and/or a filler such as microcrystalline cellulose for consistency and ease of handling, and the bacterial composition formulated as provided herein.

In one embodiment of any of the above methods of the invention, the probiotic is delivered to the subject in a form of a suspension, a pill, a tablet, a capsule, or a suppository. In another embodiment, the probiotic is delivered to the subject in a form of a liquid, foam, cream, spray, powder, or gel. In yet another embodiment, the probiotic is delivered to the subject in a saline suspension for use in feeding tubes, transmission via nasogastric tube, or enema. If live bacteria are used, the carrier should preferably contain an ingredient that promotes viability of the bacteria during storage.

The formulation can include added ingredients to improve palatability, improve shelf-life, impart nutritional benefits, and the like. If a reproducible and measured dose is desired, the bacteria can be administered by a rumen cannula.

In one embodiment of any of the above methods of the invention, the bacterial inoculum is delivered to the subject in a form of a composition which comprises (i) a carrier and/or excipient and/or (ii) one or more prebiotic agents which stimulate growth and/or activity of one or more bacteria present in the composition. In one specific embodiment, said composition comprises an excipient or a carrier that optimizes the seeding of the transferred microbiota.

In one embodiment of any of the above methods involving administration of a probiotic composition, said probiotic composition is reconstituted from a lyophilized preparation. In one embodiment of any of the above methods involving administration of a probiotic composition, said probiotic composition comprises a buffering agent to adjust pH.

In one embodiment, the probiotic composition comprises a buffering agent (e.g., sodium bicarbonate, infant formula, or other agents which allow bacteria to survive and grow [e.g., survive in the acidic environment of the stomach and to grow in the intestinal environment]), along with preservatives, stabilizers, binders, compaction agents, lubricants, dispersion enhancers, disintegration agents, antioxidants, flavoring agents, sweeteners, and coloring agents.

In one embodiment of any of the above methods involving administration of a probiotic composition, the probiotic composition is administered conjointly with a prebiotic which stimulates growth and/or activity of bacteria contained in the probiotic composition. Non-limiting examples of useful prebiotics include, e.g., galactose, β-N-Acetyl-α-glucosamine, pyroglutamtamic acid, arginine, serine, glycine, fructooligosaccharides (FOS), galactooligosaccharides (GOS), human milk oligosaccharides (HMO), Lacto-N-neotetraose, D-Tagatose, xylo-oligosaccharides (XOS), arabinoxylan-oligosaccharides (AXOS), N-acetylglucosamine, N-acetylgalactosamine, glucose, arabinose, maltose, lactose, sucrose, cellobiose, amino acids, alcohols, resistant starch (RS), electrolytes and any combinations thereof. In some embodiments, the electrolytes can modulate or balance the pH. In one specific embodiment, the probiotic and prebiotic are administered in one composition, or simultaneously as two separate compositions, or sequentially.

In one embodiment of any of the above methods, the method further comprises monitoring the subject's microbiota after the administration of the bacterial inoculum by: (a) determining a relative abundance of one or more bacterial taxa in a GI or pancreatic microbiota sample obtained from the subject (e.g., isolated from feces, intestines, etc.), and (b) comparing the relative abundance(s) determined in step (a) to (i) a predetermined standard value or (ii) to the abundance(s) of the same taxa in a control subject (e.g., a healthy subject) or (iii) to the average value of abundances of the same taxa in several control subjects. Non-limiting examples of the methods which can be used for determining the relative abundance of the bacterial taxa include, e.g., quantitative polymerase chain reaction (qPCR), sequencing of bacterial 16S rRNA, shotgun metagenome sequencing, bacterial genotype pattern based fingerprinting (DNA fingerprinting), and metabolomics. In one specific embodiment, the method involves determining a relative abundance of the bacteria from the taxa listed in Table 1 or the lists above.

Anti-Bacterial Therapeutic Methods of the Invention

In one aspect, the invention provides a method for treating (including preventing) pancreatic cancer or tumors in a subject in need thereof, said method comprising a compound or composition, wherein the compound or composition inhibits growth and/or activity of one or more strains of bacteria. In certain embodiment, the growth is inhibited to the extent that the bacterial strains are removed from the microbiota (i.e., reduced or ablated). In certain embodiments, the pancreatic cancer is pancreatic ductal adenocarcinoma (PDA).

In one embodiment of any of the above methods of the invention, the compound or composition that inhibits growth and/or activity of one or more strains of bacteria is administered to the subject by a route selected from the group consisting of oral, rectal (e.g., by enema), mucosal, sublingual, and via naso/oro-gastric gavage. In one embodiment, the compound or composition that inhibits growth and/or activity of one or more strains of bacteria is administered directly to the pancreas of the subject.

In some embodiments, the compound or composition inhibits growth and/or activity of one or more strains of bacteria from the taxa listed Table 2. In certain embodiments, the compound or composition inhibits growth and/or activity of at least 2, 3, 4, 5, 6, 7, 8, 9, 10, 20, 50 or more strains from the taxa listed in Table 2.

TABLE 2

Taxa for Ablation or Anti-Bacterial Treatment to Treat and/or Prevent Pancreatic Cancer (e.g., PDA)

Phylum

| | | |
|---|---|---|
| Actinobacteria | Bacteroidetes | Deferribacteres |
| Euryarchaeota | Firmicutes | Fusobacteria |
| Proteobacteria | Synergistetes | TM7 |
| Verrucomicrobia | | |

Class

| | | |
|---|---|---|
| Actinobacteria | Bacilli | Bacteroidia |
| Betaproteobacteria | Clostridia | Deferribacteres |
| Deltaproteobacteria | Flavobacteria | Gammaproteobacteria |
| Synergistia | Verrucomicrobiae | |

TABLE 2-continued

Taxa for Ablation or Anti-Bacterial Treatment to Treat and/or Prevent Pancreatic Cancer (e.g., PDA)

Order

| | | |
|---|---|---|
| Actinomycetales | Bacteroidales | Bifidobacteriales |
| Burkholderiales | Clostridiales | Deferribacterales |
| Desulfovibrionales | Enterobacteriales | Flavobacteriales |
| Lactobacillales | Pseudomonadales | Synergistales |
| Verrucomicrobiales | | |

Family

| | | |
|---|---|---|
| Bacteroidaceae | Bifidobacteriaceae | Deferribacteraceae |
| Desulfovibrionaceae | Dethiosulfovibrionaceae | Enterobacteriaceae |
| Enterococcaceae | Helicobacteraceae | Lactobacillaceae |
| Micrococcaceae | Mogibacteriaceae | Mycoplasmataceae |
| Oxalobacteraceae | Peptostreptococcaceae | Porphyromonadaceae |
| Prevotellaceae | Pseudomonadaceae | Streptococcaceae |
| Veillonellaceae | Verrucomicrobiaceae | Weeksellaceae |

Genera

| | | |
|---|---|---|
| Akkermansia | Bacteroides | Bifidobacterium |
| Chryseobacterium | Delftia | Desulfovibrio |
| Elizabethkingia | Escherichia | Lactobacillus |
| Mucispirillum | Oxalobacter | Parabacteroides |
| Peptostreptococcus | Prevotella | Pseudomonas |
| Pyramidobacter | Rothia | Streptococcus |
| Viellonella | | |

Species

| | | |
|---|---|---|
| Akkermansia muciniphila | Bacteroides acidifaciens | Bifidobacterium animalis |
| Bifidobacterium pseudolongum | Desulfovibrio D168 | Elizabethkingia meningoseptica |
| Escherichia coli | Lactobacillus reuteri | Mucispirillum schaedleri |
| Oxalobacter formigenes | Parabacteroides distasonis | Peptostreptococcus anaerobius |
| Prevotella melaninogenica | Prevotella stercorea | Pseudomonas spp. |
| Pyramidobacter piscolens | Rothia mucilaginosa | Streptococcus anginosus |
| Veillonella dispar | | |

In some embodiments of any of the above methods involving administration of a compound or composition that inhibits growth and/or activity of one or more strains of bacteria of Table 2 or a closely related OTUs which are independently characterized by, i.e., at least 95%, 96%, 97%, 98%, 99% or including 100% sequence identity to 16S rRNA sequences of the bacteria recited in Table 2. In another embodiment, the OTUs may be characterized by one or more of the variable regions of the 16S rRNA sequence (V1-V9). These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. (See, e.g., Brosius et al., Complete nucleotide sequence of a 16S ribosomal RNA gene from *Escherichia coli*, PNAS 75(10):4801-4805 (1978)). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU.

In some embodiments, the composition is administered to the subject in an effective amount sufficient to inhibit Toll-like receptor (TLR) activity in the cancer cells of the subject. In some embodiments, the composition is administered to the subject in an effective amount sufficient to induce T cells to the cancer or tumor cells of the subject. In some embodiments, the CD4+ T cells are differentiated. In some embodiments, the CD8+ T cells are expanded, activated, or both. In some embodiments, the composition is administered to the subject in an effective amount sufficient to induce recruitment of myeloid derived suppressor cells to the cancer or tumor cells of the subject.

In some embodiments, the compound or composition inhibits growth and/or activity of one or more strains of bacteria from the taxa listed Table 2 in the pancreatic microbiota of the subject. In certain embodiments, the compound or composition inhibits growth and/or activity of at least 2, 3, 4, 5, 6, 7, 8, 9, 10, 20, 50 or more strains from the taxa listed in Table 2.

In certain embodiments, the method comprising administering to the subject an effective amount of a compound or composition, wherein the compound or composition inhibits growth and/or activity of one or more strains of bacteria from one or more phyla selected from the group consisting of *Actinobacteria, Bacteroidetes, Firmicutes, Fusobacteria*, and *Proteobacteria* in the pancreatic microbiota of the subject. In certain embodiments, the compound or composition inhibits growth and/or activity of at least 2, 3, 4, 5, 6, 7, 8, 9, 10, 20, 50 or more strains from this taxa.

In certain embodiments, the method comprising administering to the subject an effective amount of a compound or composition, wherein the compound or composition inhibits growth and/or activity of one or more strains of bacteria from one or more classes selected from the group consisting of *Bacilli, Clostridia, Flavobacteriia*, and *Gammaproteobacteria* in the pancreatic microbiota of the subject. In certain embodiments, the compound or composition inhibits growth and/or activity of at least 2, 3, 4, 5, 6, 7, 8, 9, 10, 20, 50 or more strains from this taxa.

In certain embodiments, the method comprising administering to the subject an effective amount of a compound or composition, wherein the compound or composition inhibits growth and/or activity of one or more strains of bacteria from one or more orders selected from the group consisting of *Clostridiales, Flavobacteriales, Lactobacillales*, and *Pseudomonadales* in the pancreatic microbiota of the subject. In certain embodiments, the compound or composition inhibits growth and/or activity of at least 2, 3, 4, 5, 6, 7, 8, 9, 10, 20, 50 or more strains from this taxa.

In certain embodiments, the method comprising administering to the subject an effective amount of a compound or composition, wherein the compound or composition inhibits growth and/or activity of one or more strains of bacteria from one or more families selected from the group consisting of *Enterobacteriaceae, Enterococcaceae, Pseudomonadaceae, Streptococcaceae, Veillonellaceae*, and *Weeksellaceae* in the pancreatic microbiota of the subject. In certain embodiments, the compound or composition inhibits growth and/or activity of at least 2, 3, 4, 5, 6, 7, 8, 9, 10, 20, 50 or more strains from this taxa.

In certain embodiments, the method comprising administering to the subject an effective amount of a compound or composition, wherein the compound or composition inhibits growth and/or activity of one or more strains of bacteria from one or more genera selected from the group consisting of *Bacteroides, Bifidobacterium, Chryseobacterium, Delftia Elizabethkingia, Lactobacillus, Mucispirillum, Pseudomonas, Streptococcus*, and *Viellonella* in the pancreatic microbiota of the subject. In certain embodiments, the compound or composition inhibits growth and/or activity of at least 2, 3, 4, 5, 6, 7, 8, 9, 10, 20, 50 or more strains from this taxa.

In certain embodiments, the method comprising administering to the subject an effective amount of a compound or composition, wherein the compound or composition inhibits growth and/or activity of one or more strains of bacteria from one or more species selected from the group consisting of *Bacteroides acidifaciens, Bifidobacterium pseudolongum, Elizabethkingia meningoseptica, Lactobacillus reuteri, Mucispirillum schaedleri, Pseudomonas* spp., *Streptococcus anginosus*, and *Veillonella dispar* in the pancreatic microbiota of the subject. In certain embodiments, the compound or composition inhibits growth and/or activity of at least 2, 3, 4, 5, 6, 7, 8, 9, 10, 20, 50 or more strains from this taxa.

In some embodiments, the compound or composition inhibits growth and/or activity of one or more strains of bacteria from the taxa listed Table 2 in the GI microbiota of the subject. In certain embodiments, the compound or composition inhibits growth and/or activity of at least 2, 3, 4, 5, 6, 7, 8, 9, 10, 20, 50 or more strains from the taxa listed in Table 2. In certain embodiments, the GI microbiota is selected from the group consisting of cecal, ileal, colonic, and fecal microbiota. In certain embodiments, the GI microbiota is fecal microbiota.

In certain embodiments, the method comprising administering to the subject an effective amount of a compound or composition, wherein the compound or composition inhibits growth and/or activity of one or more strains of bacteria from one or more phyla selected from the group consisting of *Actinobacteria, Bacteroidetes, Deferribacteres, Euryarchaeota, Firmicutes, Fusobacteria, Proteobacteria, Synergistetes*, TM7, and *Verrucomicrobia* in the gastrointestinal (GI) microbiota of the subject. In certain embodiments, the compound or composition inhibits growth and/or activity of at least 2, 3, 4, 5, 6, 7, 8, 9, 10, 20, 50 or more strains from this taxa.

In certain embodiments, the method comprising administering to the subject an effective amount of a compound or composition, wherein the compound or composition inhibits growth and/or activity of one or more strains of bacteria from one or more classes selected from the group consisting of *Actinobacteria, Bacilli, Bacteroidia, Betaproteobacteria, Clostridia, Deferribacteres, Flavobacteria, Gammaproteobacteria, Deltaproteobacteria, Synergistia* and *Verrucomicrobiae* in the gastrointestinal (GI) microbiota of the subject. In certain embodiments, the compound or composition inhibits growth and/or activity of at least 2, 3, 4, 5, 6, 7, 8, 9, 10, 20, 50 or more strains from this taxa.

In certain embodiments, the method comprising administering to the subject an effective amount of a compound or composition, wherein the compound or composition inhibits growth and/or activity of one or more strains of bacteria from one or more orders selected from the group consisting of *Actinomycetales, Bacteroidales, Bifidobacteriales, Burkholderiales, Clostridiales, Deferribacterales, Desulfovibrionales, Enterobacteriales, Flavobacteriales, Lactobacillales, Synergistales* and *Verrucomicrobiales* in the gastrointestinal (GI) microbiota of the subject. In certain embodiments, the compound or composition inhibits growth and/or activity of at least 2, 3, 4, 5, 6, 7, 8, 9, 10, 20, 50 or more strains from this taxa.

In certain embodiments, the method comprising administering to the subject an effective amount of a compound or composition, wherein the compound or composition inhibits growth and/or activity of one or more strains of bacteria from one or more families selected from the group consisting of *Bacteroidaceae, Bifidobacteriaceae, Deferribacteraceae, Desulfovibrionaceae, Dethiosulfovibrionaceae, Enterobacteriaceae, Helicobacteraceae, Lactobacillaceae, Micrococcaceae, Mogibacteriaceae, Mycoplasmataceae, Peptostreptococcaceae, Oxalobacteraceae, Porphyromonadaceae, Prevotellaceae, Streptococcaceae, Veillonellaceae*,

*Verrucomicrobiaceae*, and *Weeksellaceae* in the gastrointestinal (GI) microbiota of the subject. In certain embodiments, the compound or composition inhibits growth and/or activity of at least 2, 3, 4, 5, 6, 7, 8, 9, 10, 20, 50 or more strains from this taxa.

In certain embodiments, the method comprising administering to the subject an effective amount of a compound or composition, wherein the compound or composition inhibits growth and/or activity of one or more strains of bacteria from one or more genera selected from the group consisting of *Akkermansia, Bacteroides, Bifidobacterium, Desulfovibrio, Elizabethkingia, Escherichia, Mucispirillum, Lactobacillus, Oxalobacter, Parabacteroides, Peptostreptococcus, Prevotella, Pyramidobacter, Streptococcus, Rothia*, and *Viellonella* in the gastrointestinal (GI) microbiota of the subject. In certain embodiments, the compound or composition inhibits growth and/or activity of at least 2, 3, 4, 5, 6, 7, 8, 9, 10, 20, 50 or more strains from this taxa.

In certain embodiments, the method comprising administering to the subject an effective amount of a compound or composition, wherein the compound or composition inhibits growth and/or activity of one or more strains of bacteria from one or more species selected from the group consisting of *Akkermansia muciniphila, Bacteroides acidifaciens, Bifidobacterium animalis, Bifidobacterium pseudolongum, Desulfovibrio D168, Elizabethkingia meningoseptica, Escherichia coli, Lactobacillus reuteri, Mucispirillium schaedleri, Oxalobacter formigenes, Parabacteroides distasoni, Peptostreptococcus anaerobius, Prevotella melaninogenica, Prevotella stercorea, Pyramidobacter piscolens, Rothia mucilaginosa, Streptococcus anginosus*, and *Veillonella dispar* in the gastrointestinal (GI) microbiota of the subject. In certain embodiments, the compound or composition inhibits growth and/or activity of at least 2, 3, 4, 5, 6, 7, 8, 9, 10, 20, 50 or more strains from this taxa.

In one embodiment of any of the above methods of the invention, the compound or composition that inhibits growth and/or activity of one or more strains of bacteria is administered in a therapeutically effective amount. The dosages of the compound or composition administered in the methods of the invention will vary widely, depending upon the subject's physical parameters, the frequency of administration, the manner of administration, the clearance rate, and the like. The initial dose may be larger, and might be followed by smaller maintenance doses. The dose may be administered as infrequently as weekly or biweekly, or fractionated into smaller doses and administered daily, semiweekly, etc., to maintain an effective dosage level. It is contemplated that a variety of doses will be effective to reduce or eradicate colonization.

In some embodiments, the compound or composition that inhibits growth and/or activity of one or more strains of bacteria according to any of the above methods can be natural products that inhibit microbial growth. In certain embodiments, the compound or composition that inhibits growth and/or activity of one or more strains of bacteria according to any of the above methods can be bacteria that is conditionally lethal engineered bacteria (e.g., *H. Pylori, E. coli*, etc. . . . ). In certain embodiments, the compound or composition that inhibits growth and/or activity of one or more strains of bacteria according to any of the above methods can be genetically engineered commensals strains of microorganisms.

In some embodiments, suppressing growth or activity of at least one bacterial species in the microbiota according to any of the above methods involving such suppression can be achieved, e.g., by administering an antibiotic. In one specific embodiment, the antibiotic is administered in a therapeutic dose. In another specific embodiment, the antibiotic is administered in a sub-therapeutic dose. Non-limiting examples of antibiotics useful in the methods of the invention include beta-lactams (e.g., Penicillin VK, Penicillin G, Amoxicillin trihydrate), nitroimidazoles, macrolides (e.g., Tylosin tartrate, Erythromycin, Azithromycin, and Clarithromycin), tetracyclines, glycopeptides (e.g., Vancomycin), and fluoroquinolones. In one specific embodiment, the method comprises administering Penicillin VK or Penicillin G at 1 mg/kg body weight per day for at least four weeks of life. In another specific embodiment, the method comprises administering Amoxicillin trihydrate at 25 mg/kg body weight per day for 1 to 3 treatments each lasting 3 to 5 days. In yet another specific embodiment, the method comprises administering Tylosin tartrate at 50 mg/kg body weight per day for 1 to 3 treatments each lasting 3 to 5 days.

Formulations and Combination Treatments

Oral delivery may also include the use of nanoparticles that can be targeted, e.g., to the GI tract of the subject, such as those described in Yun et al., Adv Drug Deliv Rev. 2013, 65(6):822-832 (e.g., mucoadhesive nanoparticles, negatively charged carboxylate- or sulfate-modified particles, etc.). Non-limiting examples of other methods of targeting delivery of compositions to the GI tract are discussed in U.S. Pat. Appl. Pub. No. 2013/0149339 and references cited therein (e.g., pH sensitive compositions [such as, e.g., enteric polymers which release their contents when the pH becomes alkaline after the enteric polymers pass through the stomach], compositions for delaying the release [e.g., compositions which use hydrogel as a shell or a material which coats the active substance with, e.g., in vivo degradable polymers, gradually hydrolyzable polymers, gradually water-soluble polymers, and/or enzyme degradable polymers], bioadhesive compositions which specifically adhere to the colonic mucosal membrane, compositions into which a protease inhibitor is incorporated, a carrier system being specifically decomposed by an enzyme present in the colon).

For oral administration, the active ingredient(s) can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

In one aspect, the invention provides a method for treating (including preventing) pancreatic cancer or tumors in a subject in need thereof, said method comprising administering a compound or composition that inhibits growth and/or activity of one or more strains of bacteria (as disclosed above) in combination with administering a probiotic and/or a prebiotic composition that stimulates growth and/or activity of one or more strains of bacteria (as disclosed above). In certain embodiments, the compound or composition that inhibits growth and/or activity of one or more strains of bacteria is administered before the probiotic and/or prebiotic composition(s). In certain embodiments, the compound or composition that inhibits growth and/or activity of one or more strains of bacteria is administered after the probiotic and/or prebiotic composition(s). In certain embodiments, the compound or composition that inhibits growth and/or activity of one or more strains of bacteria is administered at the same time as the probiotic and/or prebiotic composition(s). In certain embodiment, the growth is inhibited to the extent that the bacterial strains are removed from the microbiota (i.e., reduced or ablated). In certain embodiments, the pancreatic cancer is pancreatic ductal adenocarcinoma (PDA). In certain embodiments, additional other therapeutic methods/agents (as disclosed below) can be co-administered (simultaneously or sequentially) with the combination inhibitory and stimulatory therapy to generate additive or synergistic effects.

It is also contemplated that when used to treat various pancreatic cancers or tumors, the compositions and methods of the present invention can be utilized with other therapeutic methods/agents suitable for the same or similar cancers or tumors. Such other therapeutic methods/agents can be co-administered (simultaneously or sequentially) to generate additive or synergistic effects. Suitable therapeutically effective dosages for each agent may be lowered due to the additive action or synergy.

In one embodiment of any of the above methods of the invention, the method further comprises administering to the subject one or more additional compounds selected from the group consisting of immuno-suppressives, biologicals, probiotics, prebiotics, and cytokines (e.g., IFN or IL-22).

In certain embodiments, the compositions can be administered with an effective amount of at least one programmed cell death protein 1 (PD-1) inhibitor. In certain embodiments, co-administration with a PD-1 inhibitor results in synergistic results (e.g., treatment of pancreatic cancer). In certain embodiments, the PD-1 inhibitor is an antibody. In certain embodiments, the PD-1 inhibitor antibody can be pembrolizumab or nivolumab.

As a non-limiting example, the invention can be combined with other therapies that block inflammation (e.g., via blockage of IL1, INFα/β, IL6, TNF, IL23, etc.).

The methods and compositions of the invention can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 41BB, OX40, etc.). The methods of the invention can be also combined with other treatments that possess the ability to modulate NKT function or stability, including but not limited to CD1d, CD1d-fusion proteins, CD1d dimers or larger polymers of CD1d either unloaded or loaded with antigens, CD1d-chimeric antigen receptors (CD1d-CAR), or any other of the five known CD1 isomers existing in humans (CD1a, CD1b, CD1c, CD1e).

Therapeutic methods of the invention can be combined with additional immunotherapies and therapies. For example, when used for treating cancer, the compositions of the invention can be used in combination with conventional cancer therapies, such as, e.g., surgery, radiotherapy, chemotherapy or combinations thereof, depending on type of the tumor, patient condition, other health issues, and a variety of factors. In certain aspects, other therapeutic agents useful for combination cancer therapy with the inhibitors of the invention include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000). In one embodiment, the compositions of the invention can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab).

Non-limiting examples of chemotherapeutic compounds which can be used in combination treatments of the present invention include, for example, abraxane, aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, folfirinox, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine. In certain embodiments, the chemotherapeutic can be folfirinox, gemcitabine, abraxane, or a combination thereof.

These chemotherapeutic compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In certain embodiments, a conditional lethal bacterial strain can be utilized as the inoculant or to deliver a recombinant construct. Such a conditional lethal bacteria survives for a limited time typically when provided certain nutritional supplements. It is contemplated that such a supplement could be a liquid, formulated to contain the nutritional component necessary to keep the bacteria alive. It is further contemplated that a patient/subject would drink such a supplement in intervals to keep the bacteria alive. Once the supplement is depleted, the conditional lethal bacteria die. Methods relating to conditional lethal strains of *H. pylori* are described in U.S. Pat. No. 6,570,004.

Spores used in the compositions of the invention can be isolated, for example, by solvent treatments (e.g., using partially miscible, fully miscible or an immiscible solvent), chromatographic treatments (e.g., using hydrophobic interaction chromatography (HIC) or an affinity chromatography), mechanical treatments (e.g., blending, mixing, shaking, vortexing, impact pulverization, and sonication), filtration treatments, thermal treatments (e.g., 30 seconds in a 100° C. environment followed by 10 minutes in a 50° C.), irradiation treatments (e.g., with ionizing radiation, typically gamma irradiation, ultraviolet irradiation or electron beam irradiation provided at an energy level sufficient to kill pathogenic materials while not substantially damaging the desired spore populations), centrifugation and density separation treatments (e.g., using density or mobility gradients or cushions (e.g., step cushions), such as, e.g., CsCl, Percoll, Ficoll, Nycodenz, Histodenz or sucrose gradients). It is generally desirable to retain the spore populations under non-germinating and non-growth promoting conditions and media, in order to minimize the growth of pathogenic bacteria present in the spore populations and to minimize the germination of spores into vegetative bacterial cells.

The compositions of the invention can comprise a carrier and/or excipient. While it is possible to use a bacterial inoculant or compound of the present invention for therapy as is, it may be preferable to administer it in a pharmaceutical formulation, e.g., in admixture with a suitable pharmaceutical excipient and/or carrier selected with regard to the intended route of administration and standard pharmaceutical practice. The excipient and/or carrier must be "acceptable" in the sense of being compatible with the other ingredients of the formulation and not deleterious to the recipient thereof. Acceptable excipients and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient and carrier can be selected with regard to the intended route of administration and standard pharmaceutical practice. Oral formulations readily accommodate additional mixtures, such as, e.g., milk, yogurt, and infant formula. Solid dosage forms for oral administration can also be used and can include, e.g., capsules, tablets, caplets, pills, troches, lozenges, powders, and granules. Non-limiting examples of suitable excipients include, e.g., diluents, buffering agents (e.g., sodium bicarbonate, infant formula, or other agents which allow bacteria to survive and grow [e.g., survive in the acidic environment of the stomach and to grow in the intestinal environment]), preservatives, stabilizers, binders, compaction agents, lubricants, dispersion enhancers, disintegration agents, antioxidants, flavoring agents, sweeteners, and coloring agents. Additional specific examples of suitable carriers and/or excipients include, e.g., vegetable cellulose, vegetable stearic acid, vegetable magnesium stearate, and/or silica. Those of relevant skill in the art are well able to prepare suitable solutions.

Diagnostic Methods of the Invention

In one embodiment, the present invention provides a method for diagnosing predisposition to pancreatic cancer or tumors in a subject, said method comprising a) determining the level of (i) at least one strain of the bacteria of Table 1 or a closely related OTU which has at least 90% (or at least 95%, or at least 97%, or at least 99%) sequence identity to 16S rRNA over its entire length or has at least 90% (or at least 95%, or at least 99%) sequence identity to any single V region of 16S rRNA in the gastrointestinal (GI) or pancreatic microbiota of the subject and/or (ii) at least one strain of the bacteria of Table 2 or a closely related OTU which has at least 90% (or at least 95%, or at least 97%, or at least 99%) sequence identity to 16S rRNA over its entire length or has at least 90% (or at least 95%, or at least 99%) sequence identity to any single V region of 16S rRNA in the gastrointestinal (GI) or pancreatic microbiota of the subject, and (b) comparing the level determined in step (a) to the level of the same bacteria in the gastrointestinal or pancreatic microbiota of healthy controls, and (c) identifying that the subject is predisposed to pancreatic cancer or tumors and/or associated conditions wherein the level of at least one of the strains measured in step (a.i.) is lower (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% lower) than in healthy controls and/or the level of at least one of the strains measured in step (a.ii.) is higher (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% higher) than in healthy controls. In certain embodiments, the pancreatic cancer is pancreatic ductal adenocarcinoma (PDA).

In certain embodiments, the level of at least 2, 3, 4, 5, 6, 7, 8, 9, 10, 20, 50 or more strains from the taxa listed in Table 1 and/or Table 2 is determined. In certain embodiments, the level of at least 2, 3, 4, 5, 6, 7, 8, 9, 10, 20, 50 or more strains from the taxa listed in Table 1 and/or Table 2 is determined and compared to the same bacteria in a healthy control.

In certain embodiments, rather than comparing with a healthy subject, the bacteria level is compared to an earlier sample taken from the same subject. The sample could be taken before or after treatment. The sample could be taken before or after symptoms of a disease or cancer.

In certain embodiments, the presence of at least one strain of *Elizabethkingia meningoseptica, Bacteroides acidifaciens, Mucispirillum schaedleri, Bifidobacterium pseudolongum* can be indicative of early stage pancreatic cancer. In certain embodiments, the pancreatic cancer is PDA. In certain embodiments, the at least one strain of *Elizabethkingia meningoseptica, Bacteroides acidifaciens, Mucispirillum schaedleri,* or *Bifidobacterium pseudolongum* is found in cecal, ileal, colonic, and fecal microbiota. In certain embodiments, the at least one strain of *Elizabethkingia meningoseptica, Bacteroides acidifaciens, Mucispirillum schaedleri, Bifidobacterium pseudolongum* is found in fecal microbiota.

In certain embodiments, the presence of at least one strain of *Elizabethkingia meningoseptica, Bacteroides acidifaciens, Mucispirillum schaedleri, Bifidobacterium pseudolongum,* or *Lactobacillus reuteri* can be indicative of late stage pancreatic cancer. In certain embodiments, the pancreatic cancer is PDA. In certain embodiments, the at least one strain of *Elizabethkingia meningoseptica, Bacteroides acidifaciens, Mucispirillum schaedleri, Bifidobacterium pseudolongum* or *Lactobacillus reuteri* is found in cecal, ileal, colonic, and fecal microbiota. In certain embodiments, the at least one strain of *Elizabethkingia meningoseptica, Bacteroides acidifaciens, Mucispirillum schaedleri, Bifidobacterium pseudolongum* or *Lactobacillus reuteri* is found in fecal microbiota.

Non-limiting examples of the methods which can be used for determining the relative abundance of the bacterial strains include, e.g., quantitative polymerase chain reaction (qPCR), sequencing of bacterial 16S rRNA, shotgun metagenome sequencing, bacterial genotype pattern based fingerprinting (DNA fingerprinting) and metabolomics.

Additional methods include methods of evaluating the microbiota population in a subject or diagnosing an abnormal microbiota development. Methods include monitoring the subject's microbiota after the administration of the microbiota inoculum or probiotic by: (a) determining a relative abundance of one or more bacterial taxa in a microbiota sample obtained from the subject, and (b) comparing the relative abundance(s) determined in step (a) to (i) a predetermined standard value or (ii) to the abundance(s) of the same taxa in a control subject or (iii) to the average value of abundances of the same taxa in several control subjects. The subject's sample may be isolated from feces, skin, intestines, intestinal mucosa, oral mucosa, conjunctive mucosa, or nasal mucosa. It may be compared to a control subject.

The determination of relative abundance of the taxa may involve, for example, a method selected from the group consisting of quantitative polymerase chain reaction (qPCR), sequencing of bacterial 16S rRNA, shotgun metagenome sequencing, bacterial genotype pattern based fingerprinting (DNA fingerprinting), and metabolomic analysis.

In accordance with the present invention there may be numerous tools and techniques within the skill of the art, such as those commonly used in molecular biology, pharmacology, and microbiology. Such tools and techniques are described in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Figure 5A:
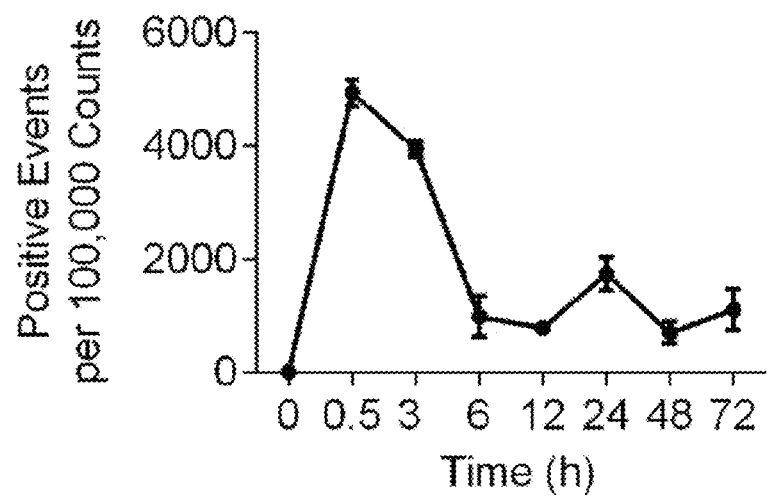
FIGS. 5A-5C. Luminal bacteria can access the pancreas, and human PDA harbors a distinct microbiome. (5A) WT mice were administered CFSE-labeled *Enterococcus faecalis* (2×10$^8$ CFU) via oral gavage. Pancreata were harvested and digested at timed intervals and tested for the presence of these bacteria (n=3 mice/time point). This experiment was repeated twice with similar results. (5B) Taxonomic composition of microbiota assigned to phylum level in pancreatic tumors of PDA patients based on average percent relative abundance determined by 16S sequencing (n=12). (5C) Heatmap of the top 40 genera in the bacterial communities in pancreatic tumors of PDA patients. The relative abundance of bacterial genera are indicated by the color gradient from low (blue) to high (orange). Double hierarchical linkage clustering of the samples was based on microbial composition and abundance.

Example 1. Determining the Ability of Bacteria to Access the Pancreas and Affect Pancreatic Oncogenesis To determine whether endoluminal gut bacteria can access the pancreas, fluorescently-labeled *Enterococcus faecalis* was administered to wild-type (WT) mice via oral gavage. A substantial fraction of bacteria migrated into the pancreas, demonstrating that intestinal bacteria can directly influence the pancreatic microenvironment (FIG. 5A).

Figure 5B:
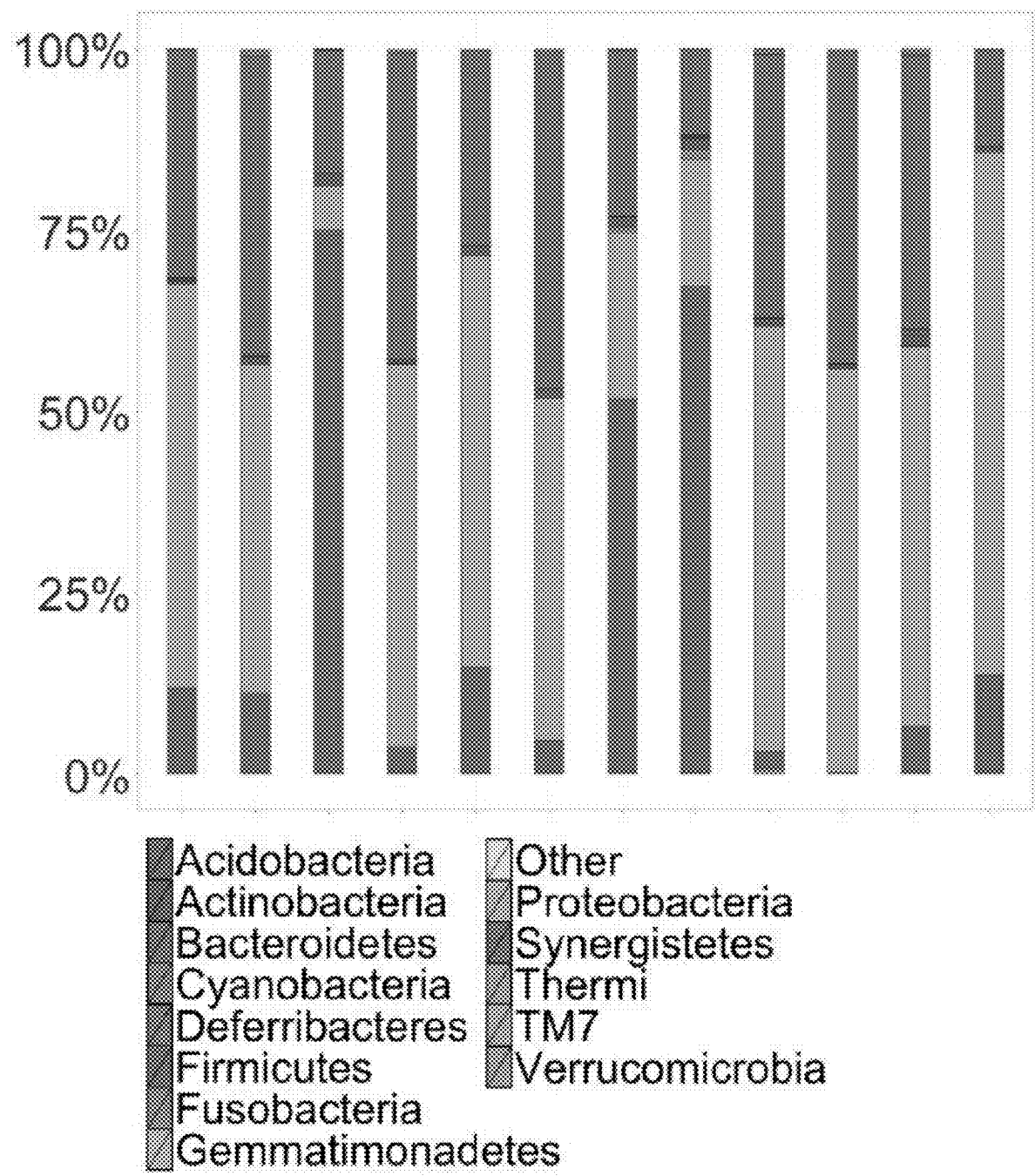
Figure 5C:
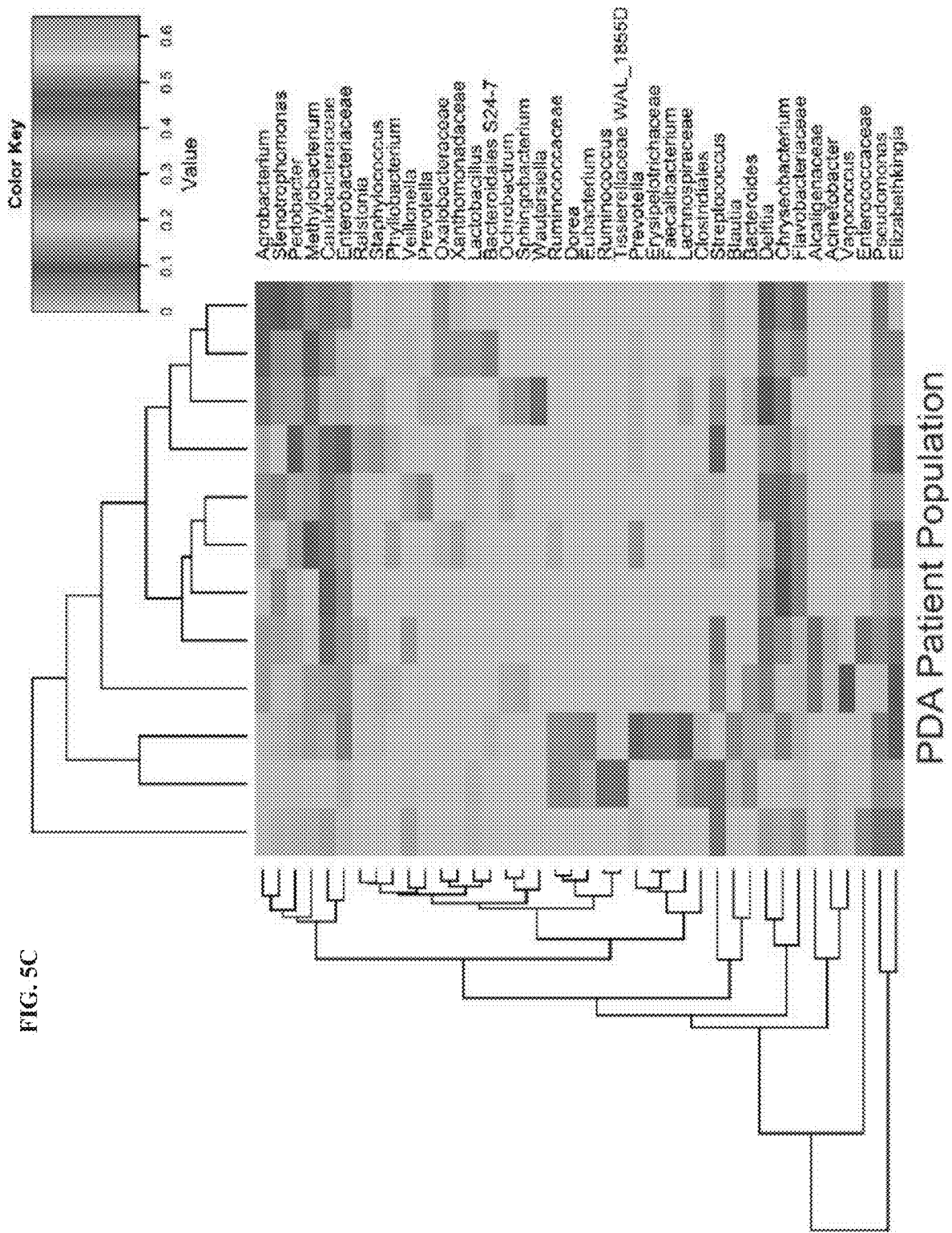

To determine whether an intra-pancreatic microbiome is present in human PDA, 16S gene sequencing was performed on pancreatic tumors from 12 PDA patients. Fourteen distinct phyla were detected in human PDA tumors. *Proteobacteria* (45%), *Bacteroidetes* (31%) and *Firmicutes* (22%) were most abundant and were prevalent in all samples (FIG. 5B). *Actinobacteria* (1%) were also prevalent in all samples whereas *Fusobacteria* (<1%) were detected only in 25% of the patient population. On the genus level, *Pseudomonas* and *Elizabethkingia* constituted up to 33% of the total microbial community and were prevalent in all human PDA specimens (FIG. 5C). *Enterobacteriaceae*, *Caulobacteraceae*, *Chryseobacterium*, *Enterococcaceae*, *Flavobacteri-* aceae, *Streptococcus* and *Delftia* were in the range of 3%-6% abundance with >80% prevalence (FIG. 5C). Collectively, these data suggest a distinct pancreatic microbiome in PDA. Table 3 below lists the bacterial phyla and genera found common and unique to GI tract and pancreas of nine human pancreatic cancer patients.

TABLE 3

Bacterial phyla and genera found common and unique to GI tract and Pancreas of nine human pancreatic cancer patients

| Phylum; Genus Common in Fecal and Pancreas | Phylum; Genus Unique to Fecal | Phylum; Genus Unique to Pancreas |
|---|---|---|
| Actinobacteria; *Actinomyces* | Actinobacteria; *Actinobaculum* | Acidobacteria; *Chloracidobacteria* PK29 |
| Actinobacteria; *Arcanobacterium* | Actinobacteria; *Adlercreutzia* | Actinobacteria; Actinomycetaceae |
| Actinobacteria; *Atopobium* | Actinobacteria; Bifidobacteriaceae | Actinobacteria; *Arthrobacter* |
| Actinobacteria; *Bifidobacterium* | Actinobacteria; *Collinsella* | Actinobacteria; *Cryocola* |
| Actinobacteria; Coriobacteriaceae | Actinobacteria; *Dermabacter* | Actinobacteria; *Kocuria* |
| Actinobacteria; *Corynebacterium* | Actinobacteria; *Eggerthella* | Actinobacteria; *Leucobacter* |
| Actinobacteria; *Microbacterium* | Actinobacteria; *Micrococcus* | Actinobacteria; Microbacteriaceae |
| Actinobacteria; *Rothia* | Actinobacteria; *Mobiluncus* | Actinobacteria; *Mycobacterium* |
| Bacteroidetes; Bacteroidales | Actinobacteria; *Nesterenkonia* | Actinobacteria; Nocardioidaceae |
| Bacteroidetes; Bacteroidales S24-7 | Actinobacteria; *Pseudoclavibacter* | Actinobacteria; Propionibacteriaceae |
| Bacteroidetes; *Bacteroides* | Actinobacteria; *Slackia* | Actinobacteria; *Propionibacterium* |
| Bacteroidetes; *Elizabethkingia* | Actinobacteria; *Trueperella* | Actinobacteria; *Rhodococcus* |
| Bacteroidetes; Flavobacteriaceae | Actinobacteria; Unclassified_Actinomycetaceae | Actinobacteria; *Saccharopolyspora* |
| Bacteroidetes; *Odoribacter* | Actinobacteria; Unclassified_Bifidobacteriaceae | Actinobacteria; Unclassfied_Bifidobacteriaceae |
| Bacteroidetes; *Parabacteroides* | Actinobacteria; *Varibaculum* | Actinobacteria; Unclassified_Actinomycetales |
| Bacteroidetes; *Paraprevotella* | Bacteroidetes; Bacteroidales RF16 | Actinobacteria; *Williamsia* |
| Bacteroidetes; *Pedobacter* | Bacteroidetes; Barnesiellaceae | Bacteroidetes; *Capnocytophaga* |
| Bacteroidetes; *Porphyromonas* | Bacteroidetes; *Butyricimonas* | Bacteroidetes; *Chryseobacterium* |
| Bacteroidetes; *Prevotella* | Bacteroidetes; Chitinophagaceae | Bacteroidetes; *Cloacibacterium* |
| Bacteroidetes; *Rikenella* | Bacteroidetes; Unclassified_Bacteroidales | Bacteroidetes; *Flavobacterium* |
| Bacteroidetes; Rikenellaceae | Bacteroidetes; Unclassified_Barnesiellaceae | Bacteroidetes; *Larkinella* |
| Cyanobacteria; *Streptophyta* | Bacteroidetes; Unclassified_Rikenellaceae | Bacteroidetes; *Sphingobacterium* |
| Firmicutes; *Anaerococcus* | Firmicutes; *Abiotrophia* | Bacteroidetes; *Wautersiella* |
| Firmicutes; *Bacillus* | Firmicutes; *Acidaminococcus* | Bacteroidetes; *Prevotella* |
| Firmicutes; *Blautia* | Firmicutes; *Anaerofustis* | Deferribacteres; *Mucispirillum* |
| Firmicutes; Christensenellaceae | Firmicutes; *Anaerostipes* | Firmicutes; Aerococcaceae |
| Firmicutes; Clostridiaceae | Firmicutes; *Anaerotruncus* | Firmicutes; *Aerococcus* |
| Firmicutes; Clostridiales | Firmicutes; *Bulleidia* | Firmicutes; *Allobaculum* |
| Firmicutes; *Clostridium* | Firmicutes; *Catenibacterium* | Firmicutes; Bacillaceae |
| Firmicutes; *Coprococcus* | Firmicutes; *Christensenella* | Firmicutes; *Candidatus* |
| Firmicutes; *Dialister* | Firmicutes; *Clostridiaceae* SMB53 | Firmicutes; *Lysinibacillus* |
| Firmicutes; *Dorea* | Firmicutes; *Coprobacillus* | Firmicutes; *Pseudoramibacter* (*Eubacterium*) |
| Firmicutes; Enterococcaceae | Firmicutes; *Dehalobacterium* | Firmicutes; *Tissierella_Soehngenia* |
| Firmicutes; *Enterococcus* | Firmicutes; *Epulopiscium* | Firmicutes; Unclassfied_Enterococcaceae |
| Firmicutes; Erysipelotrichaceae | Firmicutes; Erysipelotrichaceae cc_115 | Firmicutes; Unclassfied_Lactobacillales |
| Firmicutes; *Eubacterium* | Firmicutes; *Filifactor* | Firmicutes; *Vagococcus* |
| Firmicutes; *Facklamia* | Firmicutes; *Gallicola* | Gemmatimonadetes; Gemmatimonadetes Gemm-3 |
| Firmicutes; *Faecalibacterium* | Firmicutes; *Gemella* | OD1; OD1 ZB2 |
| Firmicutes; *Finegoldia* | Firmicutes; Gemellaceae | Proteobacteria; Alcaligenaceae |
| Firmicutes; *Granulicatella* | Firmicutes; *Helcococcus* | Proteobacteria; Alphaproteobacteria |
| Firmicutes; *Holdemania* | Firmicutes; *Lachnobacterium* | Proteobacteria; Bradyrhizobiaceae |
| Firmicutes; *Lachnospira* | Firmicutes; Leuconostocaceae | Proteobacteria; *Brevundimonas* |
| Firmicutes; Lachnospiraceae | Firmicutes; *Megasphaera* | Proteobacteria; *Comamonas* |
| Firmicutes; Lactobacillales | Firmicutes; *Mogibacterium* | Proteobacteria; *Curvibacter* |
| Firmicutes; *Lactobacillus* | Firmicutes; *Moryella* | Proteobacteria; *Enhydrobacter* |
| Firmicutes; *Lactococcus* | Firmicutes; *Oribacterium* | Proteobacteria; Helicobacteraceae |
| Firmicutes; *Leuconostoc* | Firmicutes; *Oscillospira* | Proteobacteria; *Hydrogenophaga* |
| Firmicutes; Mogibacteriaceae | Firmicutes; *Peptococcus* | Proteobacteria; *Hydrogenophilus* |
| Firmicutes; *Parvimonas* | Firmicutes; Peptostreptococcaceae | Proteobacteria; *Hyphomicrobium* |
| Firmicutes; Peptococcaceae | Firmicutes; *Peptostreptococcus* | Proteobacteria; *Luteimonas* |
| Firmicutes; *Peptoniphilus* | Firmicutes; *Phascolarctobacterium* | Proteobacteria; *Mesorhizobium* |
| Firmicutes; Ruminococcaceae | Firmicutes; Planococcaceae | Proteobacteria; Methylobacteriaceae |
| Firmicutes; *Ruminococcus* | Firmicutes; *Pseudoramibacter_Eubacterium* | Proteobacteria; *Neisseria* |
| Firmicutes; *Staphylococcus* | Firmicutes; *Roseburia* | Proteobacteria; Nitrosomonadaceae |
| Firmicutes; *Streptococcus* | Firmicutes; *Selenomonas* | Proteobacteria; *Novosphingobium* |
| Firmicutes; Tissierellaceae WAL_1855D | Firmicutes; *Succiniclasticum* | Proteobacteria; Oxalobacteraceae |
| Firmicutes; Tissierellaceae ph2 | Firmicutes; Tissierellaceae | Proteobacteria; *Phyllobacterium* |
| Firmicutes; Unclassified_Clostridiales | Firmicutes; Tissierellaceae 1-68 | Proteobacteria; Pseudomonadaceae |
| Firmicutes; Unclassified_Erysipelotrichaceae | Firmicutes; Tissierellaceae GW-34 | Proteobacteria; Rhizobiales |
| Firmicutes; *Veillonella* | Firmicutes; *Turicibacter* | Proteobacteria; *Rhodoplanes* |
| Fusobacteria; *Fusobacterium* | Firmicutes; Unclassfied_Clostridiaceae | Proteobacteria; Rhodospirillaceae |
| Proteobacteria; *Achromobacter* | Firmicutes; Unclassified_Aerococcaceae | Proteobacteria; Rickettsiales |
| Proteobacteria; *Acinetobacter* | Firmicutes; Unclassified_Bacillales | Proteobacteria; *Sphingomonas* |
| Proteobacteria; Aeromonadaceae | Firmicutes; Unclassified_Enterococcaceae | Proteobacteria; Unclassified_Alcaligenaceae |
| Proteobacteria; *Agrobacterium* | Firmicutes; Unclassified_Gemellaceae | Proteobacteria; Unclassified_Comamonadaceae |
| Proteobacteria; *Bilophila* | Firmicutes; Unclassified_Lachnospiraceae | Proteobacteria; Unclassified_Helicobacteraceae |
| Proteobacteria; Caulobacteraceae | Firmicutes; Unclassified_Lactobacillales | Proteobacteria; Unclassified_Phyllobacteriaceae |
| Proteobacteria; *Citrobacter* | Firmicutes; Unclassified_Peptostreptococcaceae | Proteobacteria; Unclassified_Pseudomonadales |
| Proteobacteria; Comamonadaceae | Firmicutes; Unclassified_Ruminococcaceae | Proteobacteria; Xanthomonadaceae |
| Proteobacteria; *Delftia* | Firmicutes; Unclassified_Veillonellaceae | Synergistetes; Unclassified_Synergistaceae |

TABLE 3-continued

Bacterial phyla and genera found common and unique to GI tract and Pancreas of nine human pancreatic cancer patients

| Phylum; Genus Common in Fecal and Pancreas | Phylum; Genus Unique to Fecal | Phylum; Genus Unique to Pancreas |
|---|---|---|
| Proteobacteria; *Devosia* | Firmicutes; Veillonellaceae | TM7; TM7-3 EW055 |
| Proteobacteria; Enterobacteriaceae | Fusobacteria; *Leptotrichia* | Thermi; *Deinococcus* |
| Proteobacteria; *Erwinia* | Lentisphaerae; Victivallaceae | Thermi; *Thermus* |
| Proteobacteria; *Escherichia* | Proteobacteria; *Aggregatibacter* | Verrucomicrobia; Verrucomicrobiaceae MSBL3 |
| Proteobacteria; *Haemophilus* | Proteobacteria; Alphaproteobacteria RF32 | |
| Proteobacteria; *Klebsiella* | Proteobacteria; *Campylobacter* | |
| Proteobacteria; *Methylobacterium* | Proteobacteria; *Cardiobacterium* | |
| Proteobacteria; *Ochrobactrum* | Proteobacteria; *Desulfovibrio* | |
| Proteobacteria; *Pseudomonas* | Proteobacteria; *Eikenella* | |
| Proteobacteria; *Ralstonia* | Proteobacteria; *Enterobacter* | |
| Proteobacteria; *Serratia* | Proteobacteria; *Lautropia* | |
| Proteobacteria; *Stenotrophomonas* | Proteobacteria; Neisseriaceae | |
| Proteobacteria; *Sutterella* | Proteobacteria; *Oxalobacter* | |
| Proteobacteria; Unclassified_Enterobacteriaceae | Proteobacteria; *Proteus* | |
| Proteobacteria; Unclassified_Pseudomonadaceae | Proteobacteria; *Trabulsiella* | |
| Synergistetes; *Pyramidobacter* | Proteobacteria; Unclassified_Neisseriaceae | |
| TM7; TM7-3 CW040 | Proteobacteria; Unclassified_Oxalobacteraceae | |
| TM7; TM7-3 F16 | Proteobacteria; Unclassified_Proteobacteria | |
| Tenericutes; Mollicutes RF39 | Synergistetes; *Jonquetella* | |
| Unassigned | Synergistetes; Synergistaceae | |
| Verrucomicrobia; *Akkermansia* | TM7; TM7-3 | |
| | Tenericutes; | |
| | Tenericutes ML615J-28 | |

Figure 1B:
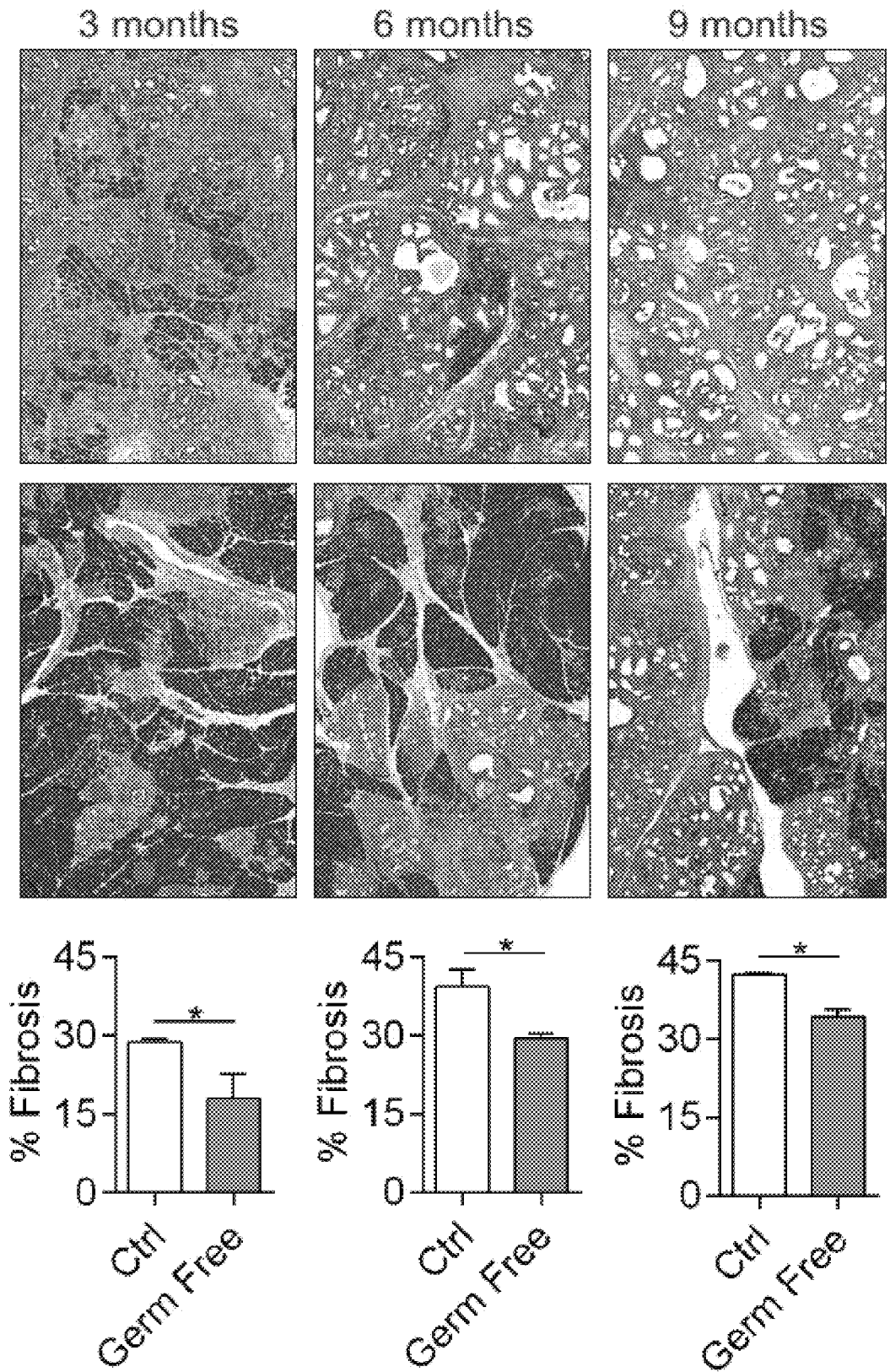
Figure 1C:
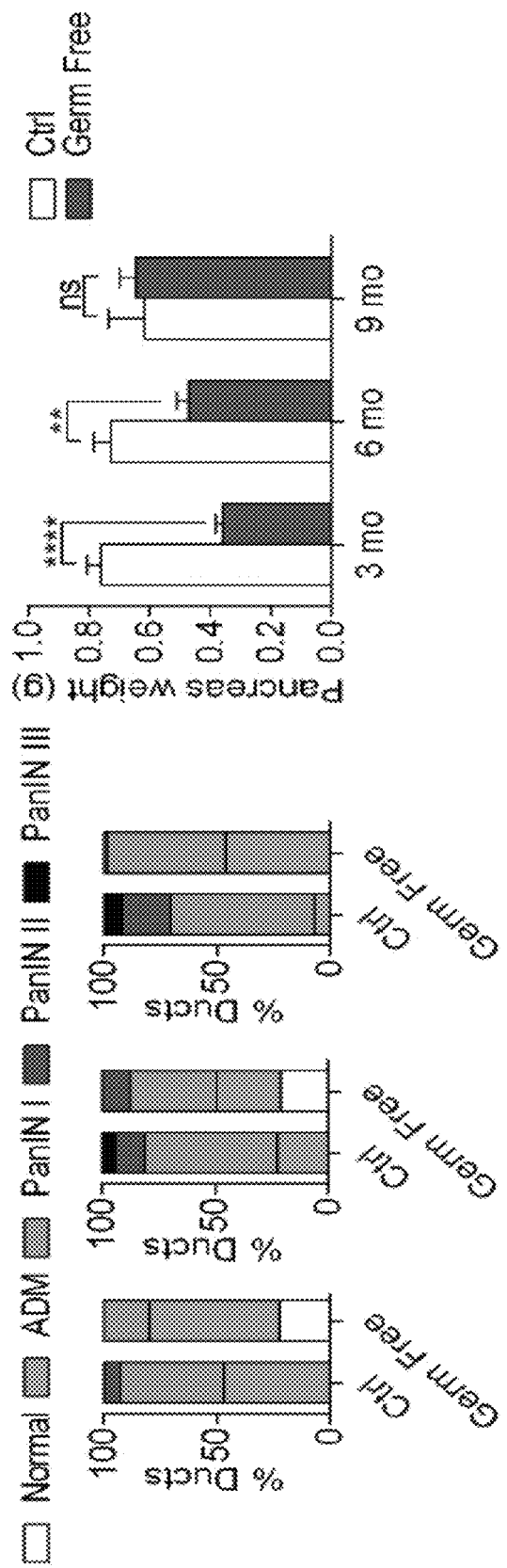
Figure 1D:
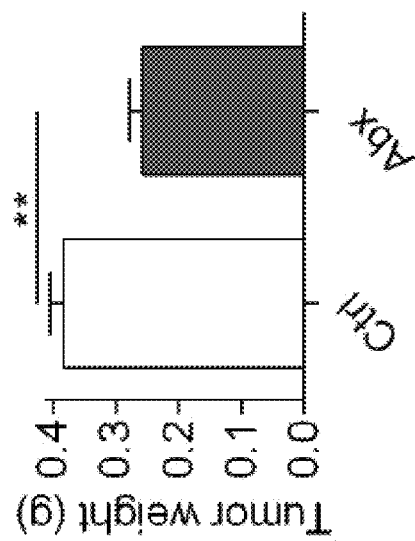

To determine whether bacteria promote the progression of pancreatic oncogenesis, the inventors employed the slowly progressive p48$^{Cre}$;LSL-Kras$^{G12D}$ (KC) mouse model of PDA[7] (New York University). KC mice were re-derived in a germ-free environment. Germ-free KC mice were protected against PDA progression and stromal expansion. Compared to age-matched control KC mice, germ-free cohorts exhibited delayed acinar effacement, reduced pancreatic dysplasia, diminished peri-tumoral fibrosis, and lower pancreatic weights (FIG. 1A-1C). Similarly, mice treated with an ablative oral antibiotic regimen developed significantly reduced tumor burdens in an invasive orthotopic PDA model using Pdx1$^{Cre}$;LsL-Kras$^{G12D}$;p53R$^{172H}$ (KPC)-derived tumor cells[12] (New York University) (FIG. 1D). These data imply that bacteria promote the progression of oncogene-driven PDA tumors.

Figure 2A:
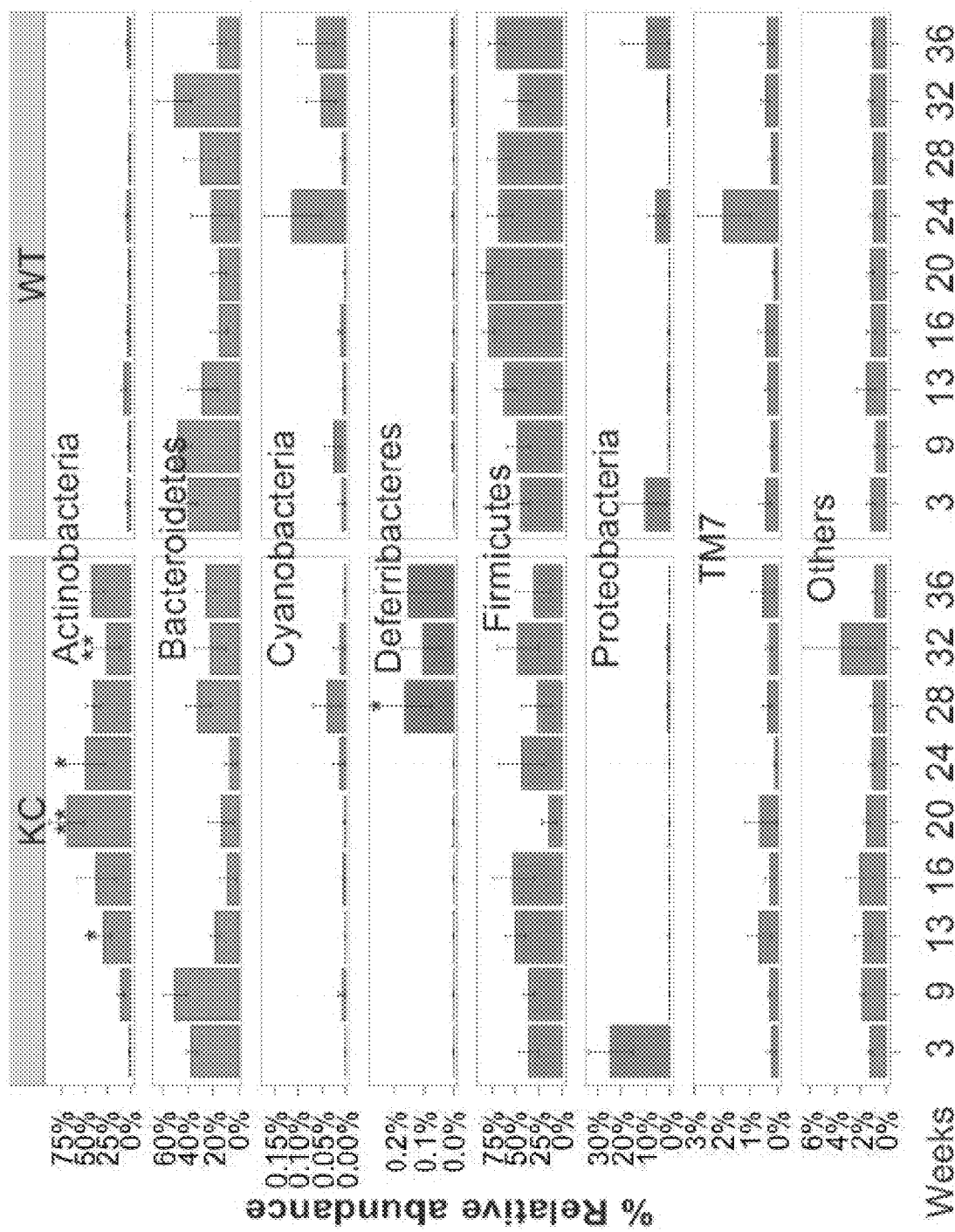
FIGS. 2A-2D. Temporal analysis of alterations in the microbiome during murine pancreatic oncogenesis. (2A) Taxonomic distribution of microbial phyla in the GI tract of KC and WT mice over time is shown (n=5/cohort; **$p<0.01$; *$p<0.05$). (2B) LDA analysis identified differentially abundant taxa in KC (red bars) and WT (green bars) cohorts. (2C) PCoA of gut bacterial community structure in each KC (red) and WT (blue) specimen based on their weighted UniFrac distance matrix is shown. The symbols indicate the age (in weeks) at which fecal specimens were collected. Axes indicate percentage of variation. (2D) Weighted PCoA analysis of gut microbial communities in KC and WT cohorts over time. Each point with a distinct symbol corresponds to abundances of genera in a given cohort at a particular time point. The ellipses are at 95% CI.
Figure 2B:
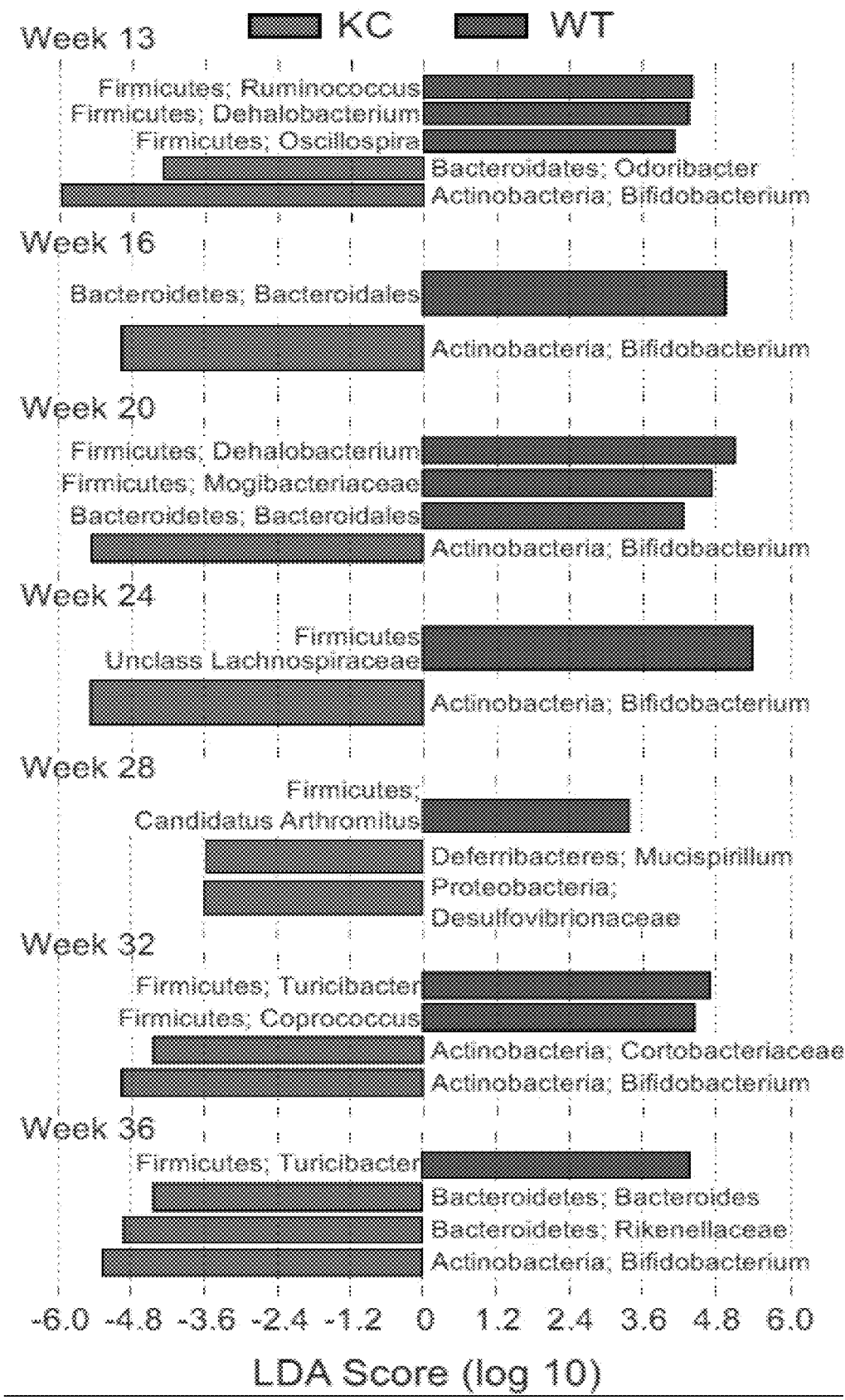
Figure 2C:
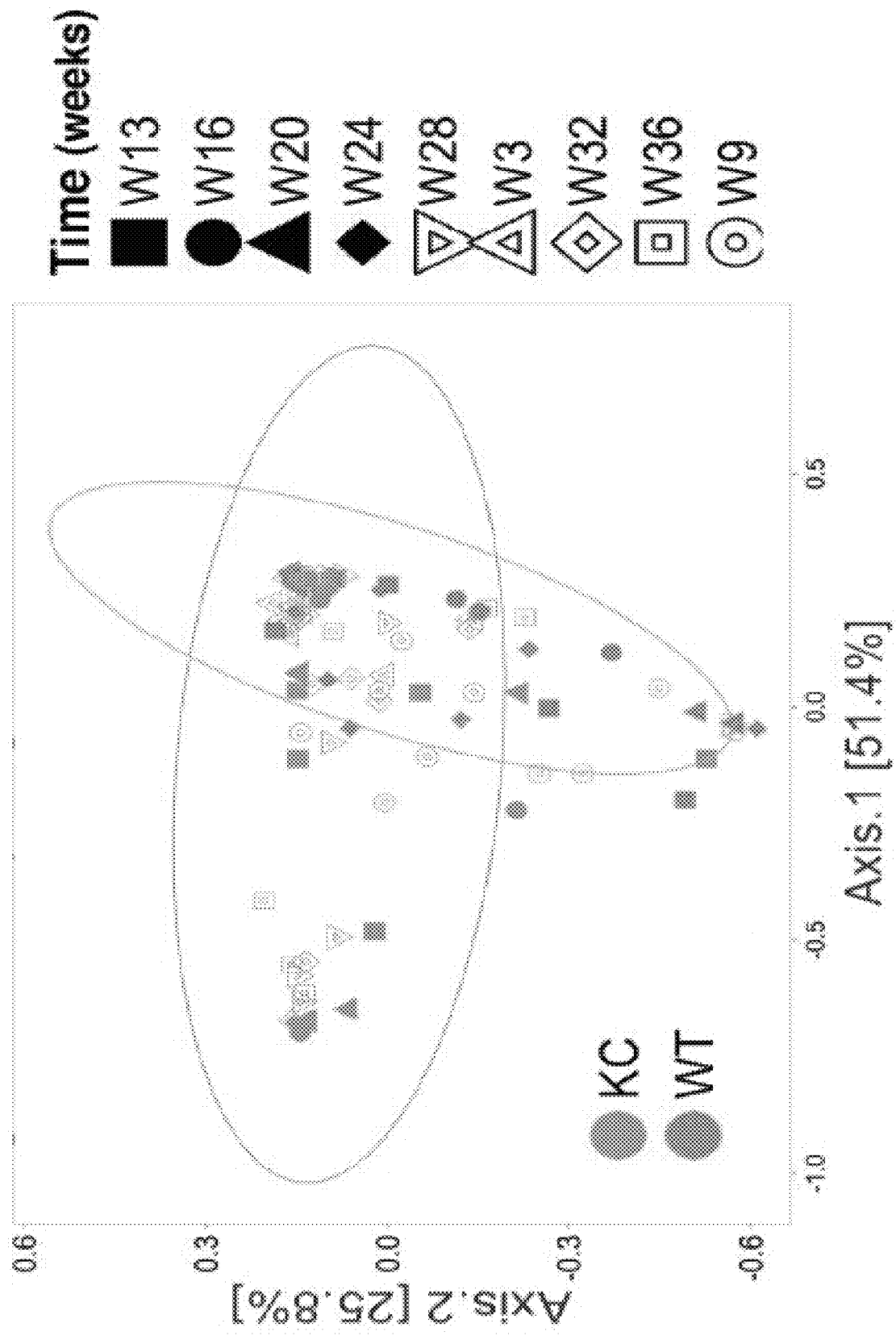
Figure 2D:
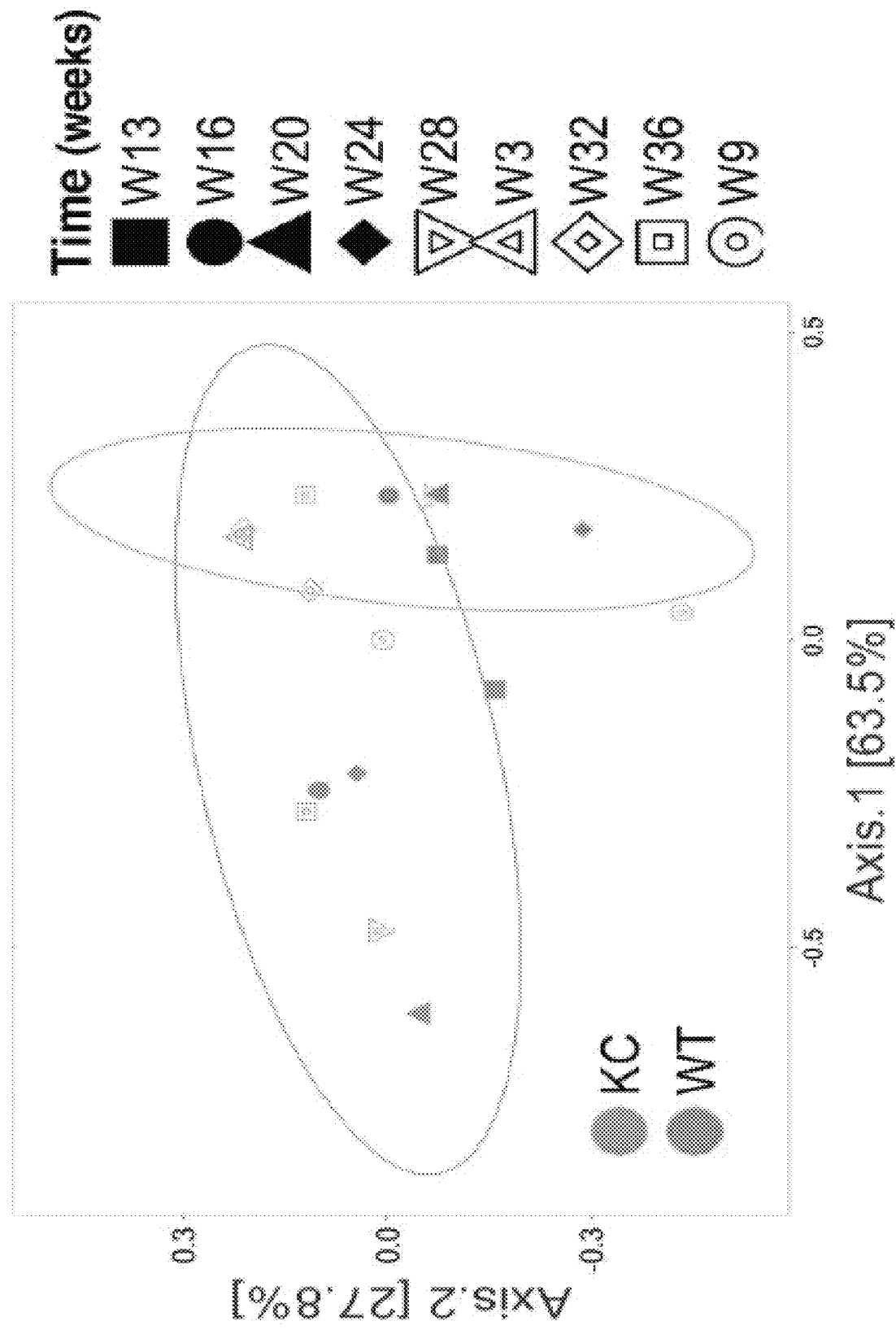
Figure 6:
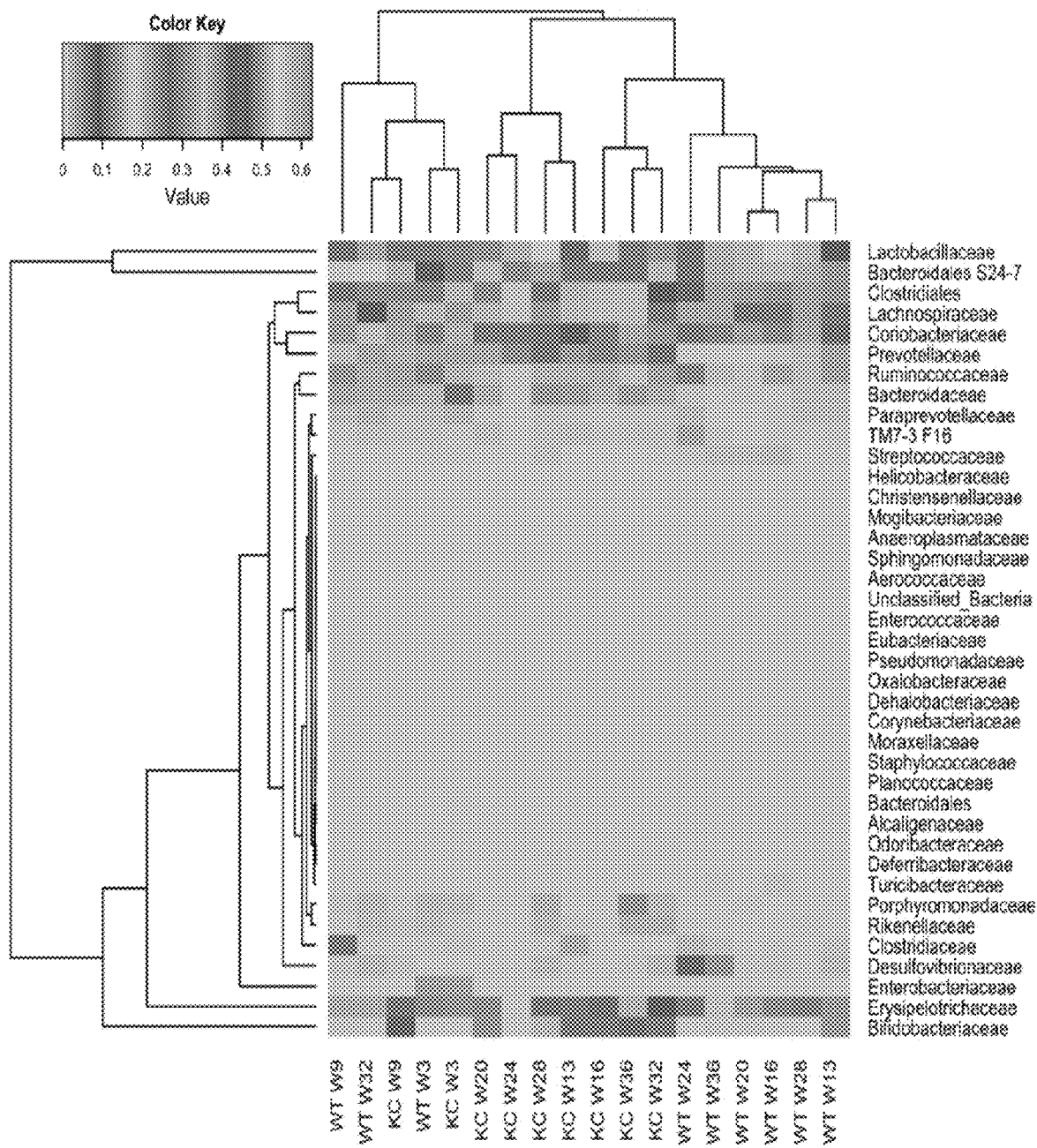
FIG. 6. Gut bacterial families become distinct in WT and KC mice during oncogenic progression. Heat-map showing top 40 families in gut bacterial communities in WT and KC mice (n=5/group) from week 3 to week 36 of life at 4-6 week intervals. Double hierarchical linkage clustering of the cohorts was based on composition (y-axis) and abundance (x-axis) of gut microbial communities. Abundances are shown on a log scale as averages and are indicated by the color gradient from low (blue) to high (orange). The dendrogram on the x-axis indicates the distinct clusters of each cohort.
Figure 7:
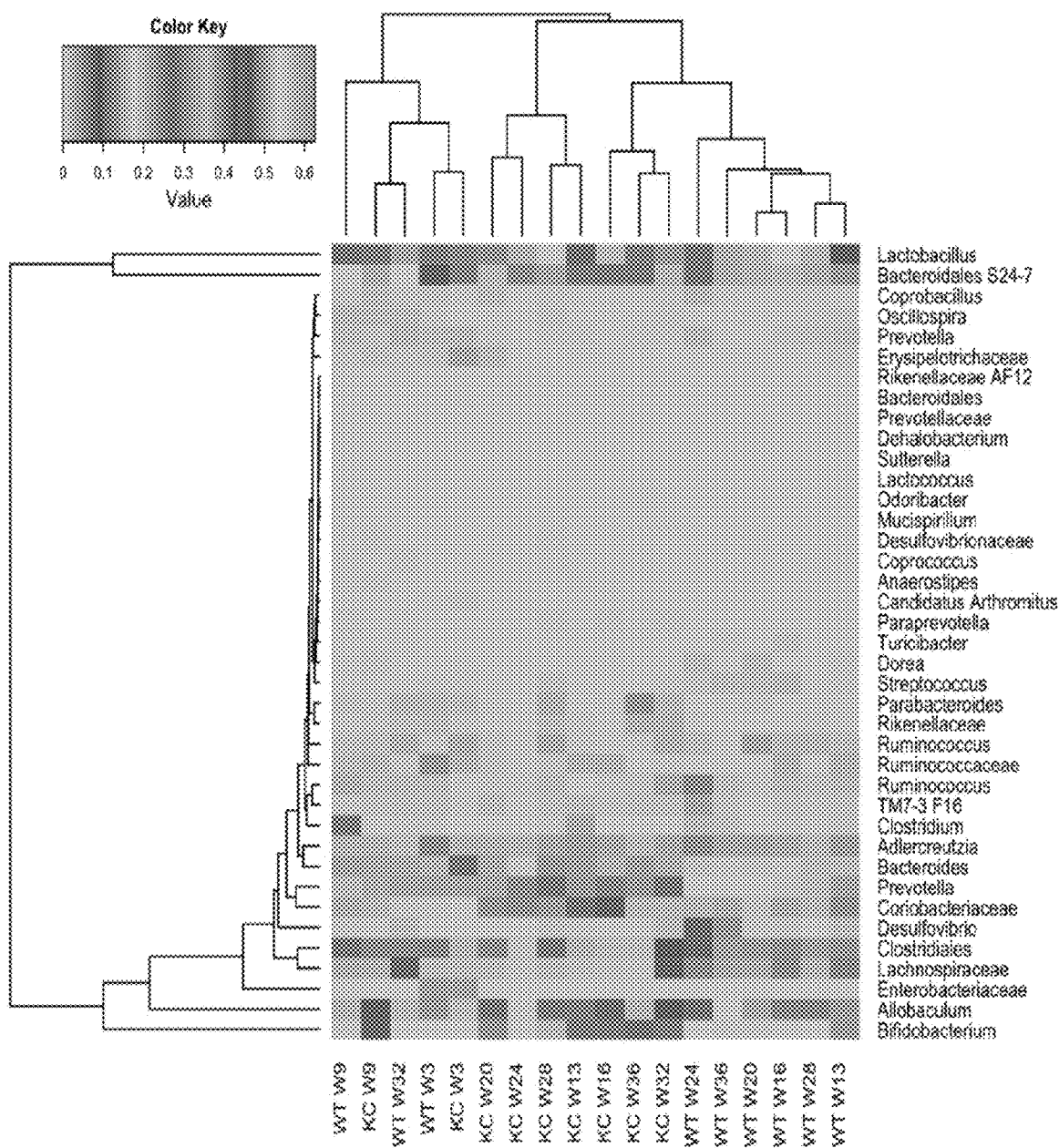
FIG. 7. Gut bacterial genera become distinct in WT and KC mice during oncogenic progression. Heat-map of top 40 genera showing longitudinal gut microbial diversity from week 3 to week 36 in KC and WT mice (n=5/group). Double hierarchical linkage clustering of the cohorts was based on composition (y-axis) and abundance (x-axis) of gut microbiota. Abundances are shown on a log scale as averages and are indicated by the color gradient from low (blue) to high (orange). The dendrogram on the x-axis indicates the distinct clusters of each cohort.

To identify possible perturbations in the gut microbiome associated with the progressive pancreatic oncogenesis, the inventors performed longitudinal analysis of the composition of the gut microbial community of KC mice compared with age-matched WT littermate controls (pC57BL/6 (H-2Kb) mice (Jackson Labs, Bar Harbor, Me.). Fecal bacterial profiles in KC and WT mice were interrogated over a period of nine months at intervals of 4-6 weeks using 16S gene sequencing. Early in murine life, the bacterial community structures in KC and WT cohorts were similar at the phylum level (FIG. 2A). Analogous to the communities in human PDA tumors, *Bacteroidetes* and *Firmicutes* were the dominant phyla detected in the gut of KC and WT mice, but significant differences were not observed between cohorts. However, whereas *Actinobacteria* were present in low abundance in both WT and in young KC mice, this phylum increased to nearly 60% abundance in the KC cohorts by week 20 (FIG. 2A). Conversely, *Actinobacteria* did not increase with age in the WT cohort. *Deferribacteres* were also present in very low abundances before 24 weeks in KC mice, but increased abruptly in weeks 28-36 (FIG. 2A). At the family level, *Bifidobacteriaceae* were significantly higher in the fecal samples of KC mice at 9, 20, and 32 weeks. Conversely, *Clostridiaceae* were enriched in WT controls at week 36 (FIG. 6). At the genus level, KC cohorts clustered separately from WT controls after week 13 (FIG. 7). To identify different genera in the gut of WT and KC cohorts, linear discriminant analysis (LDA) was performed on serially collected fecal samples. Again, no differences in bacterial taxa between WT and KC cohorts were observed in the early weeks of life. However, *Bifidobacterium* was progressively enriched in the KC cohort from weeks 13-36 (FIG. 2B). Principal coordinate analysis (PCoA) computed using weighted UniFrac distance metrics (Caporaso J G et al. Nature Methods 7: 335-336 (2010); Lozupone C *Microbiol* 71: 8228-8235) revealed distinctly different gut microbial communities in WT and KC cohorts which increased with progressive oncogenesis (FIG. 2C, D).

Figure 8A:
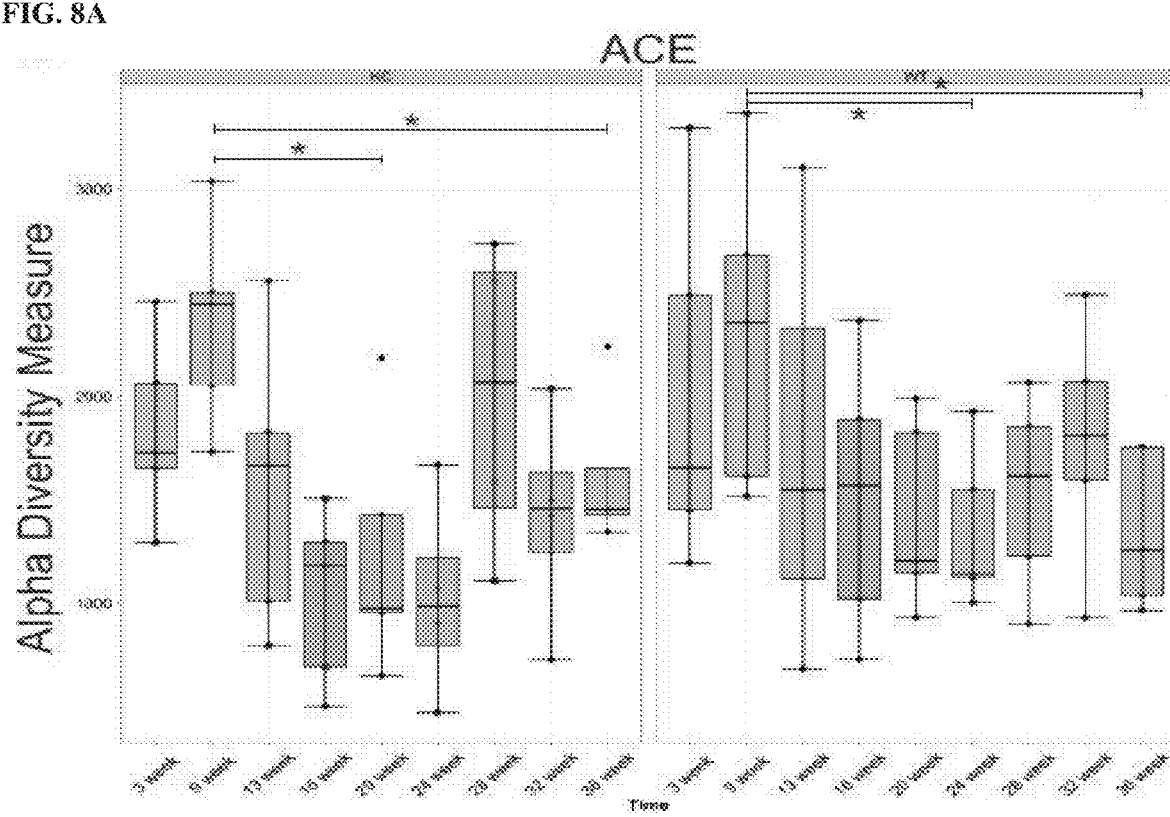
FIGS. 8A-8F. Longitudinal differences in the gut microbiome of KC mice based on alpha-diversity analyses. Analysis of longitudinal changes in the community richness (observed species (8C), ACE (8A), Chao1 (8B)) and diversity (Shannon (8D), Simpson (8E), Phylogenetic diversity (8F)) within WT and KC cohorts from week 3 thru week 36 of life is shown (n=5/group; *p<0.05).
Figure 8B:
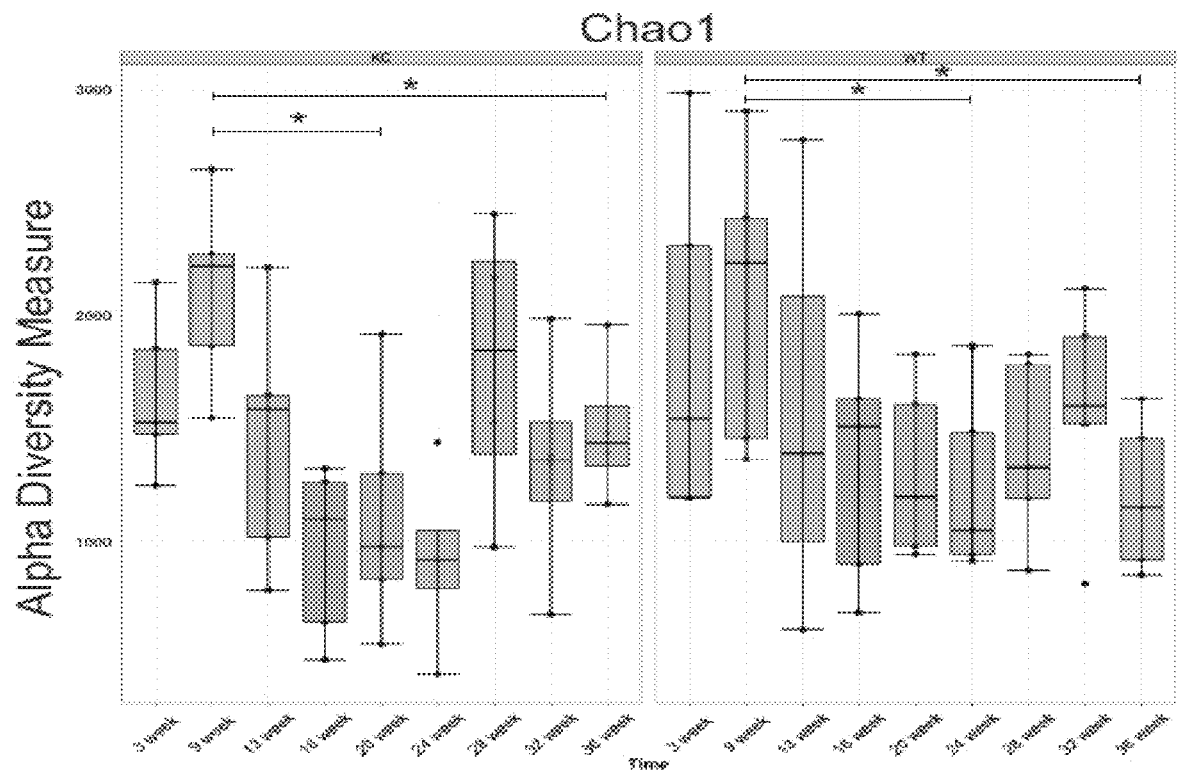
Figure 8C:
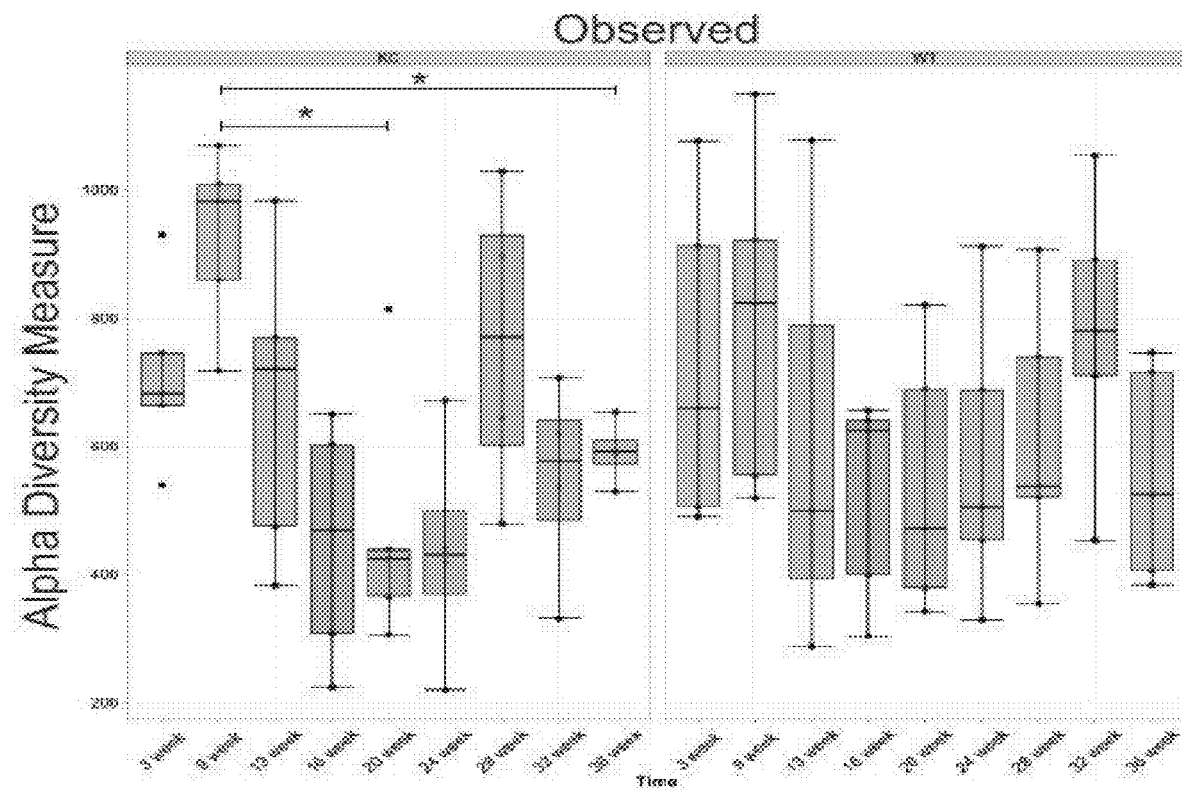
Figure 8D:
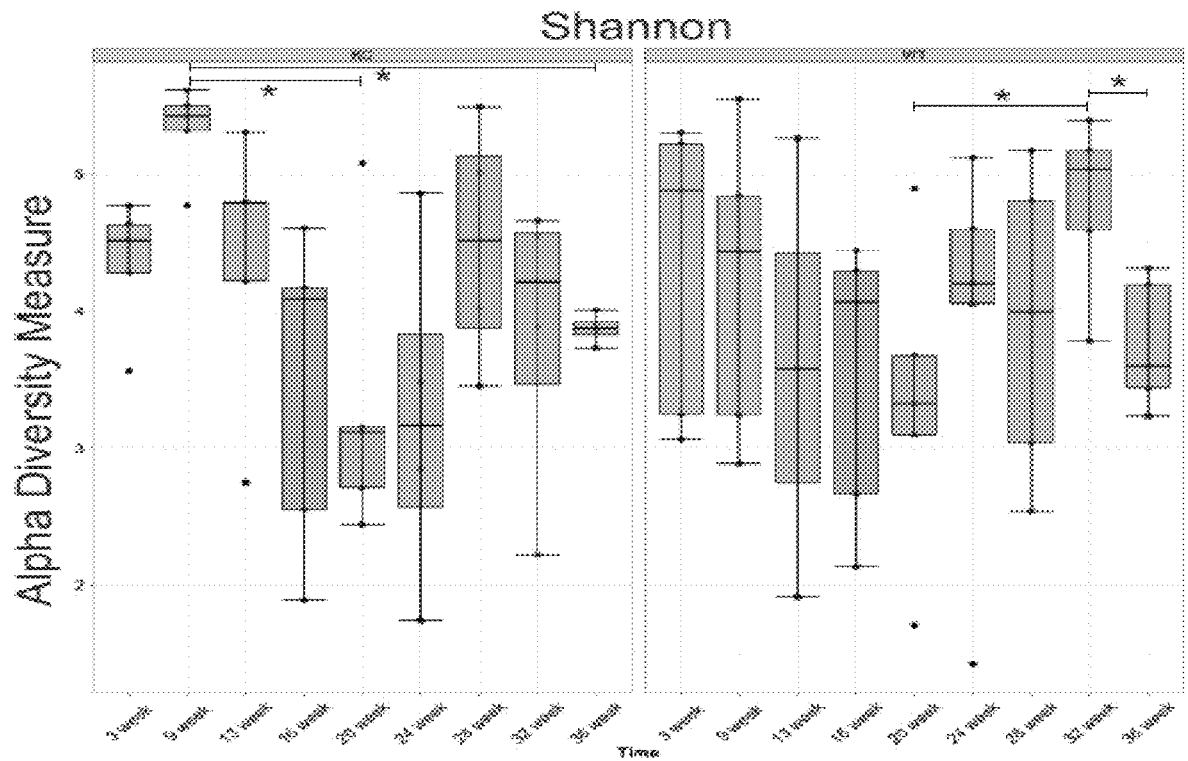
Figure 8E:
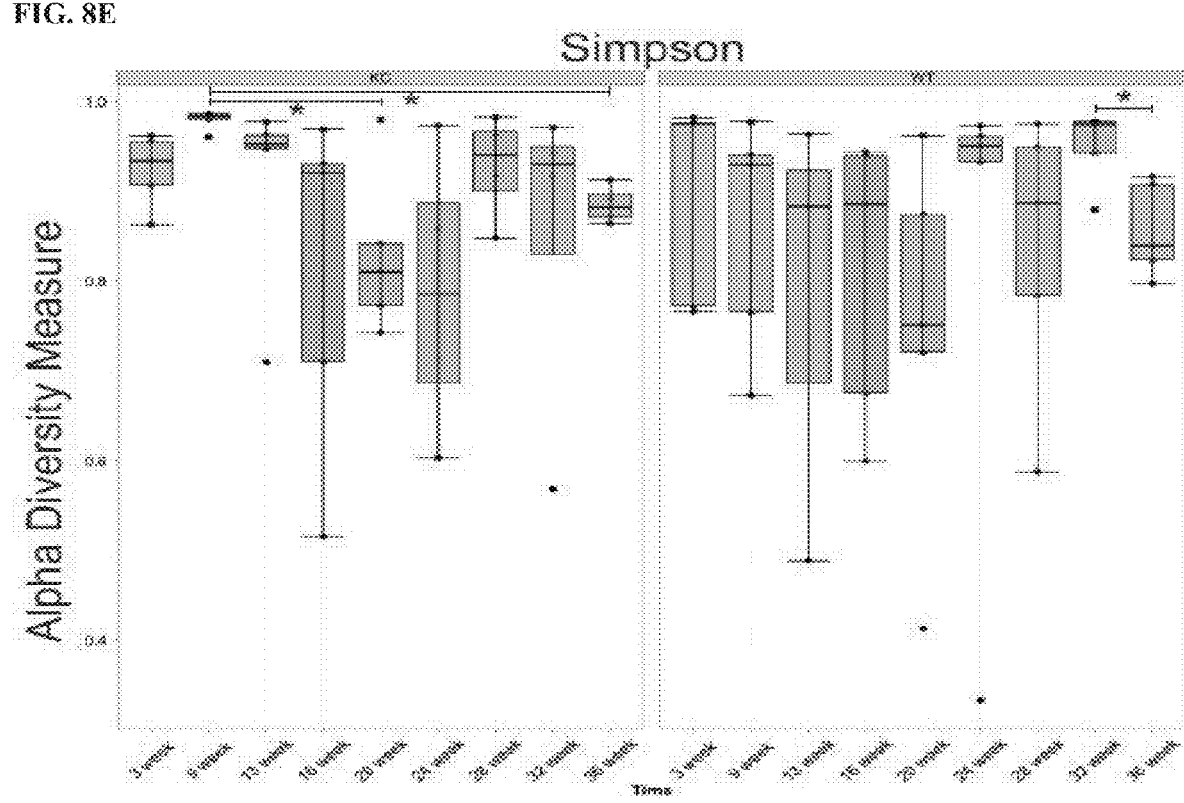
Figure 8F:
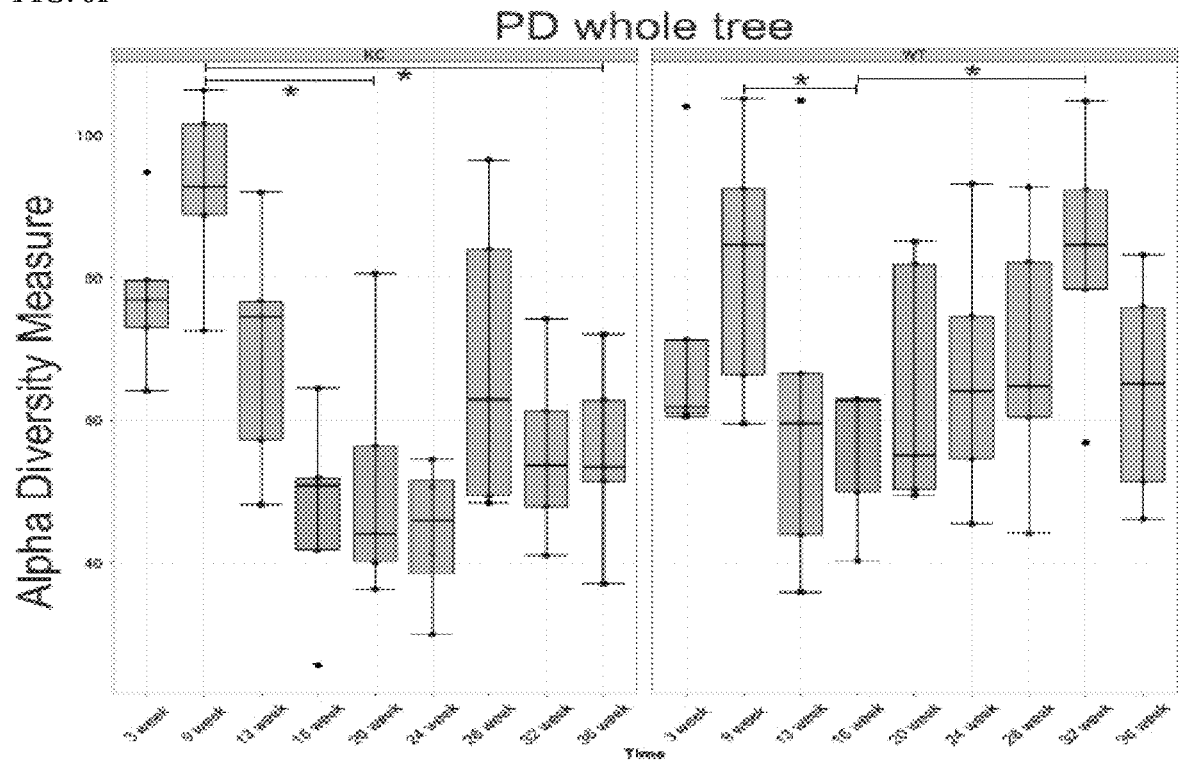

To further probe longitudinal differences in the gut microbiome in WT and KC cohorts, α-diversity analyses were employed, including taxonomy-based richness estimators (ACE, Chao1; Caporaso J G et al. Nature Methods 7: 335-336 (2010)) (FIG. 8A-8C), observed operational taxonomic units (OTUs), diversity indices (Shannon, Simpson), and phylogeny-based diversity (PD) (FIG. 8D-F). Significant differences in the community richness, observed OTUs, and diversity indices were found within the KC cohort at week 9 compared with weeks 20 and 36. By contrast, bacterial community structure and membership was comparatively stable in WT mice (FIG. 8A-8F).

Figure 3A:
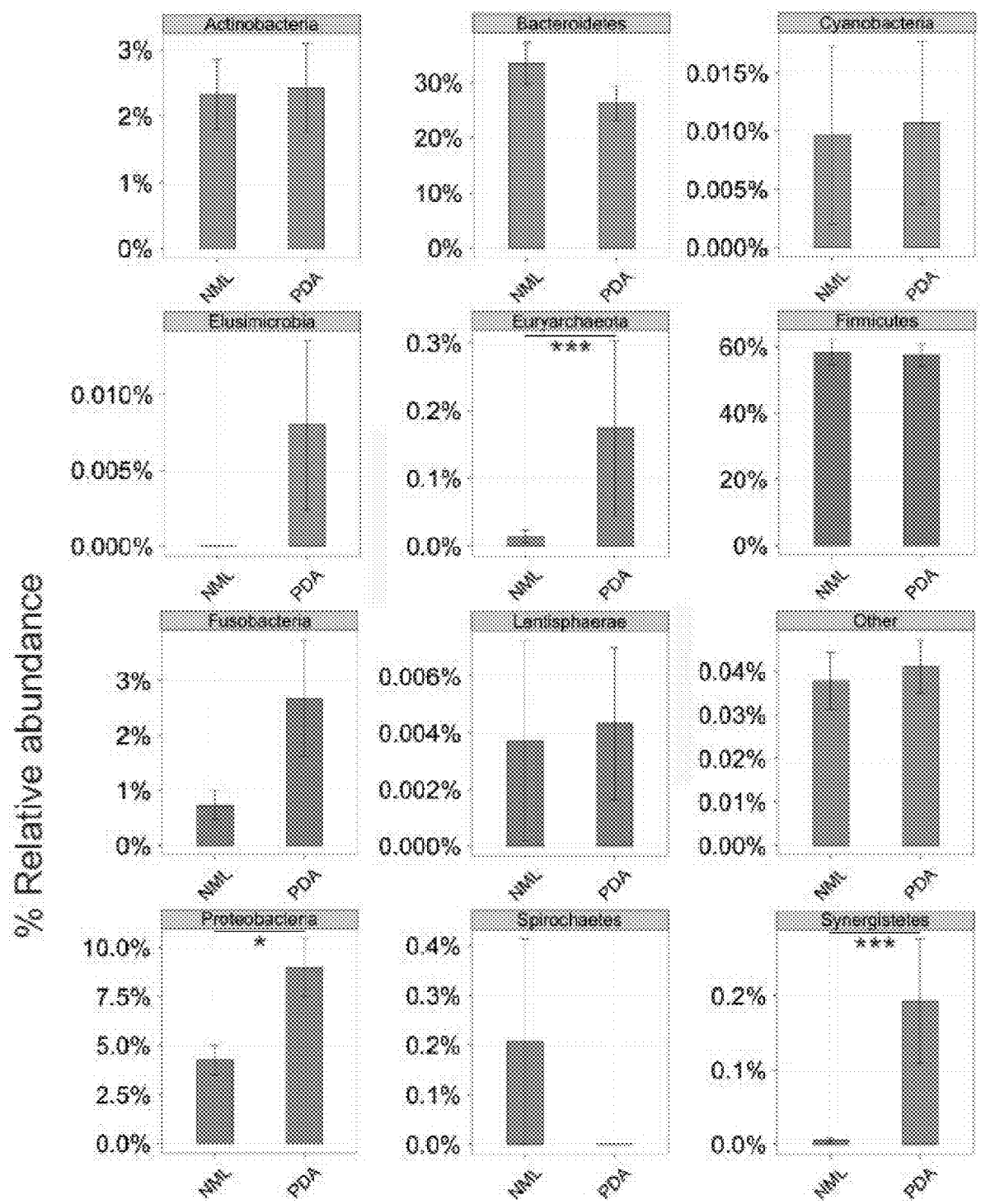
FIGS. 3A-3D. PDA patients have distinct gut microbiomes. (3A) Taxonomic distribution of GI tract microbiota in PDA patients (n=32) and age-, gender-, and BMI-matched non-cancer subjects (n=31) is shown. Labels indicate phyla at average percentage relative abundance≥0.1%. The remaining phyla are binned together as 'Other' (*p<0.05, ***p<0.001). (3B) Cladogram showing differential taxonomic hierarchies in the gut of patients in the PDA (red) and NML (red) cohorts detected by LEfSe. Colors indicate the cohorts in which differential clade was significantly abundant. (3C) Differentially abundant genera in the gut of PDA patients (red) and healthy subjects (green) were identified by LDA effect size measurements. (3D) Venn diagram summarizing microbial genera in the gut and tumor of PDA patients. Shared taxa in both communities are indicated by the overlap.
Figure 3A:
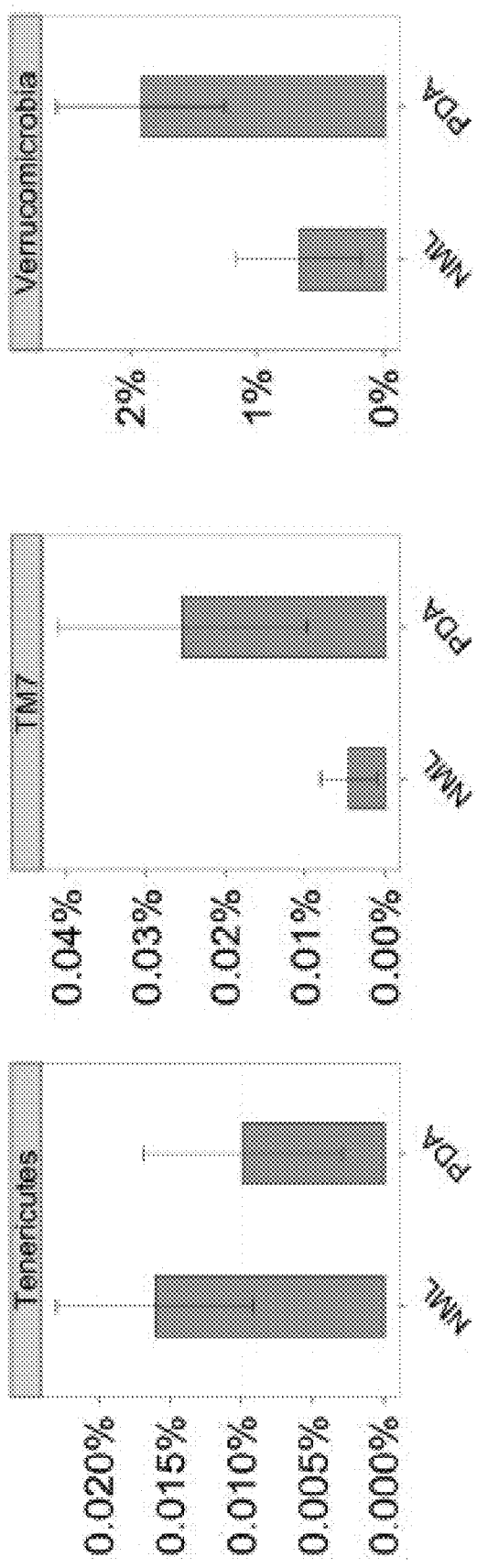
Figure 3B:
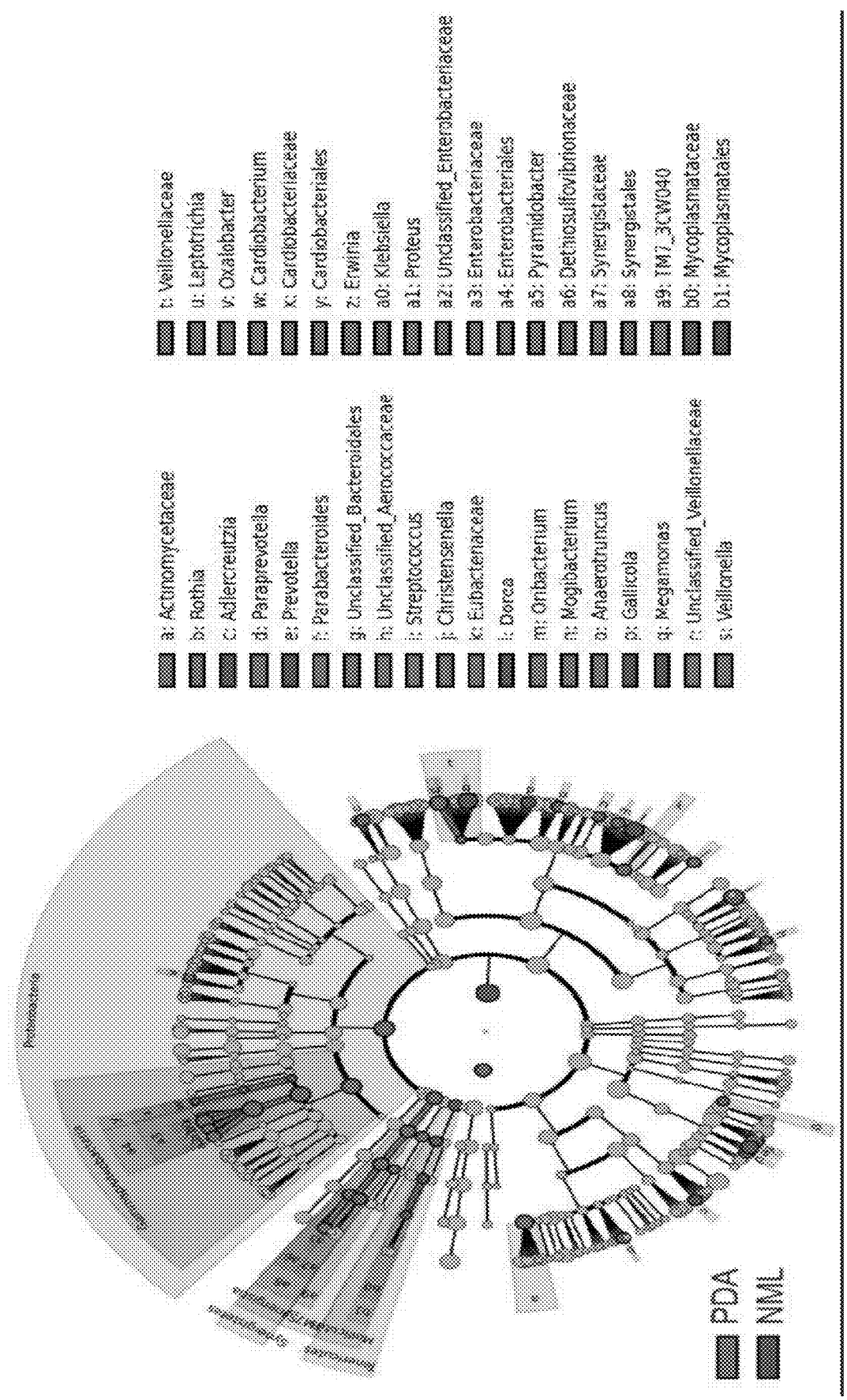
Figure 3C:
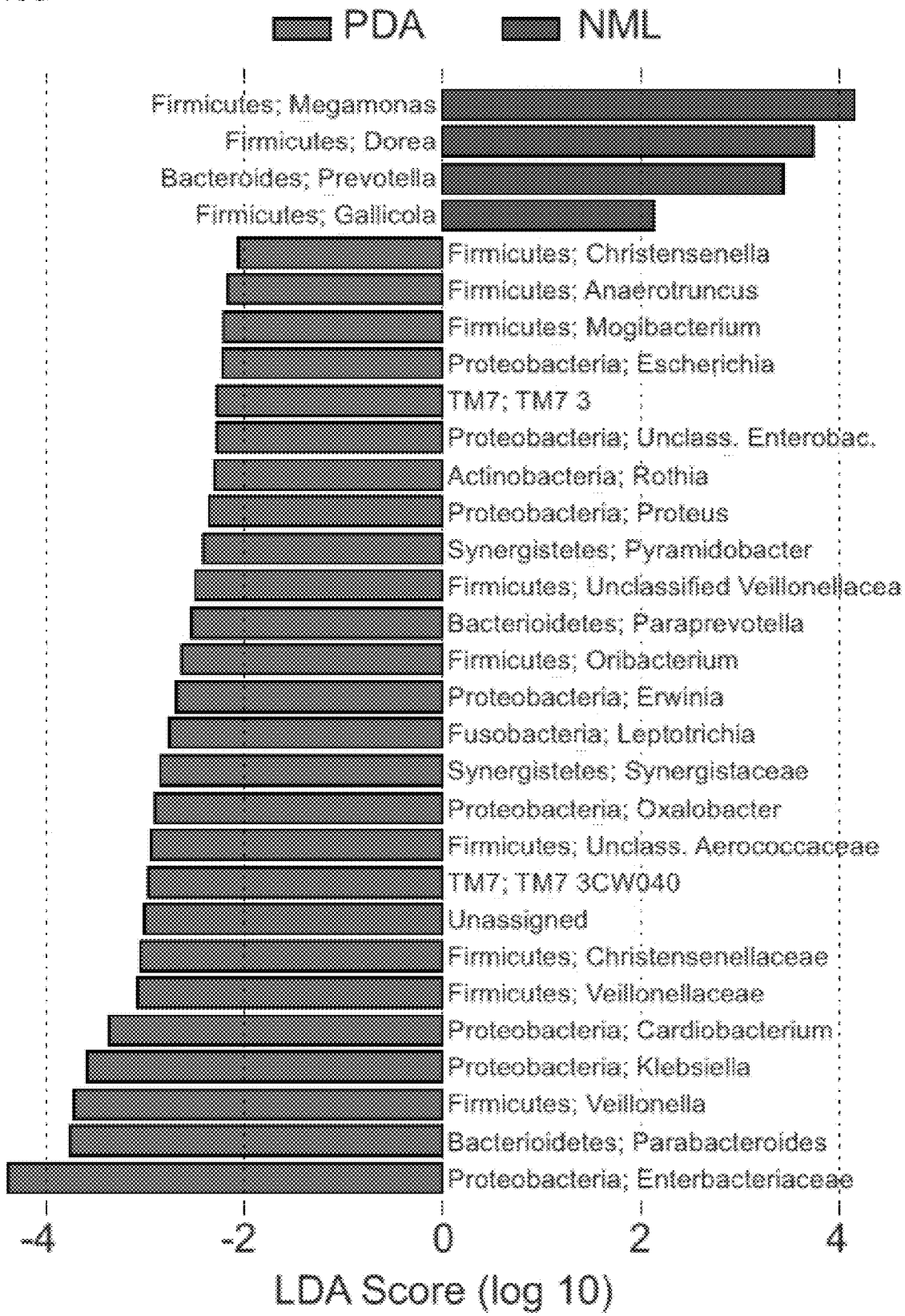
Figure 3D:
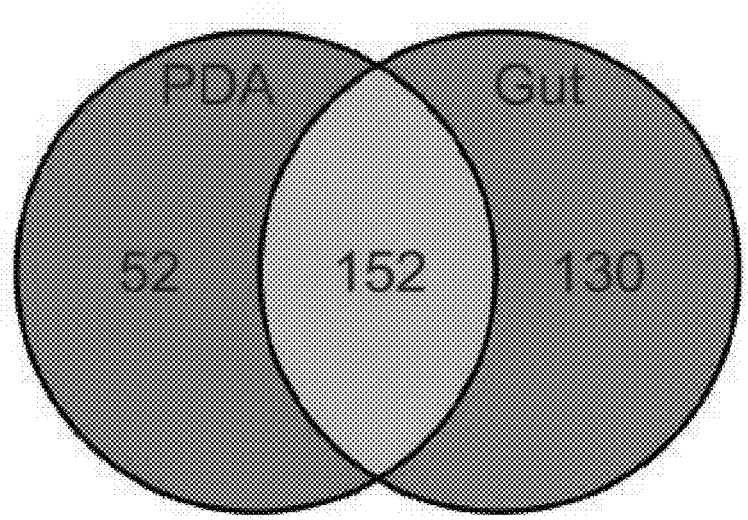
Figure 9:
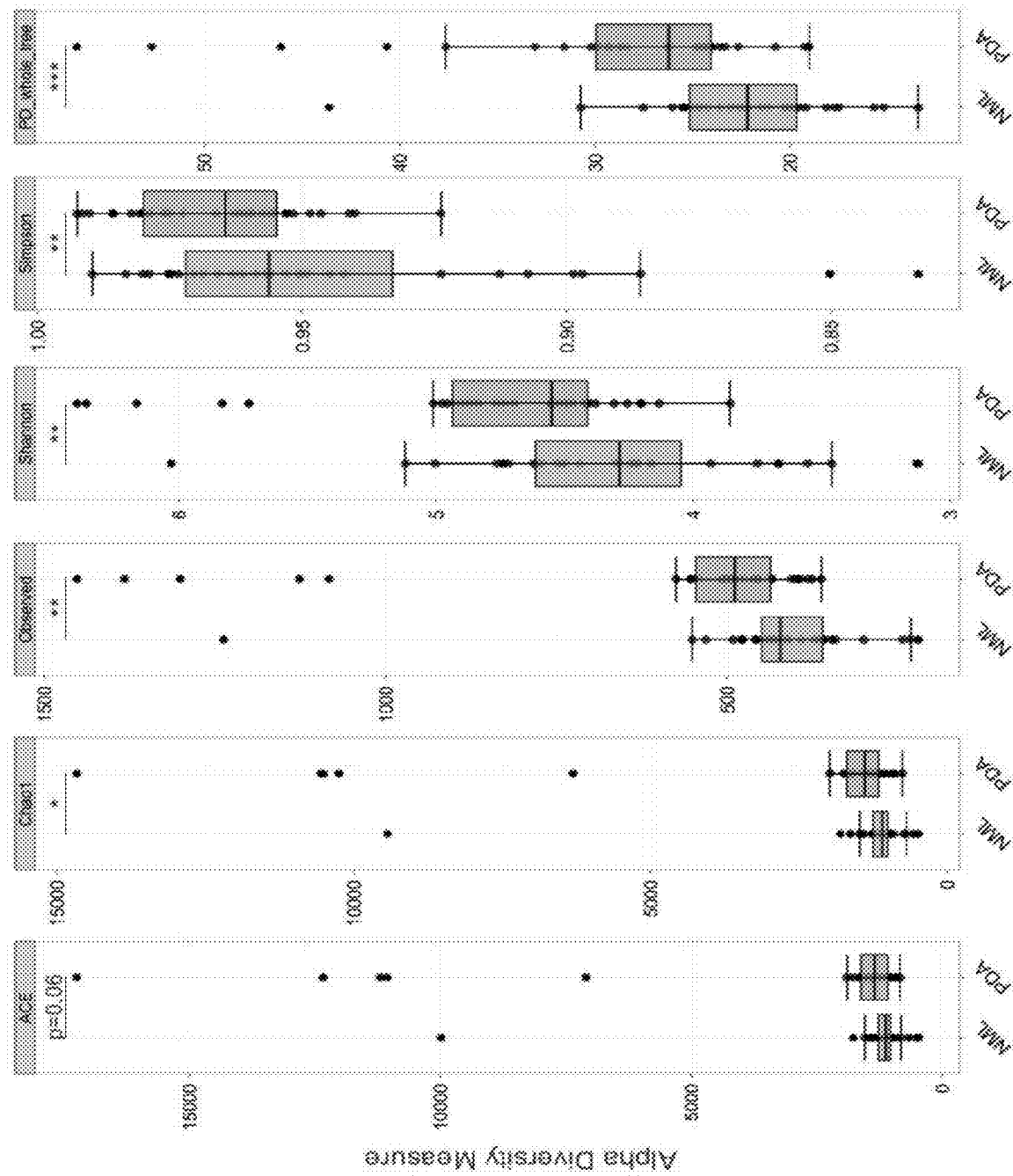
FIG. 9. Alpha-diversity measures of the gut microbial communities in PDA patients and healthy controls. The gut microbiome of PDA patients (n=32) and matched controls (n=31) were tested for differences in community richness (observed species, ACE, Chao1) and diversity (Shannon, Simpson, Phylogenetic diversity; *p<0.05, p<0.01, *p<0.001).

In order to determine that human PDA was similarly associated with a distinct gut microbiotic profile, bacterial membership and structure were evaluated in fecal samples of PDA patients (n=32) compared with age-, gender-, and BMI-matched non-tumor bearing healthy individuals (NML; n=31). At the phylum level, the gut microbiota of PDA patients and healthy controls were again dominated by *Firmicutes* and *Bacteroidetes*, but no differences were observed between cohorts (FIG. 3A). However, *Proteobacteria, Synergistetes*, and *Euryarchaeota* were significantly more abundant in PDA patients compared with healthy subjects (FIG. 3A). *Fusobacteria* and *Verrucomicrobia* were also enriched in PDA patients whereas *Spirochaetes* was more abundant in healthy controls but these did not reach statistical significance. Clade abundances were assessed using Linear discriminant analysis Effect Size (LEfSe) (Segata N et al. Genome Biol. (2011) 12(6):R60) to visualize differences in gut bacterial communities between PDA patients and healthy controls at all taxonomic hierarchies (FIG. 3B). To specifically determine differences in gut microbiota between PDA and healthy patients at the genus level, LDA analysis was performed. Numerous genera belonging to *Firmicutes, Proteobacteria*, and *Actinobacteria* were significantly expanded in PDA (FIG. 3C). Select genera within the *Bacteroidetes*, TM7, and *Synergistetes* phylum were also elevated in PDA (See Example 2). Conversely, *Firmicutes* comprising taxa including *Megamonas, Dorea*, and *Gallicola* as well as *Bacteroidetes/Prevotella* were overrepresented in healthy controls (FIG. 3C). Moreover, comparison of bacterial membership in the pancreata and gut of PDA patients indicated that relative abundances of microbiota in pancreatic tumor tissues and fecal samples were ~45% similar at the genus level, suggesting the likelihood of translocation of bacterial communities from the gut to the pancreas (FIG. 3D). Alpha diversity measures assessing the human gut microbiome suggested differences between PDA and NML groups based on ACE, Chao1, Observed OTUs, Shannon and Simpson diversities, and the PD index (FIG. 9). Collectively, these results denote dysbiosis in the bacterial community membership and structure in the gut of PDA patients compared with healthy controls.

Figure 4A:
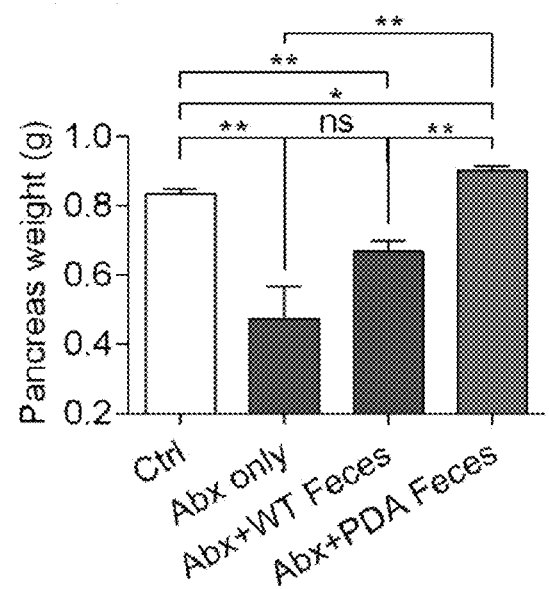
FIGS. 4A-4K. The gut microbiome in PDA-bearing hosts promotes tumor-progression and peri-tumoral immune suppression. (4A) KC mice treated with an ablative oral antibiotic regimen for 8 weeks were either repopulated with feces from 3-month old WT mice, or repopulated with feces from 3 month-old KPC mice, or sham-repopulated (vehicle only). Mice were sacrificed 8 weeks later and pancreas weights from each cohort were compared to each other and to age-matched control KC mice that were not treated with antibiotics (n=5/group). (4B, 4C) The gut microbiome of germ-free KC mice was repopulated at 6 weeks with feces from 3 month-old WT or KPC mice or sham-repopulated. (4B) Pancreas weights from each cohort were measured at 14 weeks and compared to non-germ-free control KC mice (n=5/group). (4C) Representative H&E-stained sections of pancreata of oral antibiotic-treated animals repopulated with feces from WT or KPC mice are shown. (4D-4K) Control and oral antibiotic-treated WT mice were orthotopically implanted with KPC-derived tumor cells. (4D) Gr1$^-$CD11b$^+$ F4/80$^+$ macrophages were gated and tested for expression of CD206 and (4E) TNF-α. (4F) CD4$^+$ and CD8$^+$ T cells were gated and tested for expression of T-bet, (4G) TNF-α, (4H) IFN-γ, (4I) PD-1, and (4J) CD44 (CD4$^+$ T cells data are shown). (4K) CD4$^+$ T cells were gated and tested for expression of ICOS. Representative contour plots and quantitative data are shown. Experiments were repeated three times (n=5/group; *p<0.05, p<0.01, *p<0.001, ****p<0.0001).
Figure 4B:
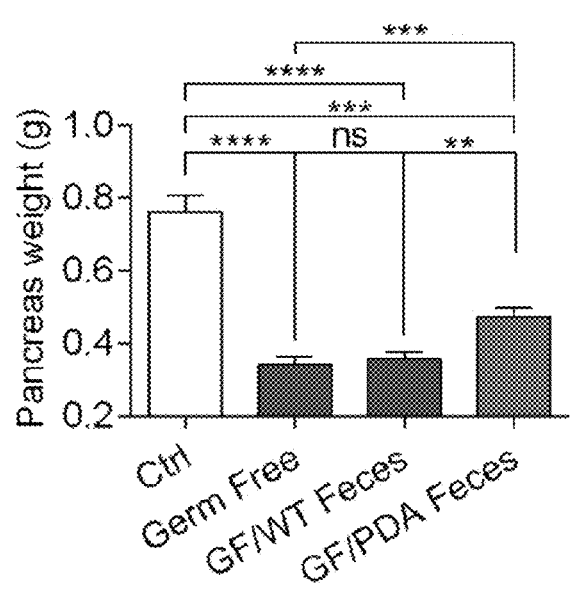
Figure 4C:
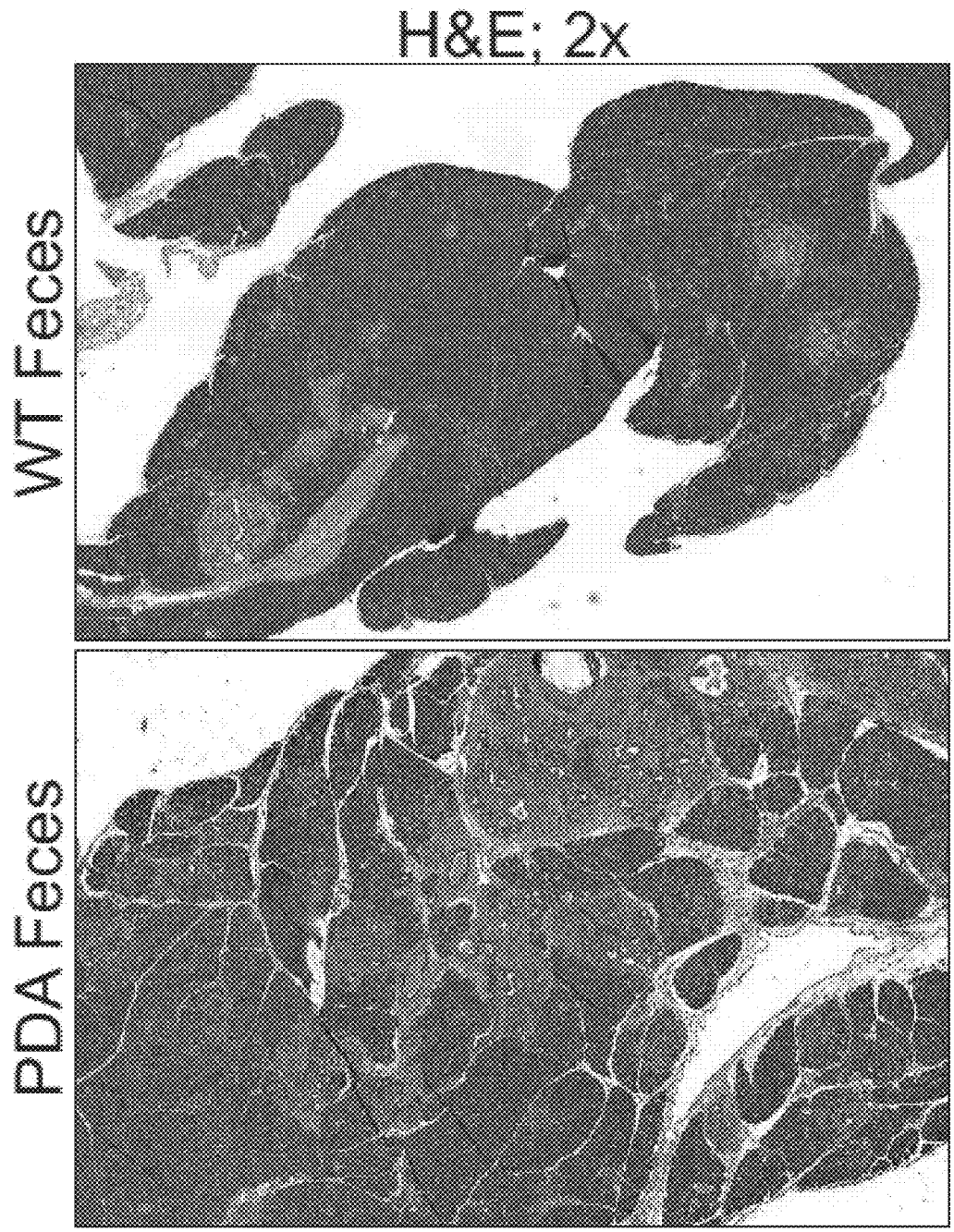
Figure 10A:
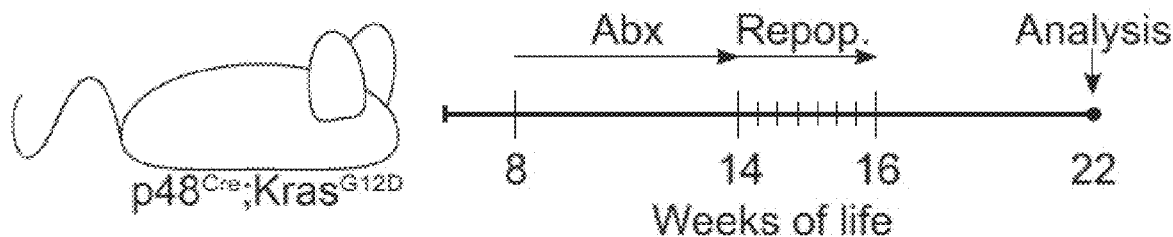
FIGS. 10A-10H. Microbial ablation enhances anti-tumor immunity in PDA. (10A) Schematic indicating that KC mice treated with an ablative oral antibiotic regimen beginning at 8 weeks of life was repopulated at 14 weeks of life with either feces from 3 month-old WT or KPC mice or sham-repopulated (vehicle only). Animals were sacrificed at 22 weeks of life. (10B) Schematic indicating that germ-free KC were repopulated at 6 weeks of life with feces from 3 month-old WT or KPC mice or sham-repopulated. Animals were sacrificed at 14 weeks of life. (10C-10F) Control and ablative oral antibiotic-treated WT mice were orthtopically implanted with KPC-derived tumor cells. (10C) The percentages of tumor-infiltrating CD3$^+$ T cells and (10D) Gr1$^+$ CD11b$^+$ MDSC among CD45$^+$ peri-tumoral leukocytes were calculated. (10E) The percentages of tumor-infiltrating CD4$^+$ and CD8$^+$ T cells as a subset CD3$^+$ cells were determined by flow cytometry. (10F) FoxP3 expression was determined in CD4$^+$ T cells in each cohort. (10G) A heat map was constructed based on results of a nanostring array testing inflammatory gene expression in 3-week orthotopic PDA tumors in mice treated with an ablative oral antibiotic regimen (n=3) or controls (n=2). (10H) PDA-infiltrating T cells from orthotopic KPC tumor-bearing mice that had been treated with an ablative oral antibiotic regimen or sham-treated were harvested by FACS, mixed with FC1242 cells in a 1:10 ratio, and subcutaneously implanted in the flank of recipient mice. Additional controls received FC1242 cells alone. Tumor volume was measured at serial intervals (n=5/group; *p<0.05, p<0.01, **p<0.0001).
Figure 10B:
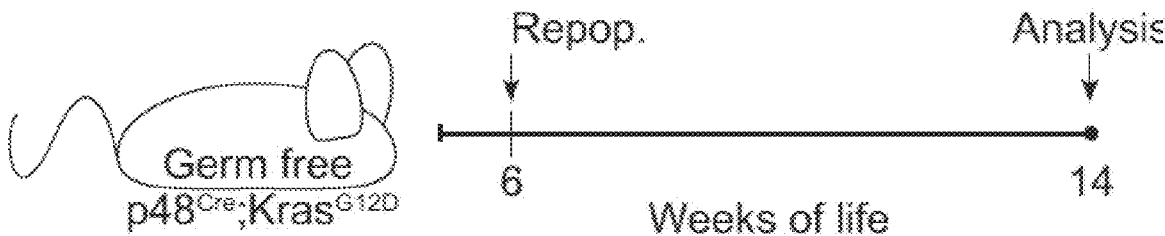

As indicted in this Example, the gut microbiome is distinct in PDA in both mice and humans, and that germ-free mice are protected from PDA; thus, it was postulated that pathogenic bacteria actively promote pancreatic oncogenesis in genetically susceptible hosts. To test this, gut bacteria in KC mice were ablated using oral antibiotics and then selectively repopulated cohorts using feces derived from either WT mice or KPC mice before sacrifice at 22 weeks of life (FIG. 10A). Consistent with results in this Example, bacterial ablation was protective against PDA growth (FIG. 4A). However, repopulation using KPC-derived feces accelerated tumor growth to baseline levels whereas repopulation with feces from age-matched WT mice failed to significantly accelerate PDA growth (FIG. 4A). Similarly, whereas germ-free KC mice were protected from oncogenesis as shown above, repopulation using feces derived from PDA-bearing mice, but not WT mice, accelerated disease progression (FIG. 10B and FIG. 4B, C).

Figure 4D:
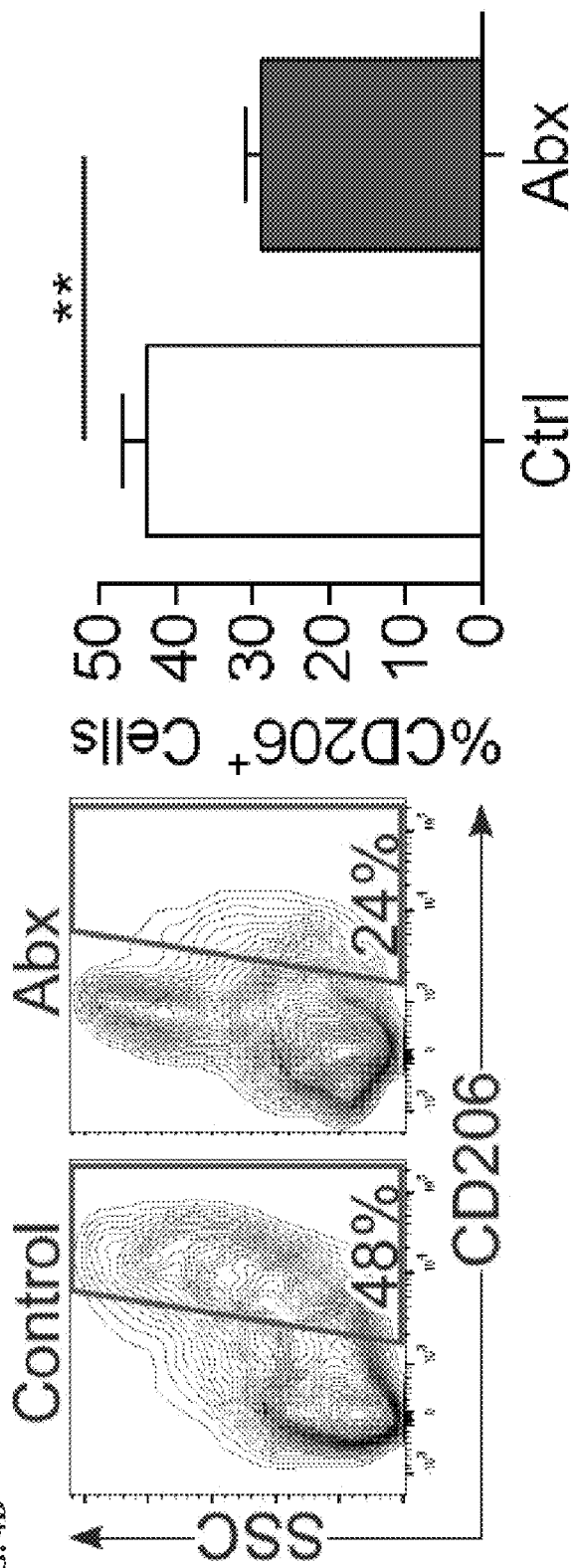
Figure 4E:
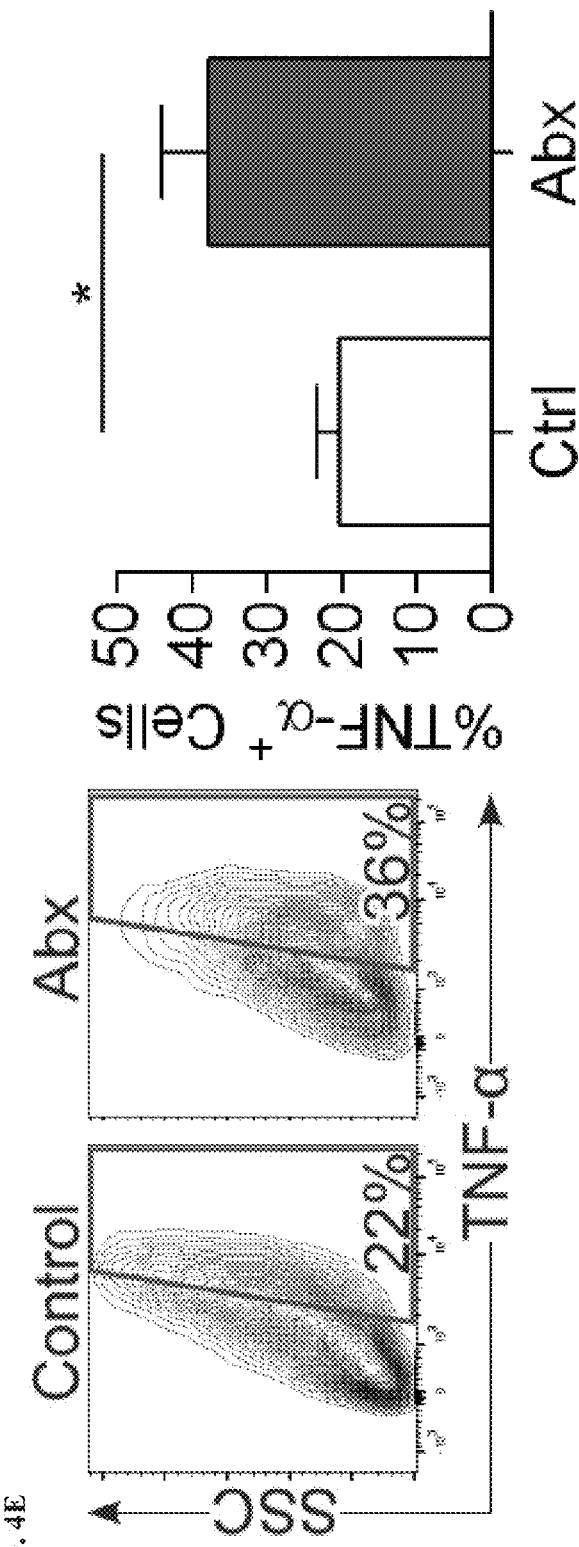
Figure 4F:
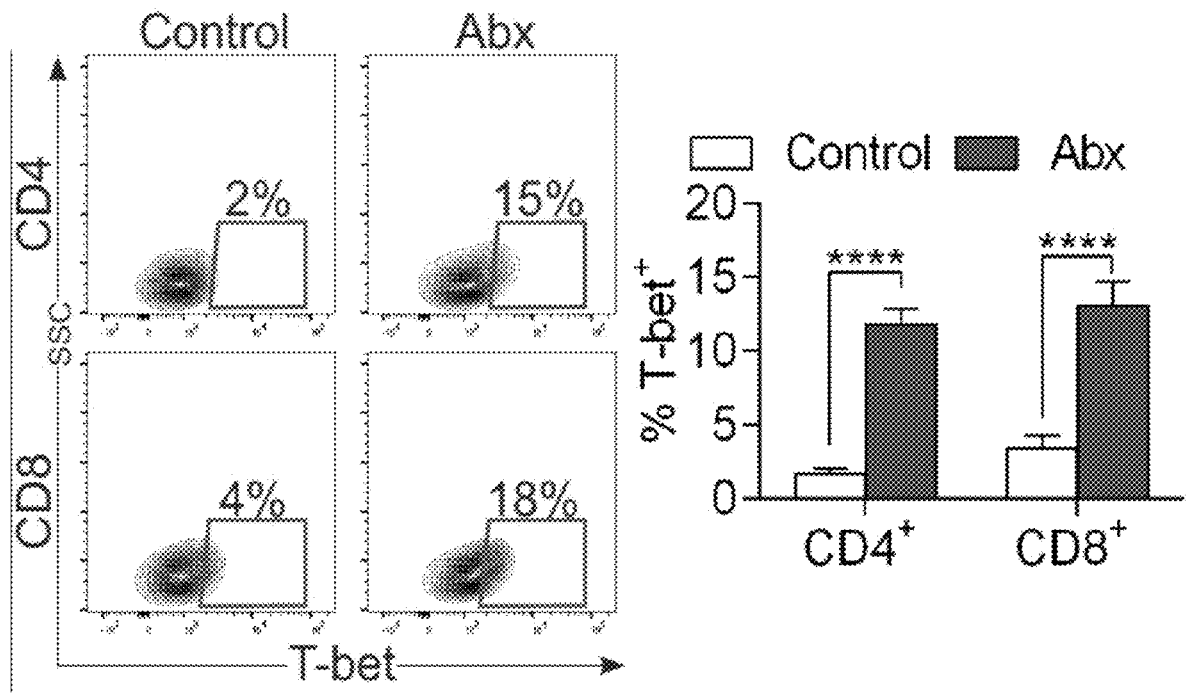
Figure 4G:
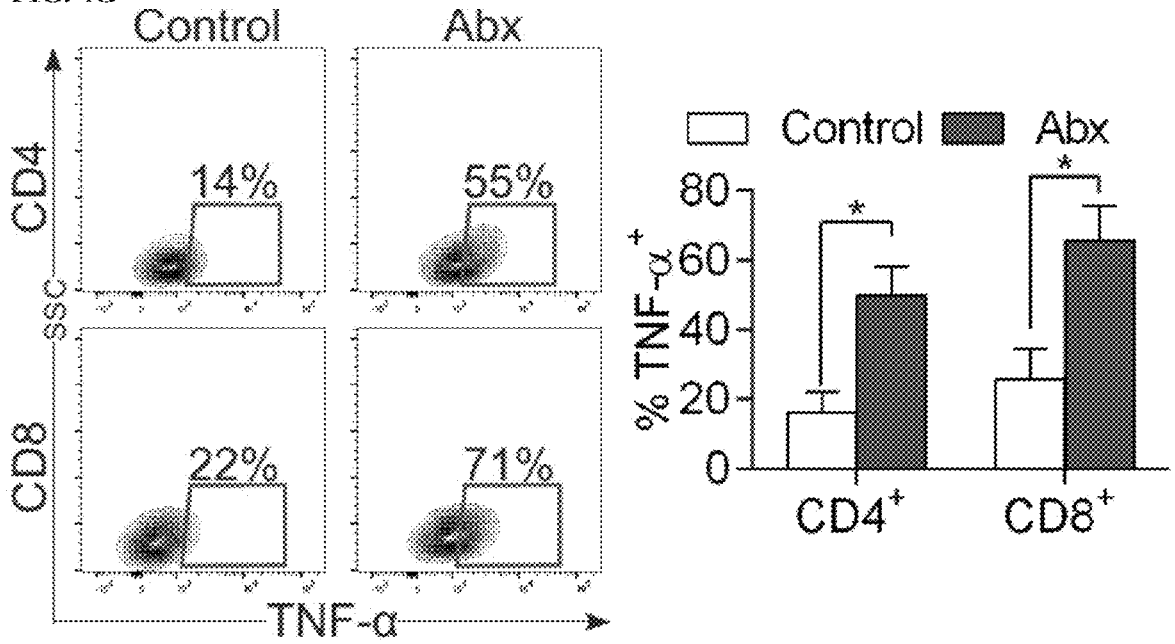
Figure 4H:
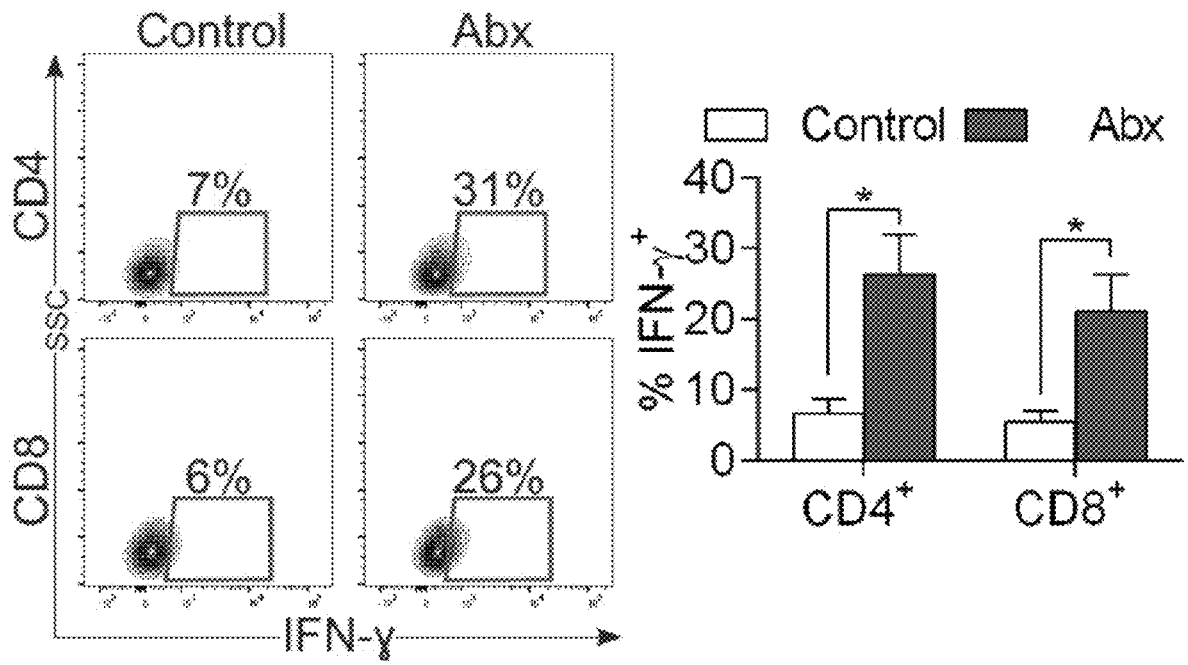
Figure 4I:
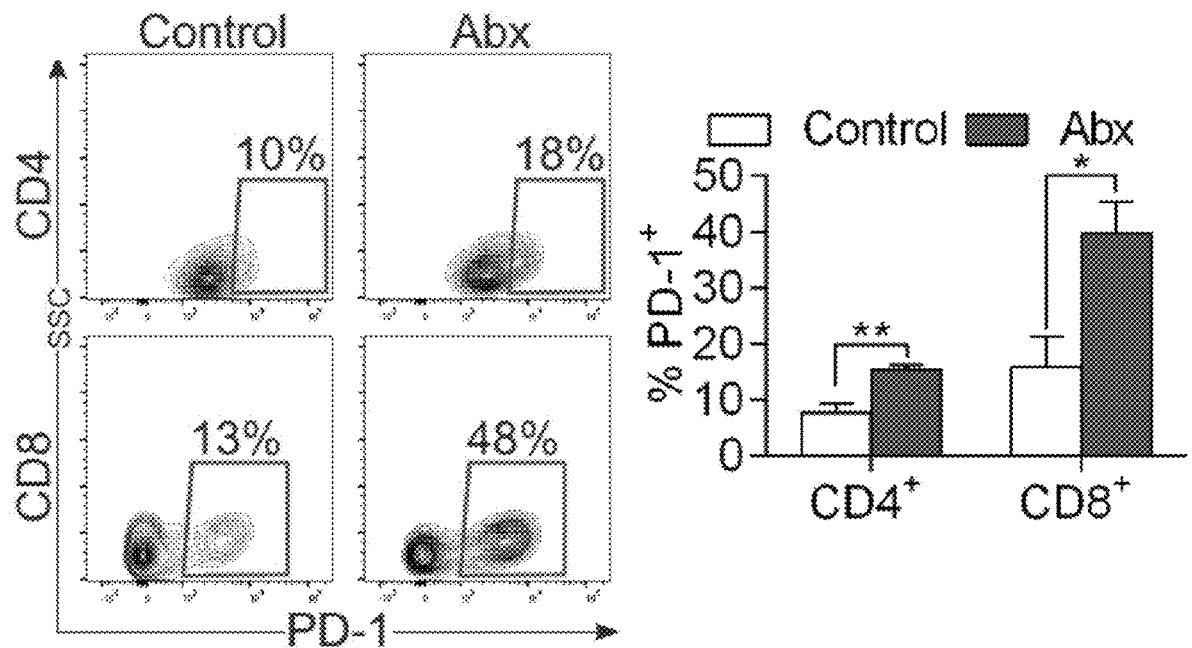
Figure 4J:
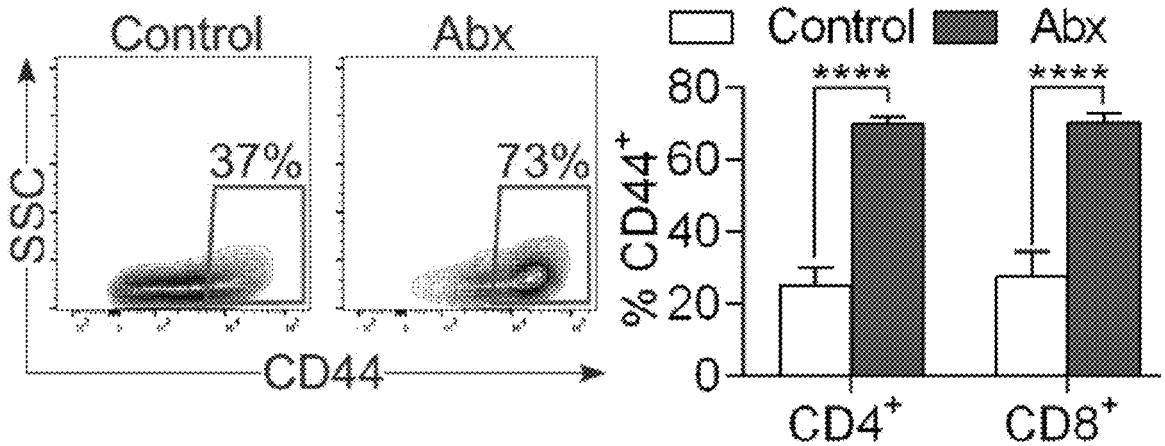
Figure 4K:
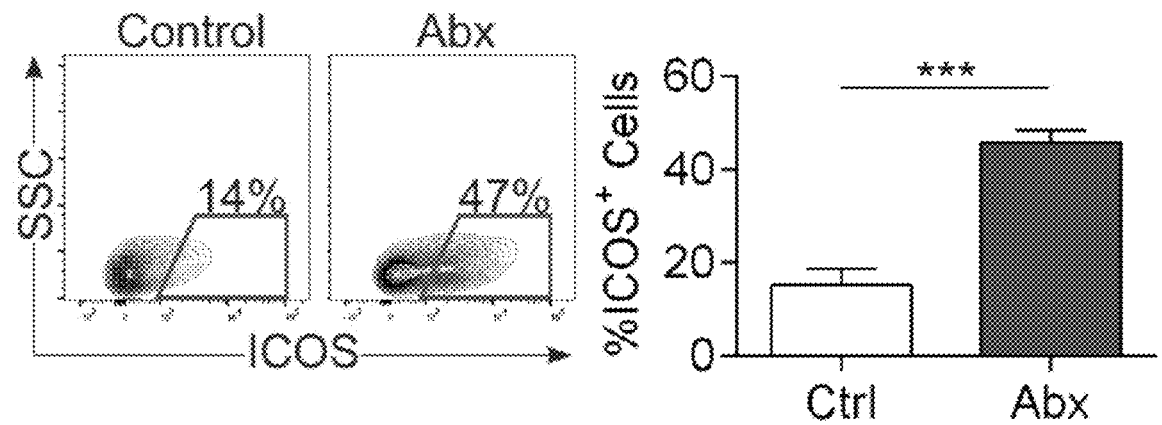
Figure 10C:
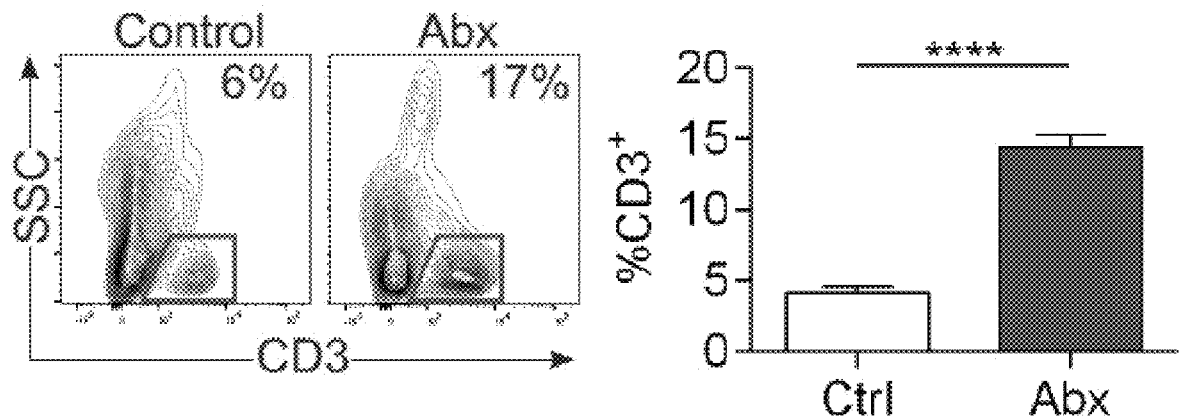
Figure 10D:
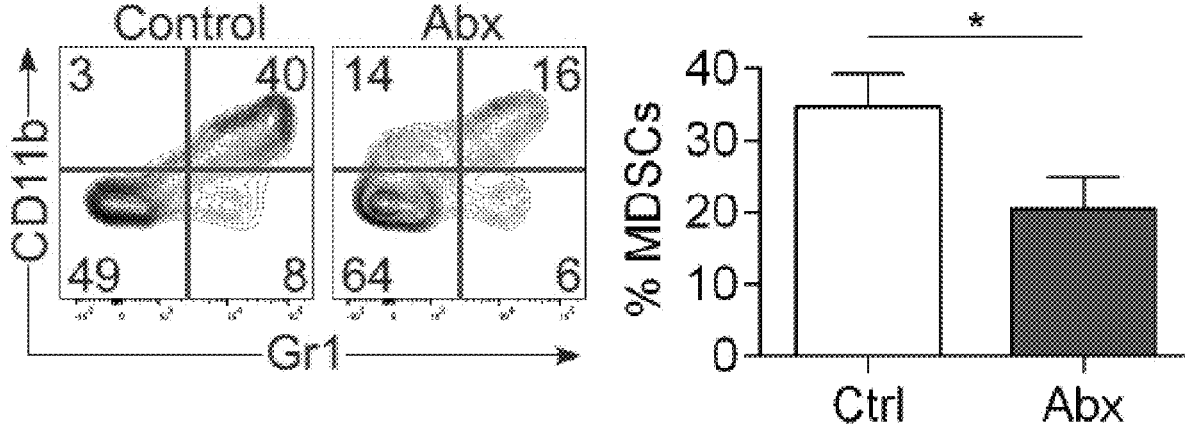
Figure 10E:
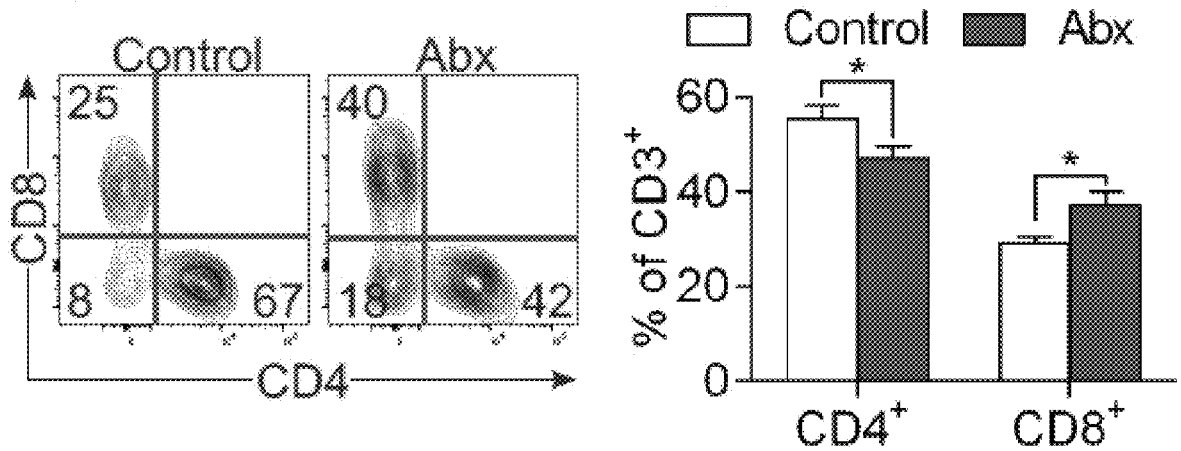
Figure 10F:
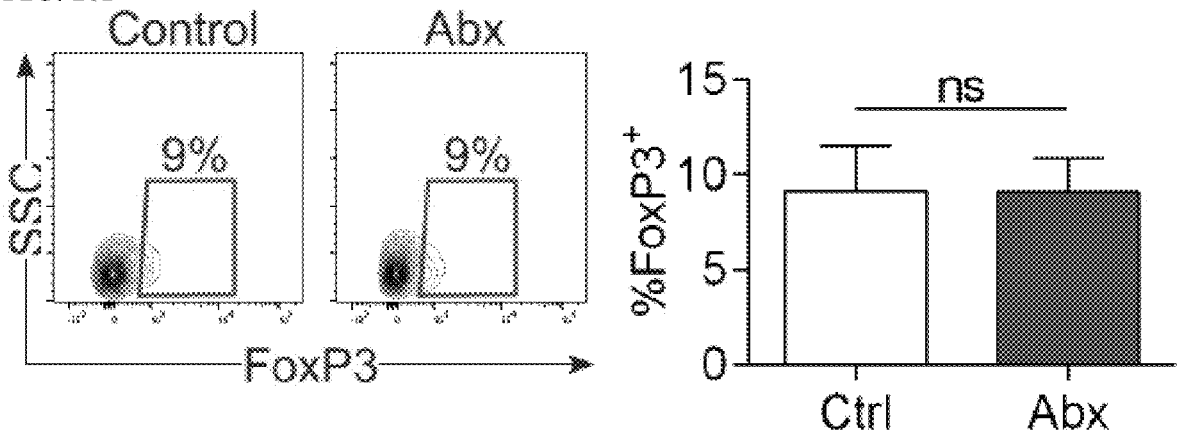
Figure 10H:
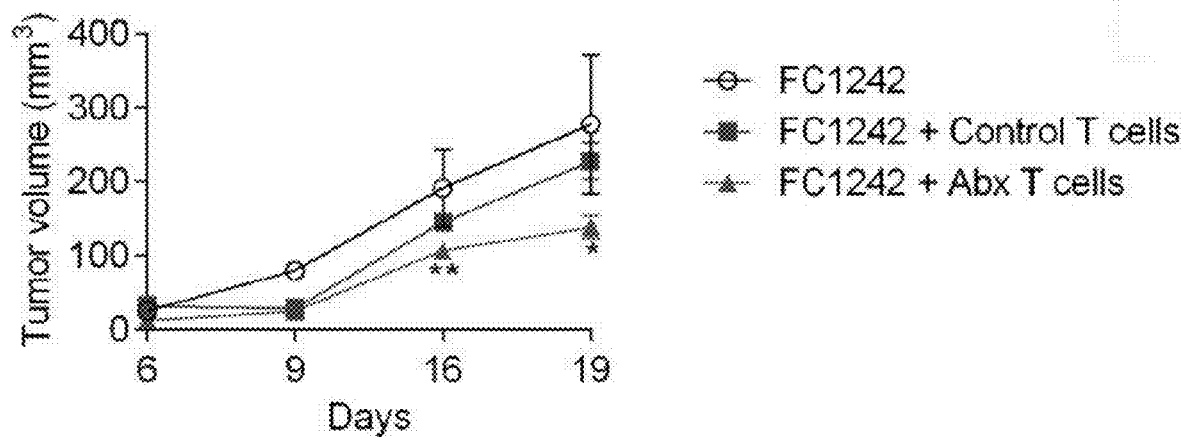
Figure 10G:
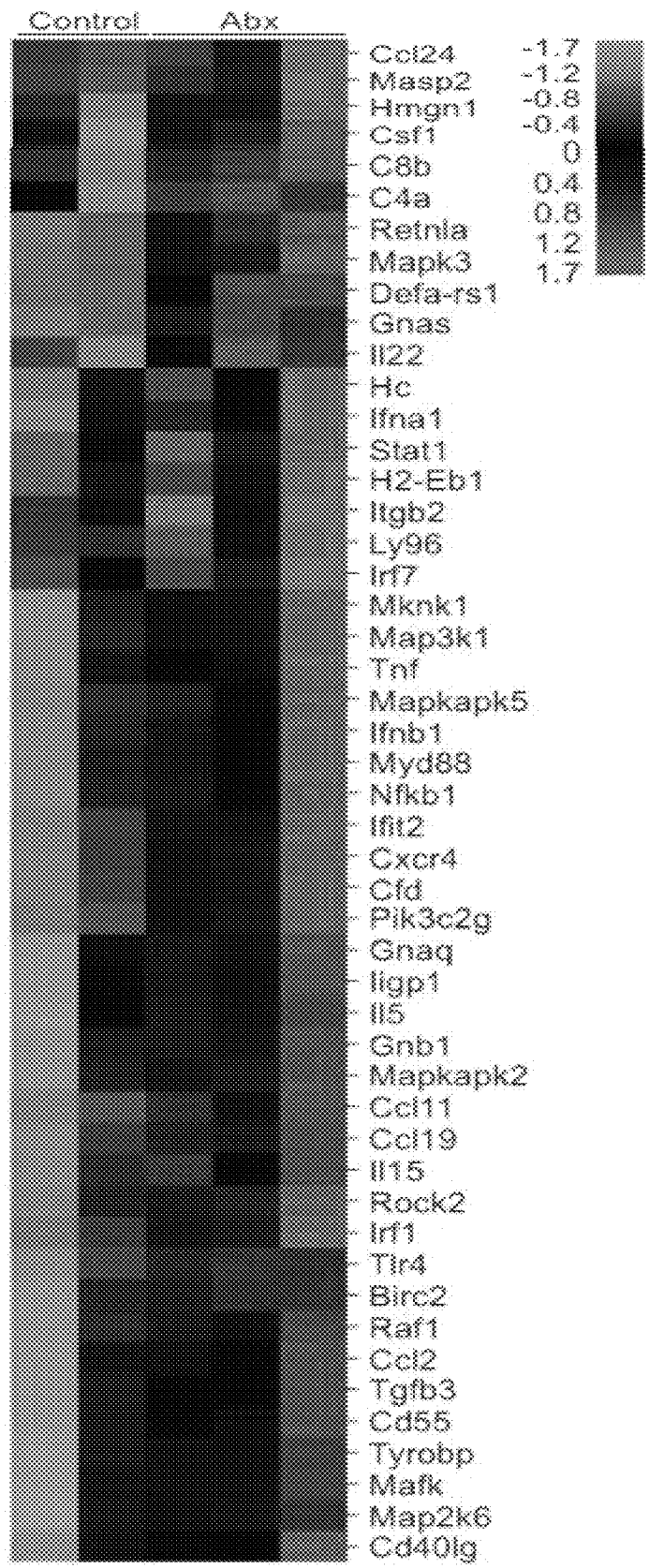
Figure 11A:
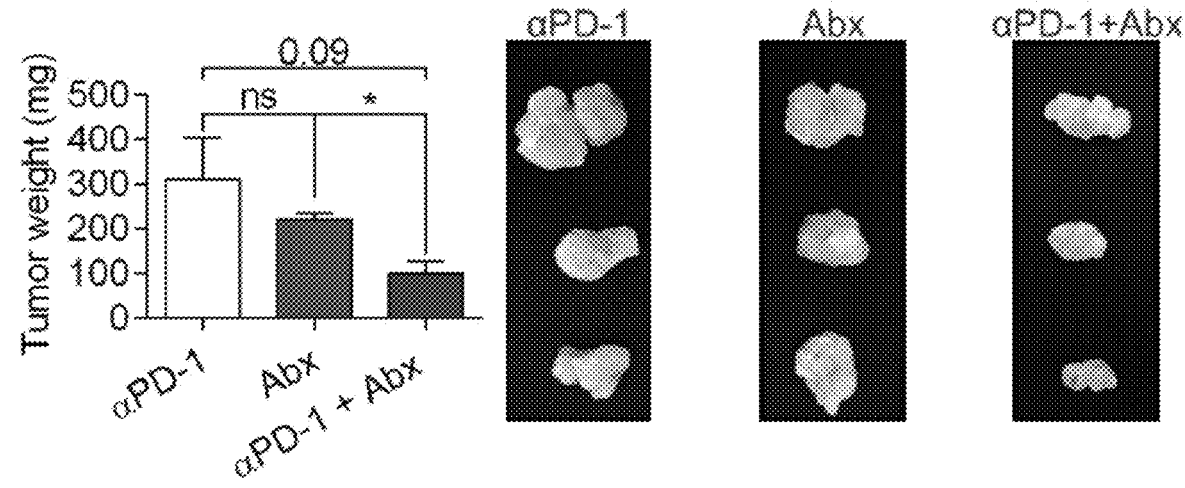
FIGS. 11A-11E. Ablation of gut bacteria synergizes with PD-1-targeted therapy. (11A-11E) WT mice were treated with αPD-1, an ablative oral antibiotic regimen, or both (n=5/group). Mice were challenged with orthotopic KPC tumor and sacrificed at 3 weeks. Treatments were started before tumor implantation and continued until the time of sacrifice. (11A) Representative gross images and quantitative tumor weight data are shown. (11B) The percentage of tumor-infiltrating CD3$^+$ T cells and (11C) the CD8:CD4 ratio were determined by flow cytometry. (11D) The percentage of CD4$^+$ T cells expressing T-bet and (11E) TNF-α was assessed by intra-cellular flow cytometry (*p<0.05; **p<0.01).
Figure 11B:
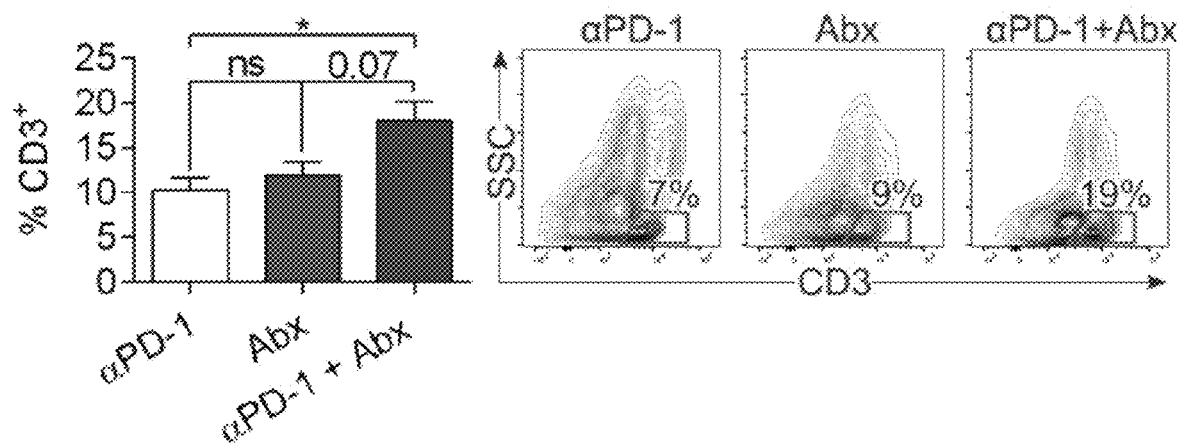
Figure 11C:
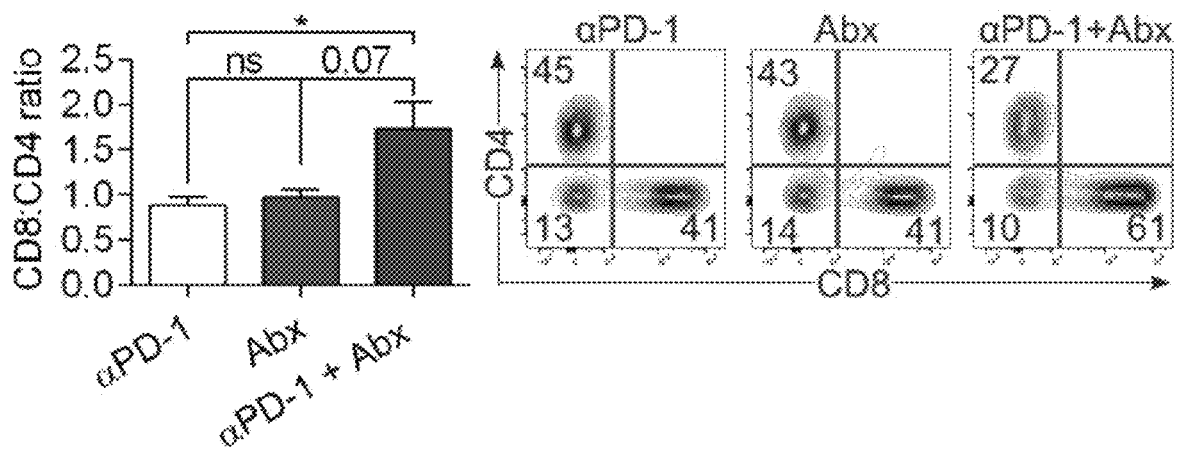
Figure 11D:
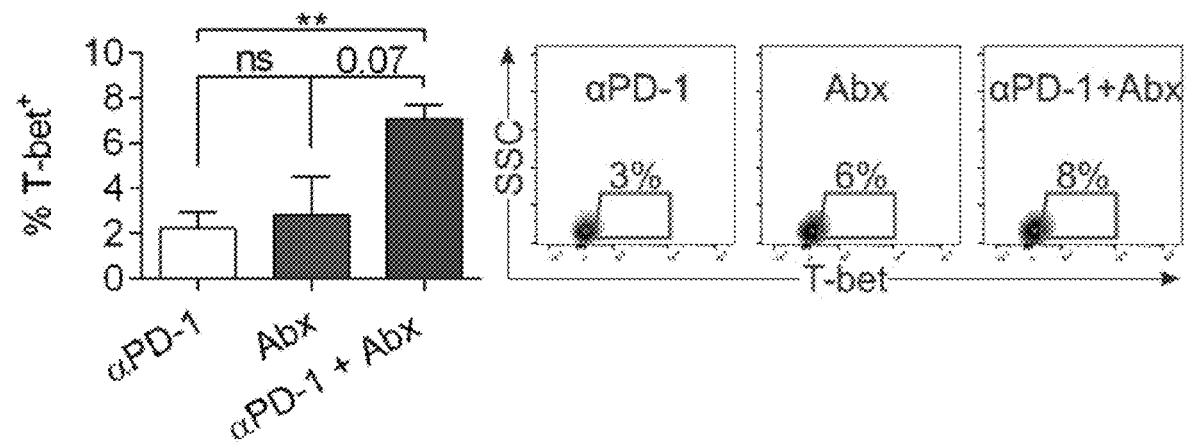
Figure 11E:
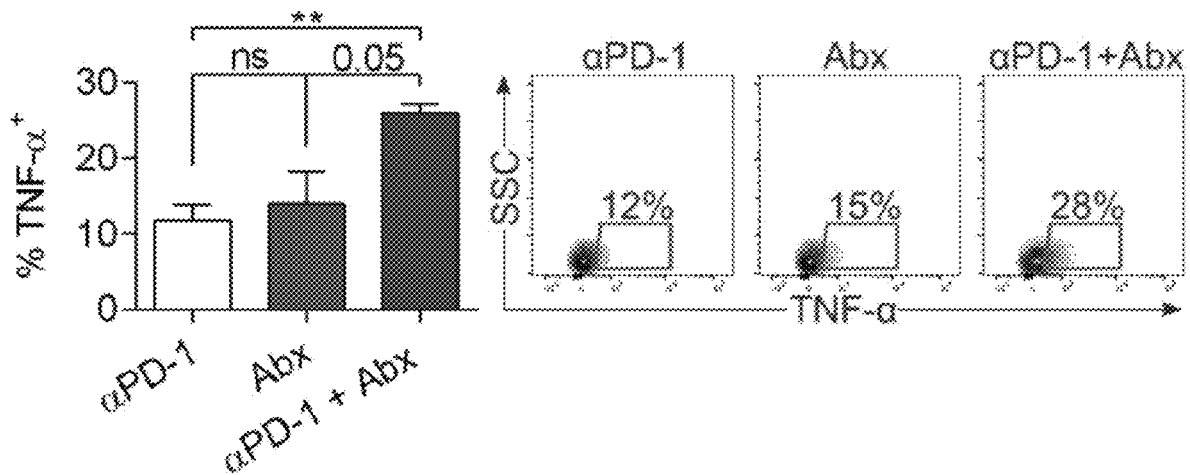

Antibiotic ablation resulted in a ~4-fold increase in the fraction of peri-tumoral T cells and a concomitant ~2-fold reduction in the fraction of myeloid-derived suppressor cells (MDSC) (FIG. 10C, D), suggesting that the gut microbiome contributes to immune-suppression in PDA. Further, analysis of the phenotype of tumor-infiltrating macrophages (TAMs) suggested that ablation of the gut microbiome led to a reduction in the fraction of immune-suppressive CD206$^+$ M2-like TAMs with a concomitant increase in TNF-$\alpha^+$ M1-like TAMs (FIG. 4D, E). Anti-microbial treatment resulted in an increased intra-tumoral CD8:CD4 T cell ratio (FIG. 10E), which has been associated with enhanced immunogenicity in PDA[11]. Moreover, microbial ablation induced enhanced CD4$^+$ T cell Th1-polarization and CD8$^+$ T cell cytotoxic phenotype as evidenced by upregulation of T-bet (FIG. 4F), TNF-$\alpha$ (FIG. 4G), and IFN-$\gamma$ (FIG. 4H). Similarly, intratumoral CD4$^+$ and CD8$^+$ T cells in antibiotic-ablated mice increased their expression of PD-1 (FIG. 4I) and CD44 (FIG. 4J), and CD4$^+$ T cells expressed higher ICOS (FIG. 4K) compared with their counterparts in tumors of control mice. Treg differentiation was not affected by antibiotic treatment (FIG. 10F). Whole pancreas nanostring array and Gene Ontology enrichment analysis indicated that genes associated with T cell proliferation and activation, Type I IFN, and innate immune signaling were upregulated in tumors of antibiotic-treated mice (FIG. 10G). Collectively, these data suggest that ablation of the gut microbiome enhances innate and adaptive immunogenicity in PDA. To definitively implicate enhanced adaptive immunity in the tumor-protection associated with microbial ablation, T cells were harvested from orthotopic KPC tumors in either control or oral-antibiotic treated mice and adoptively transferred to cohorts of mice challenged with subcutaneous KPC tumor. Consistent with their inactivated phenotype, transfer of PDA-infiltrating T cells from control mice failed to protect; however, tumor-infiltrating T cells derived from antibiotic-treated mice reduced tumor burden by ~50% (FIG. 10H). Further, it was found that PDA tumors in mice treated with ablative oral antibiotics coupled with $\alpha$PD-1 mAb were smaller than treatment with either therapy alone (FIG. 11A), resulting in a synergistic effect. Moreover, combined antibiotic and $\alpha$PD-1 therapy resulted in an expanded T cell infiltrate (FIG. 11B), a markedly higher CD8:CD4 ratio (FIG. 11C), enhanced Th1-polarization (FIG. 11D, E), and CD8$^+$ T cell activation (not shown).

Figure 12A:
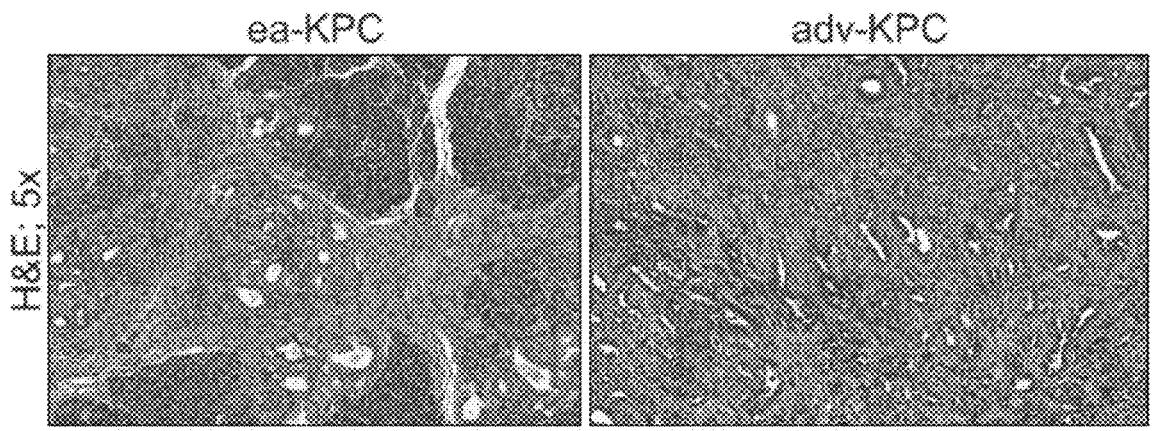
FIGS. 12A-12B. The gut microbiomes in genetically identical mice with divergent pancreatic tumor phenotypes differ in phylogenic diversity. (12A) Representative H&E-stained sections of pancreatea of 3 month-old KPC mice with early (ea-KPC; left) and advanced (adv-KPC; right) pancreatic cancer are shown. (12B) The gut microbiome of WT, ea-KPC, and adv-KPC mice were tested for differences in community richness (observed species, ACE, Chao1) and diversity (Shannon, Simpson, Phylogenetic diversity; *p<0.05).
Figure 12B:
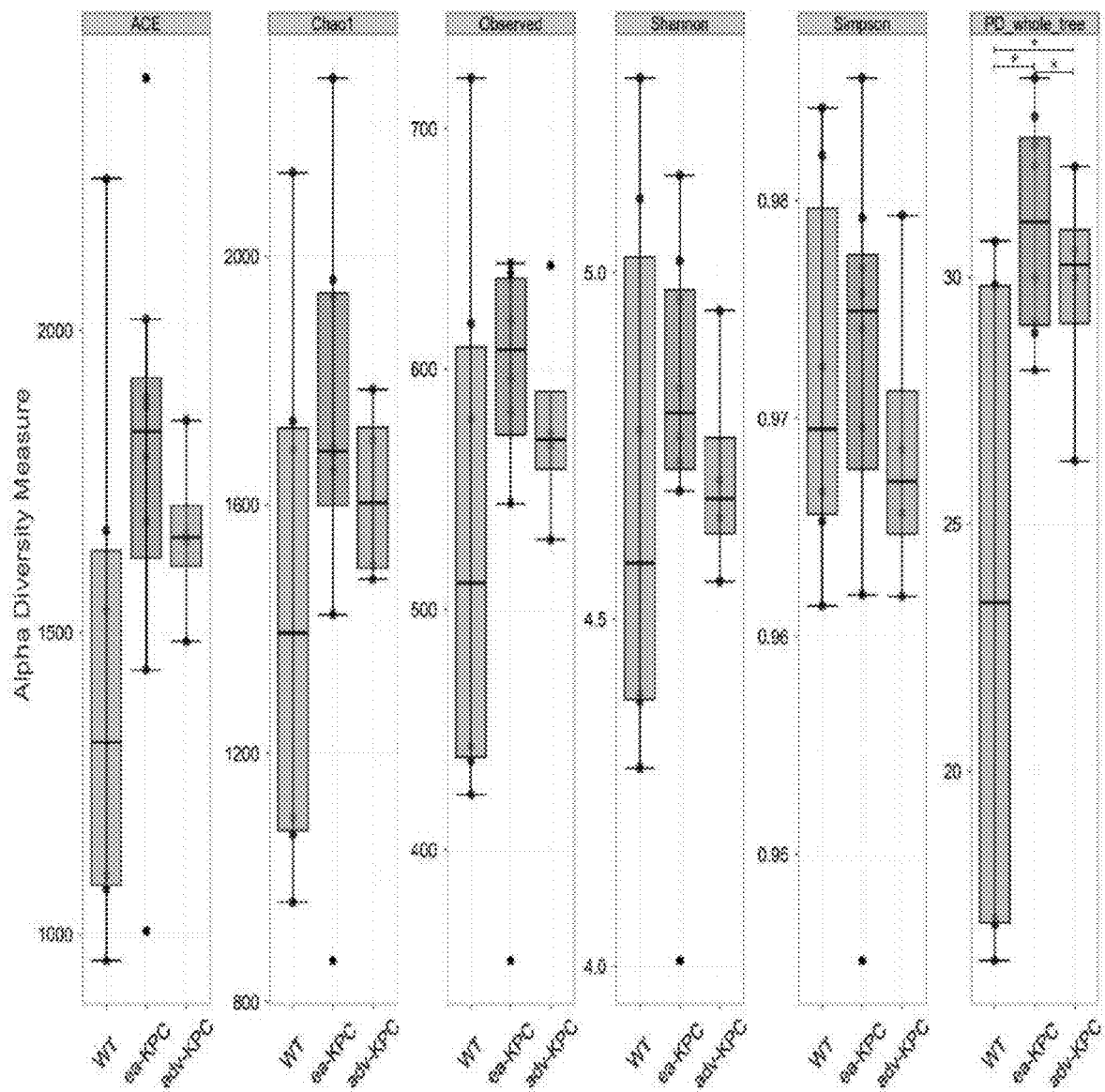
Figure 13A:
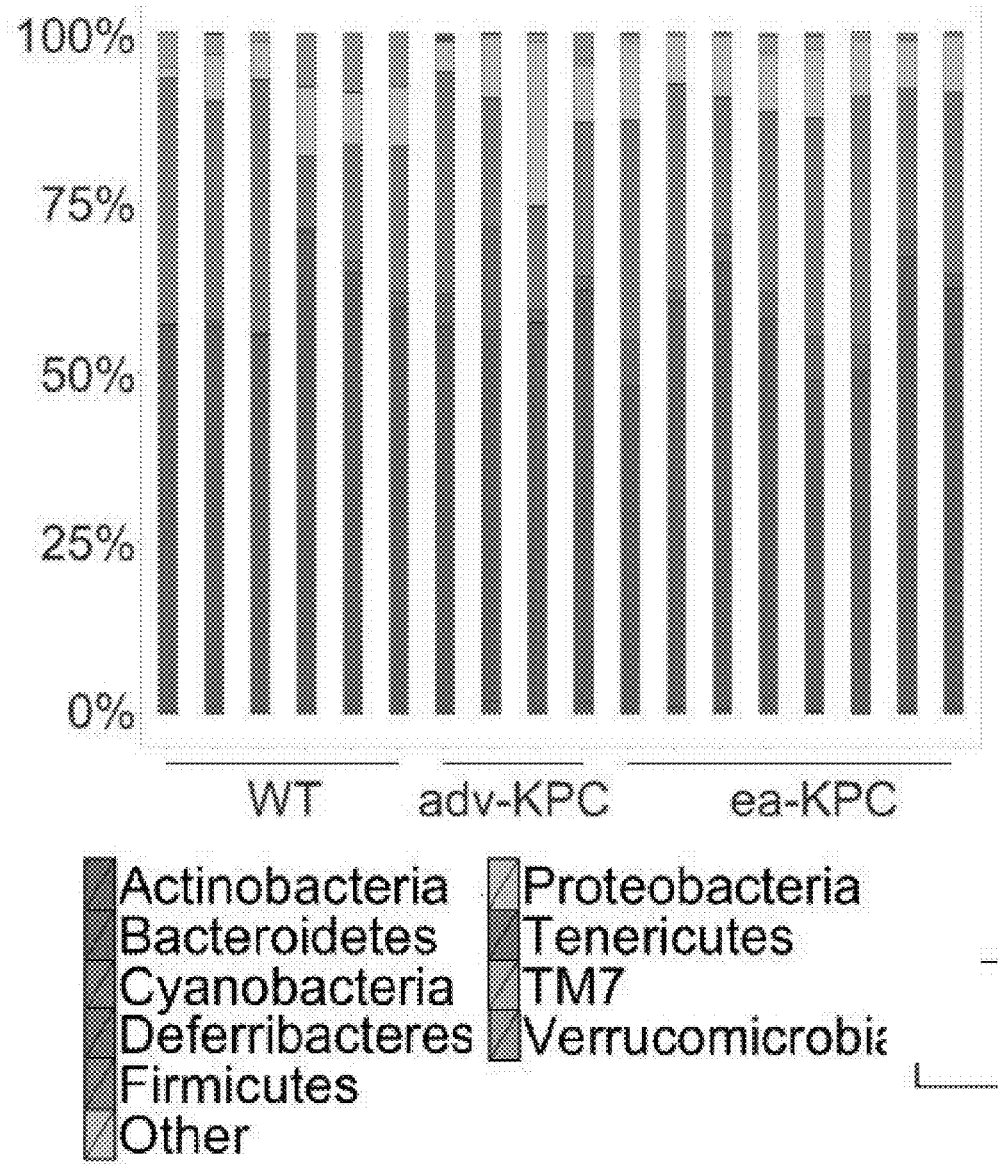
FIGS. 13A-13G. KPC mice with divergent tumor phenotypes harbor distinct gut microbial communities. (13A) Abundances of bacterial phyla in fecal samples of 12 week-old WT (n=6), ea-KPC (n=8), and adv-KPC (n=4) mice. (13B) Heat map showing distribution of top 40 bacterial genera in fecal samples of 12 week-old WT, ea-KPC, and adv-KPC mice. Hierarchical dendrogram linkage clustering is based on composition and abundance of genera in the samples. Average abundances are shown on a log scale. The heat map colors represent the relative percentage of genera from low (blue) to high (orange). (13C-13E) LDA analysis was used to determine differentially enriched genera between WT, ea-KPC, and adv-KPC cohorts. (13F) Relationships between microbial communities for the WT, ea-KPC, and adv-KPC cohorts were analyzed by PCoA. The data indicate three distinct clusters representing each cohort. Variations are shown on the x- and y-axes. Ellipses are at 95% CI. (13G) Bacterial community profiles as monitored by DGGE fingerprints of 16S rDNA fragments from pancreata of WT, ea-KPC, and adv-KPC mice are shown. Analysis of changes in bacterial membership between groups was performed using Dice coefficient and UPGMA dendrogram.
Figure 13B:
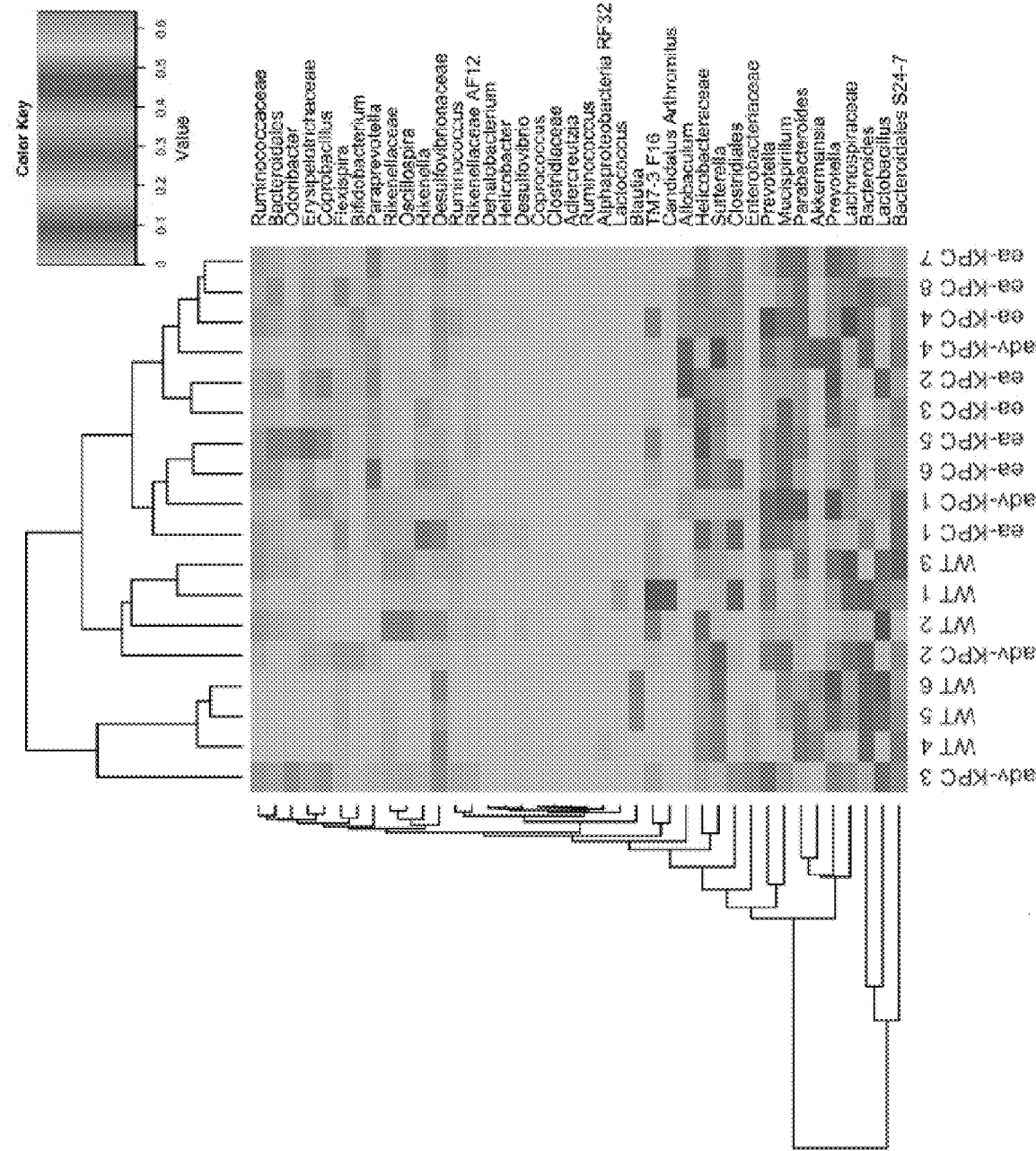
Figure 13C:
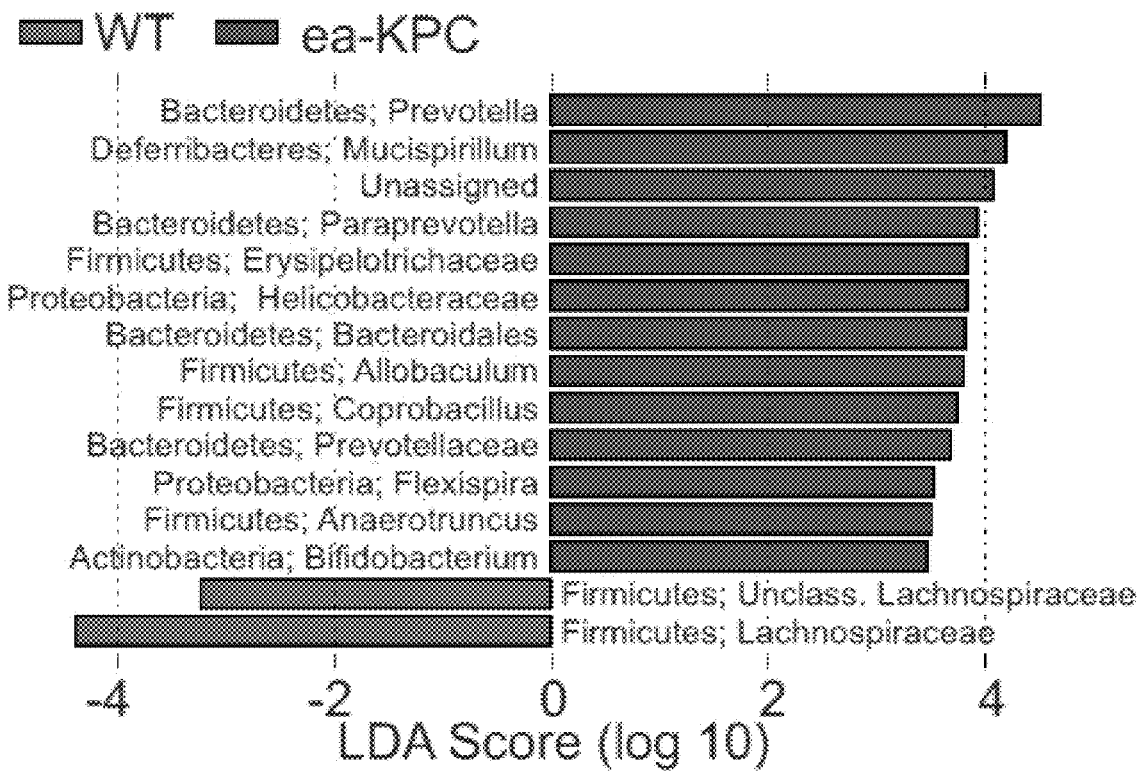
Figure 13D:
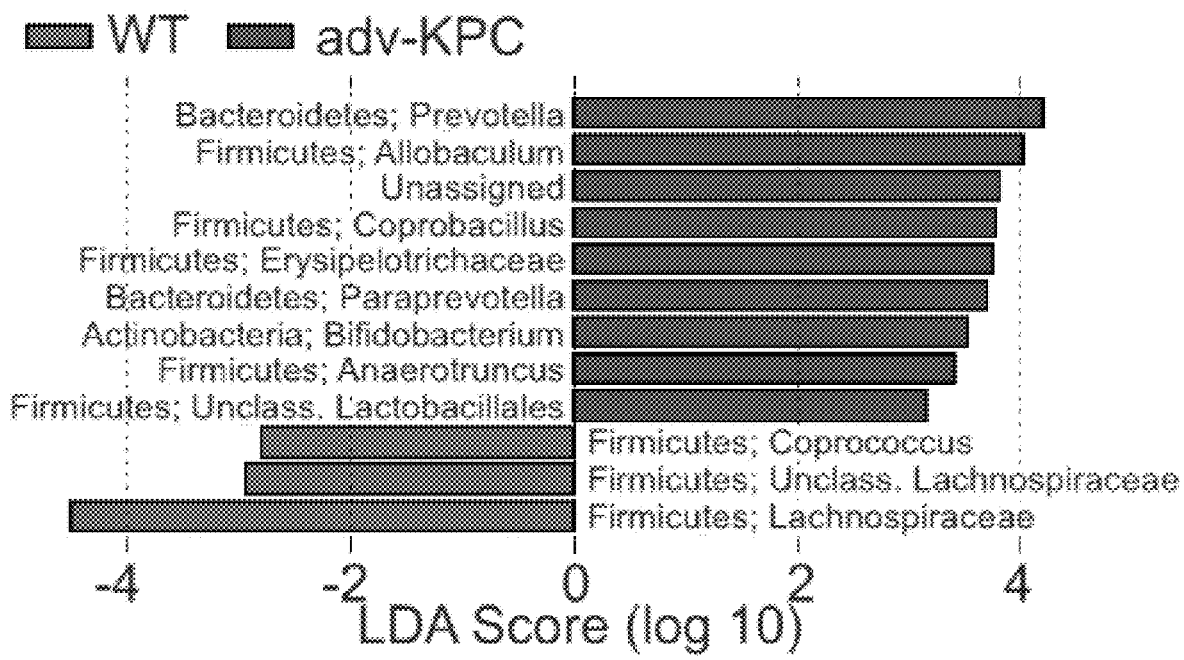
Figure 13E:
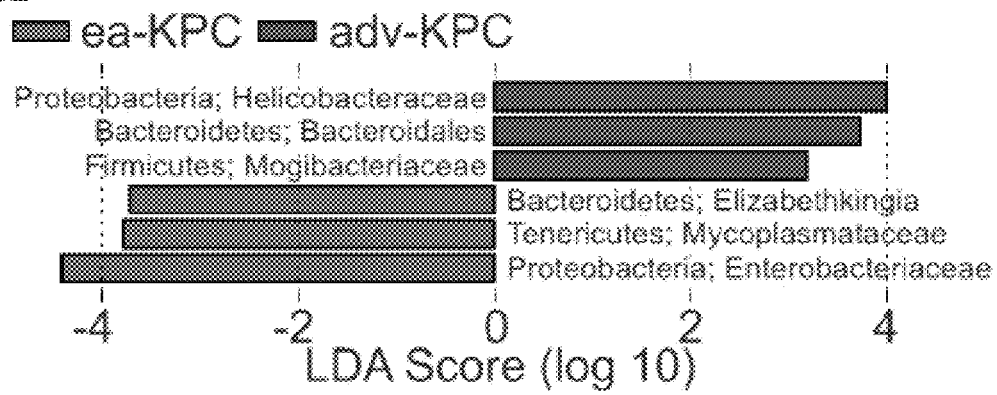
Figure 13F:
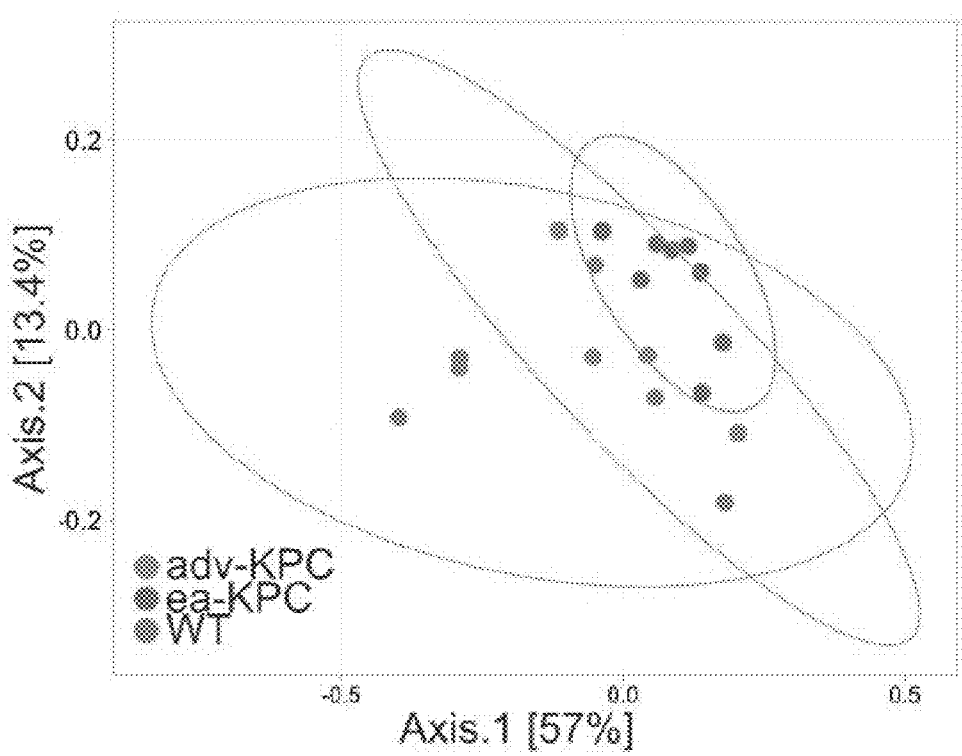
Figure 13G:
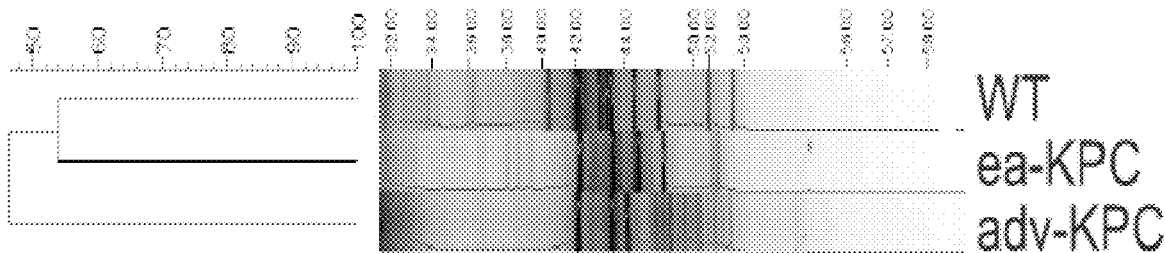

Oncogenesis proceeds at variable rates in hosts with similar genetic risk factors. A quintessential example of this in murine modeling of cancer is the variable tumor phenotype in KPC mice[12]. In order to test whether the primary cause of phenotypic variance in PDA progression in genetically identical mice is the degree of bacterial dysbiosis, the KPC mouse PDA tumors were segregated based on microscopic disease progression and the gut microbial phenotype associated with aggressive PDA (adv-KPC) was compared versus slowly progressive disease (ea-KPC) in 12 week-old KPC mice (FIG. 12A). *Bacteroidetes, Firmicutes*, and *Proteobacteria* were the most abundant bacterial communities in WT, ea-KPC, and adv-KPC cohorts (FIG. 13A). However, *Proteobacteria, Deferribacteres*, and *Actinobacteria* levels were increased in ea-KPC and adv-KPC mice relative to WT mice. Conversely, *Tenericutes* was increased in WT mice. On the genus level, *Bacteroidales* S24-7, *Bacteroides*, and *Lactobacillus* were the most predominant taxa in the three cohorts (FIG. 13B). To identify significantly different bacterial genera between the cohorts, LDA analysis was performed. Similar to the KC model, numerous genera belonging to *Bacteroidetes* and *Firmicutes* and select *Actinobacteria*- and *Deferribacteres*-associated genera (disclosed in the body of the specification and below in Example 2) more prevalent in the ea-KPC and adv-KPC cohorts compared with WT (FIG. 13C, D). When the microbial genera in ea-KPC were contrasted versus adv-KPC mice, it was observed that *Elizabethkingia, Enterobacteriaceae*, and *Mycoplasmataceae*, were significantly overrepresented in ea-KPC, whereas *Helicobacteraceae, Bacteroidales*, and *Mogibacteriaceae* were more prevalent in adv-KPC (FIG. 13E). Global relationships between microbial communities for the WT, ea-KPC, and adv-KPC cohorts were analyzed by PCoA, indicating significant variations between the cohorts and a high degree of similarity within each individual cohort (FIG. 13F). Similarly, comparative analysis of the bacterial fingerprints in pancreata of WT mice, age-matched ea-KPC, and adv-KPC by PCR-denaturing gradient gel electrophoresis (DGGE) indicated that the position and intensity of bands were distinct in each cohort (FIG. 13G). Analysis by Dice coefficient and UPGMA dendrogram (Bionumerics Applied Maths) suggested that intra-pancreatic microbiota in WT and adv-KPC were 40% similar, WT and ea-KPC were 54% similar, and ea-KPC and adv-KPC were 53% similar (FIG. 13G). Accordingly, fecal phylogenetic diversity was significantly different between the 3 murine subsets (FIG. 12B). Collectively, these data suggest that bacterial communities are distinct between early and advanced PDA, despite the host exhibiting identical genotypic risk.

This Example discloses that the gut microbiome exerts potent suppressive influences on the programming of the inflammatory tumor microenvironment in the pancreas. A group of pathogens, even at low abundance within the microbial community, can act as keystone species or signatures that support and shape community structure and membership in a manner that promotes disease pathogenesis[13,14]. The skewed microbial structure and membership in human gut and pancreatic tissues of PDA patients and in mouse models of pancreatic cancer reiterates the possible involvement of mono- or poly-bacterial communities in the initiation and progression of PDA. The data presented herein elucidates the presence of distinct gut microbiotic signatures that are associated with progressive pancreatic oncogenesis and are detectable much earlier than one would expect the disease to be clinically evident. Further, the data presented herein shows that the pancreas harbors its own microbiome that is associated with the aggressiveness of the disease, and that the microbiome is cancer stage-specific. Thus, identification of microbial signatures with tumor specificity, and incorporation in a screening test has tremendous potential for early pre-symptomatic diagnosis and risk assessment. Germ-free or ablative antibiotic treated mice were protected against PDA whereas transfer of gut bacteria from PDA-bearing mice, but not from control mice, reversed the tumor-protection. Bacterial ablation was associated with innate and adaptive immunogenic reprogramming of the PDA tumor microenvironment including a marked reduction in myeloid-derived suppressor cells and immune-suppressive macrophages, increased Th1 differentiation of CD4$^+$ T cells, and expansion and activation of cytotoxic CD8$^+$ T cells. In addition, the data herein shows that gut bacterial ablation and PD-1 blockade offer synergistic efficacy. Finally, modulation of the gut microbiome with the intention to shift it back towards the non-cancerous microbiotic state, and enhancing peritumoral immunity, can be used to reduce the risk of pancreatic cancer or to be used as an adjuvant in immunotherapy and/or chemotherapy.

Methods

Animals and In Vivo Models pC57BL/6 (H-2Kb) mice (WT) were purchased from Jackson Labs (Bar Harbor, Me.). KC mice, which develop spontaneous pancreatic neoplasia by targeted expression of mutant Kras in the pancreas, were a gift of Dafna Bar-Sagi (New York University)[7]. KPC mice, which express mutant intrapancreatic Kras and p53, were a gift from Mark Phillips (New York University)[12]. Animals were housed in a specific pathogen free vivarium and fed standard mouse chow. For orthotopic tumor challenge, mice were administered intrapancreatic injections of FC1242 tumor cells derived from pancreata of KPC mice ($10^5$ cells in Matrigel) and sacrificed at 3 weeks as described[8]. In select experiments, mice were serially treated with a neutralizing α-PD1 mAb (150 µg, i.p., twice weekly, Bioxcell, West Lebanon, N.H.) beginning 3 days prior to orthotopic tumor implantation. For T cell transfer experiments, intra-tumoral T cells were harvested by FACS, mixed with $10^5$ FC1242 cells in a 1:10 ratio, and subcutaneously implanted in the flank of recipient mice. Germ-free KC mice were generated by re-deriving p48$^{Cre}$ and LSL-Kras$^{G12D}$ mice in a germ-free environment at the National Gnotobiotic Rodent Resource Center (Chapel Hill, N.C.), and subsequently crossing the two. Longitudinal cohort studies were conducted to monitor the gut microbial communities throughout experiments by serially collecting fecal pellets from littermate WT and KC or KPC mice.

Antibiotic Treatment, Fecal, and Bacterial Transfer Experiments

To ablate the gut microbiome, 6 week old WT or KC mice were administered an antibiotic cocktail by oral gavage daily for five consecutive days. The oral gavage cocktail contained Vancomycin (50 mg/ml; Sigma, St. Louis, Mo.), Neomycin (100 mg/ml; Sigma), Metronidazole (100 mg/ml; Santa Cruz Biotech, Dallas, Tex.) and Amphotericin (1 mg/ml; MP Biomedicals, Santa Ana, Calif.), as described[15]. Additionally, for the duration of the experiments, mouse drinking water was mixed with Ampicillin (1 mg/ml; Santa Cruz Biotech), Vancomycin (0.5 mg/ml; Sigma), Neomycin (0.5 mg/ml; Sigma), Metronidazole (1 mg/ml; Santa Cruz Biotech) and Amphotericin (0.5 µg/ml; MP Biomedicals). In fecal transfer experiments, six fecal pellets from mice were collected and resuspended in 1 ml of PBS and 200 µl of the fecal slurry was used for orogastric gavage every other day for 2 weeks. To assess bacterial translocation to the pancreas, WT mice were orally gavaged with $2.5 \times 10$ CFU of Enterococcus faecalis that were labelled with 5(6)-Carboxyfluorescein N-hydroxysuccinimidyl ester (CFSE) according to the manufacturer's instructions (Invitrogen/ThermoFisher Scientific, Carlsbad, Calif.). Recipient mice were then serially sacrificed at 3 hour intervals, and their pancreata were harvested. Single cell suspensions of pancreata were prepared and analyzed by flow cytometry for the presence of CFSE-labeled bacteria. All experiments were approved by the NYU School of Medicine Institutional Animal Care and Use Committee (IACUC).

Murine Cellular Isolation, Flow Cytometry, and FACS Sorting

Pancreatic leukocytes were harvested from mouse PDA as described previously[9]. Briefly, pancreata were resected and placed in ice-cold PBS with 1% FBS, Collagenase IV (1 mg/mL; Worthington Biochemical, Lakewood, N.J.) and DNAse I (2 U/mL; Promega, Madison, Wis.). After mincing, tissues were incubated in the same solution at 37° C. for 30 minutes with gentle shaking. Specimens were passed through a 70 m mesh, and centrifuged at 350 g for 5 minutes. Cells were resuspended in ice-cold PBS with 1% FBS. After blocking FcγRIII/II with an anti-CD16/CD32 mAb (eBioscience, San Diego, Calif.), cell labeling was performed by incubating $10^6$ cells with 1 µg of fluorescently conjugated antibodies directed against murine CD44 (IM7), CD206 (C068C2), PD-1 (29F.1A12), CD3 (17A2), CD4 (RM4-5), CD8 (53-6.7), CD45 (30-F11), CD11b (M1/70), Gr1 (RB6-8C5), CD11c (N418), MHC II (M5/114.15.2), IL-10 (JES5-16E3), IFN-γ (XMG1.2), TNFα (MP6-XT22), ICOS (15F9; all Biolegend, San Diego, Calif.), T-bet (eBio4B10), and FoxP3 (FJK-16s; all eBioscience, San Diego, Calif.). Cell preparation for intracellular staining was performed using the FoxP3 Fixation and Permeabilization Solution Kit (eBioscience, San Diego, Calif.). Flow cytometry was performed on the LSR-II (BD Biosciences, Franklin Lakes, N.J.). FACS-sorting was performed on the SY3200 (Sony, Tokyo, Japan). Data were analyzed using FlowJo (Treestar, Ashland, Oreg.).

Histology, Microscopy, and RNA Analysis

For histological analysis, pancreatic specimens were fixed with 10% buffered formalin, dehydrated in ethanol, embedded with paraffin, and stained with H&E or Gomori's Trichrome. The fraction of preserved acinar area was calculated as previously described[10]. Data from control KC mice were previously described[9]. The fraction and number of ducts containing all grades of PanIN lesions were measured by examining 10 high-power fields (HPFs; 40×) per slide. PanINs were graded according to established criteria[16]: In PanIN I ducts, the normal cuboidal pancreatic epithelial cells transition to columnar architecture (PanIN Ia) and gain polyploid morphology (PanIN Ib). PanIN II lesions are associated with loss of polarity. PanIN III lesions, or in-situ carcinoma, show cribriforming, budding off of cells, and luminal necrosis with marked cytological abnormalities, without invasion beyond the basement membrane. Pancreata from 12 week-old KPC mice were segregated based on microscopic assessment by H&E staining of the percentage pancreatic area occupied by invasive cancer. The ea-KPC designated tumors exhibited <25% of pancreatic area occupied by invasive cancer. The adv-KPC tumors exhibited >75% pancreatic area replacement by invasive PDA. Pancreata of mice with 25-75% invasive PDA were excluded from analysis so as to maintain distinctness of the groups. RNA extraction from pancreatic tumors was performed using the RNeasy Mini kit (Qiagen, Germantown, Md.) as per the manufacturer's instructions. For Nanostring analysis, the nCounter mouse inflammation panel was employed using the nCounter Analysis System (both Nanostring, Seattle, Wash.). Pathway analysis was conducted using the GO enrichment analysis tool (geneontology.org/page/go-enrichment-analysis; Gene Ontology Consortium)[17].

Human Sample Collection

Human fecal samples were collected from healthy volunteers and PDA patients by digital rectal examination using sterile gloves. Specimens were stored in TE buffer for 16S pyrosequencing analysis. Patients on antibiotic treatment within the past 3 months, or patients who had received neoadjuvant chemo- or radio-therapy were excluded. Human tissue samples were sterilely collected from patients undergoing surgical resections of the pancreas at NYU Langone Medical Center. Human fecal and tissue specimens were obtained under an approved IRB protocol.

Statistical Considerations for Tumor Size and Immunologic Analyses

Data is presented as mean+/−standard error. Statistical significance was determined by the Student's t test using GraphPad Prism 6 (GraphPad Software, La Jolla, Calif.). P-values<0.05 were considered significant.

Bacterial DNA Extraction and Analysis

Pancreatic tissue samples were suspended in 500 μL of sterile PBS after removing them from a storage buffer; the samples were pretreated by vortexing for 30 seconds followed by sonication and overnight treatment with Proteinase K (2.5 μg/mL) (Epicentre Biotechnologies, an Illumina Company) at 55° C.[18,19]. Total bacterial genomic DNA was purified from human and murine fecal samples and pancreatic tissue samples using MoBio Power fecal kit as per the manufacturer's instructions (MoBio Laboratories Inc., Carlsbad, Calif.). DNA was quantified for concentration and purity by NanoDrop 2000 spectrophotometer (Thermo Scientific, MA, USA) and stored at −20° C. till further analysis. DNA concentration was adjusted to 10 ng/μL for sequencing assays. The pancreatic microbial community was globally characterized using DGGE as we described previously[18]. For high throughput 16S DNA sequencing, the V3-V4 hypervariable region of the 16S gene (16S Amplicon PCR Forward Primer=5' TCGTCGGCAGCGTCA-GATGTGTATAAGAG ACAGCCTACGGG-NGGCWGCAG (SEQ ID NO: 1) 16S Amplicon PCR Reverse Primer=5' GTCTCGTGGGCTCG-GAGATGTGTATAAGAGACAGGAC-TACHVGGGTATCTAATCC (SEQ ID NO: 2)) was amplified from the genomic DNA of the mice and human fecal and pancreatic tissues samples according to the Illumina or 454 16S metagenomics protocol[20,21]. Sequences were analyzed using the quantitative insights into microbial ecology software package (QIIME v. 1.8.0)[22,23]. Initially, the sequences were de-multiplexed and assigned to each sample based on their respective barcodes. Sequences were depleted of barcodes and primers. Short sequences (<200 bp) were removed and sequences with ambiguous base calls and with homopolymer runs exceeding 6 bp were removed. Quality trimming and analysis in QIIME was performed using default parameters. After filtering, Illumina-generated sequences were joined for paired-ends using default parameters of PANDASEQ with a minimum overlap of 25 bp and maximum of 100 bp paired-ends[24]. The UCLUST algorithm was used to cluster similarly filtered sequences into OTUs based on a 97% similarity threshold[25]. The chimeric sequences were removed using ChimeraSlayer[26]. Representative sequences were aligned using PyNAST against Greengenes template alignment (gg_13_8 release), and taxonomy was assigned to the detected OTUs using the basic local alignment search tool (BLAST) reference database and the Greengenes taxonomy-mapping file. The script make_phylogeny.py was used to create phylogenetic trees using the FastTree program[27]

Alpha and Beta Diversity Analysis

The relative abundances of microbial taxa at each taxonomic level, from phylum to species were calculated and compared. OTUs with ≥0.1% abundance in at least one sample were considered for analysis. Alpha diversity in terms of microbial richness estimators (Observed OTUs, Chao1), diversity estimators (Shannon Index, Simpson Index), and phylogenetic diversity (PDs) were calculated using an R-package (RStudio Team (2015). RStudio: Integrated Development for R. RStudio, Inc., Boston, Mass. URL rstudio.com; McMurdie and Holmes (2013) PLoS ONE. 8(4):61217). Alpha-diversity measures were calculated by rarefying the OTUs randomly without replacement to the minimum number of sequences in the sample. Rarefaction was used to normalize the read counts between samples. For alpha diversity metrics, two-sided unpaired Student's t-test or ANOVA were used for analysis. To calculate beta diversity, between-sample diversity, weighted (community structure assessed based on OTU abundance) and unweighted (community structure assessed based on OTU presence/absence) Unifrac metrics were applied to build phylogenetic distance matrices, which were then used to construct hierarchical cluster trees using the unweighted pair group method with arithmetic mean (UPGMA) and represented by PCoA plots. The R packages Phyloseq, Biom, and pheatmap were used for data analysis and plotting. LDA coupled with Lefse were used to identify differential bacterial taxa between cohorts[28].

Example 2. Determining the Species of Gut and Pancreatic Microbiome

Sequence Analysis

For high throughput 16S DNA sequencing, the V3-V4 hypervariable region of the 16S gene was amplified from the genomic DNA of the mice and human fecal and pancreatic tissues samples according to the Illumina or 454 16S metagenomics protocol. Sequences were analyzed using the quantitative insights into microbial ecology software package (QIIME v. 1.8.0). Initially, the sequences were de-multiplexed and assigned to each sample based on their respective barcodes. Sequences were depleted of barcodes and primers. Short sequences (<200 bp) were removed and sequences with ambiguous base calls and with homopolymer runs exceeding 6 bp were removed. Quality trimming and analysis in QIIME was performed using default parameters. After filtering, illumina-generated sequences were joined for paired-ends using default parameters of PANDASEQ with a minimum overlap of 25 bp and maximum of 100 bp paired-ends. The UCLUST algorithm was used to cluster similarly filtered sequences into OTUs based on a 97% similarity threshold. The chimeric sequences were removed using ChimeraSlayer. Representative sequences were aligned using PyNAST against Greengenes template alignment (gg_13_8 release), and taxonomy was assigned to the detected OTUs using the basic local alignment search tool (BLAST) reference database and the Greengenes taxonomy-mapping file. The script make_phylogeny.py was used to create phylogenetic trees using the FastTree program.

Alpha and Beta Diversity Analysis

The relative abundances of microbial taxa at each taxonomic level, from phylum to species were calculated and compared. OTUs with ≥0.1% abundance in at least one sample were considered for analysis. Alpha diversity in terms of microbial richness estimators (Observed OTUs, Chao1), diversity estimators (Shannon Index, Simpson Index), and phylogenetic diversity (PDs) were calculated using an R-package. Alpha-diversity measures were calculated by rarefying the OTUs randomly without replacement to the minimum number of sequences in the sample. Rarefaction was used to normalize the read counts between samples. For alpha diversity metrics, two-sided unpaired Student's t-test or ANOVA were used for analysis. To calculate beta diversity, between-sample diversity, weighted (community structure assessed based on OTU abundance) and unweighted (community structure assessed based on OTU presence/absence). Unifrac metrics were applied to build phylogenetic distance matrices, which were then used to construct hierarchical cluster trees using the unweighted pair group method with arithmetic mean (UPGMA) and represented by PCoA plots.

The R packages Phyloseq, Biom, and pheatmap were used for data analysis and plotting. LDA coupled with Lefse were used to identify differential bacterial taxa between cohorts.

Table 4 lists the bacterial species that were detected in the mouse and human feces as well as human PDA samples.

TABLE 4

Bacterial Species Detected in Pancreatic Cancer Study

| Beneficial | Harmful |
|---|---|
| MOUSE - Fecal | |
| Mouse (KC) Fecal | |
| Candida arthromaticus | Bacteroides acidifaciens |
| Lactobacillus reuteri | Bifidobacterium animalis |
| Ruminococcus gnavus | Bifidobacterium pseudolongum |
| TM7 | Mucispirillium schaedleri |
| | Parabacteroides distantonis |
| Mouse (KPC) Fecal | |
| Akkermansia muciniphila | Ea-KPC |
| Bacteroides eggerthii | Elizabethkingia meningoseptica |
| Bacteroides fragilis | Bacteroides acidifaciens |
| Blautia producta | Mucispirillum schaedleri |
| Candida arthromaticus | Bifidobacterium pseudolongum |
| Parabacteroides distasonis | Adv-KPC |
| | Bacteroides acidifaciens |
| | Bifidobacterium pseudolongum |

TABLE 4-continued

Bacterial Species Detected in Pancreatic Cancer Study

| Beneficial | Harmful |
|---|---|
| | Elizabethkingia meningoseptica |
| | Lactobacillus reuteri |
| | Mucispirillum schaedleri |
| HUMAN- Fecal | |
| Bifidobacterium adoloscentis | Akkermansia muciniphila |
| Eubacterium biforme | Escherichia coli |
| Faecalibacterium prausnitzii | Oxalobacter formigenes |
| Lactobacillus ruminis | Parabacteroides distantonis |
| Prevotella copri | Peptostreptococcus anaerobius |
| Ruminococcus gnavus | Prevotella melaninogenica |
| | Prevotella stercorea |
| | Pyramidobacter piscolens |
| | Rothia mucilaginosa |
| | Viellonella dispar |
| HUMAN- Pancreas | |
| Faecalibacterium prausnitzii | Elizabethkingia meningoseptica |
| Propionibacterium acnes | Pseudomonas |
| Bifidobacterium pseudolongum | Streptococcus anginosus |
| | Veillonella dispar |

REFERENCES

1. Kamada, N., Seo, S.-U., Chen, G. Y. & Nunez, G. Role of the gut microbiota in immunity and inflammatory disease. *Nat Rev Immunol* 13, 321-335 (2013).
2. Schwabe, R. F. & Jobin, C. The microbiome and cancer. Nature reviews. *Cancer* 13, 800-812 (2013).
3. Michaud, D. S., Joshipura, K., Giovannucci, E. & Fuchs, C. S. A Prospective Study of Periodontal Disease and Pancreatic Cancer in US Male Health Professionals. *Journal of the National Cancer Institute* 99, 171-175 (2007).
4. Farrell, J. J., et al. Variations of oral microbiota are associated with pancreatic diseases including pancreatic cancer. *Gut* 61, 582-588 (2012).
5. Mitsuhashi, K., et al. Association of *Fusobacterium* species in pancreatic cancer tissues with molecular features and prognosis. *Oncotarget; Vol* 6, No 9 (2015).
6. Plottel, C. S. & Blaser, M. J. Microbiome and Malignancy. *Cell host & microbe* 10, 324-335 (2011).
7. Hingorani, S. R., et al. Preinvasive and invasive ductal pancreatic cancer and its early detection in the mouse. *Cancer cell* 4, 437-450 (2003).
8. Zambirinis, C. P., et al. TLR9 ligation in pancreatic stellate cells promotes tumorigenesis. *The Journal of Experimental Medicine* 212, 2077-2094 (2015).
9. Seifert, L., et al. The necrosome promotes pancreatic oncogenesis via CXCL1 and Mincle-induced immune suppression. *Nature* 532, 245-249 (2016).
10. Seifert, L., et al. Radiation Therapy Induces Macrophages to Suppress Immune Responses Against Pancreatic Tumors in Mice. *Gastroenterology* (2016).
11. Ino, Y., et al. Immune cell infiltration as an indicator of the immune microenvironment of pancreatic cancer. *British journal of cancer* 108, 914-923 (2013).
12. Hingorani, S. R., et al. Trp53R172H and KrasG12D cooperate to promote chromosomal instability and widely metastatic pancreatic ductal adenocarcinoma in mice. *Cancer cell* 7, 469-483 (2005).
13. Brown, J. H., Whitham, T. G., Morgan Ernest, S. K. & Gehring, C. A. Complex Species Interactions and the Dynamics of Ecological Systems: Long-Term Experiments. *Science* 293, 643-650 (2001).

14. Rutkowski, M. R., et al. Microbially driven TLR5-dependent signaling governs distal malignant progression through tumor-promoting inflammation. *Cancer cell* 27, 27-40 (2015).
15. Reikvam, D. H., et al. Depletion of murine intestinal microbiota: effects on gut mucosa and epithelial gene expression. *PloS one* 6, e17996 (2011).
16. Hruban, R. H., et al. Pancreatic intraepithelial neoplasia: a new nomenclature and classification system for pancreatic duct lesions. *The American journal of surgical pathology* 25, 579-586 (2001).
17. Mi, H., Muruganujan, A., Casagrande, J. T. & Thomas, P. D. Large-scale gene function analysis with the PANTHER classification system. *Nature protocols* 8, 1551-1566 (2013).
18. Pushalkar, S., et al. Comparison of oral microbiota in tumor and non-tumor tissues of patients with oral squamous cell carcinoma. *BMC Microbiology* 12, 144-144 (2012).
19. Pushalkar, S., et al. Oral microbiota and host innate immune response in bisphosphonate-related osteonecrosis of the jaw. *In J Oral Sci* 6, 219-226 (2014).
20. Herlemann, D. P. R., et al. Transitions in bacterial communities along the 2000 km salinity gradient of the Baltic Sea. *ISME J* 5, 1571-1579 (2011).
21. Klindworth, A., et al. Evaluation of general 16S ribosomal RNA gene PCR primers for classical and next-generation sequencing-based diversity studies. *Nucleic Acids Research* 41, e1-e1 (2013).
22. Caporaso, J. G., et al. Ultra-high-throughput microbial community analysis on the Illumina HiSeq and MiSeq platforms. *The ISME Journal* 6, 1621-1624 (2012).
23. Navas-Molina, J. A., et al. Advancing our understanding of the human microbiome using QIIME. *Methods in enzymology* 531, 371-444 (2013).
24. Masella, A. P., Bartram, A. K., Truszkowski, J. M., Brown, D. G. & Neufeld, J. D. PANDAseq: paired-end assembler for illumina sequences. *BMC Bioinformatics* 13, 31-31 (2012).
25. Edgar, R. C. Search and clustering orders of magnitude faster than BLAST. *Bioinformatics* 26, 2460-2461 (2010).
26. Haas, B. J., et al. Chimeric 16S rRNA sequence formation and detection in Sanger and 454-pyrosequenced PCR amplicons. *Genome Research* 21, 494-504 (2011).
27. Price, M. N., Dehal, P. S. & Arkin, A. P. FastTree: Computing Large Minimum Evolution Trees with Profiles instead of a Distance Matrix. *Molecular Biology and Evolution* 26, 1641-1650 (2009).
28. Segata, N., et al. Metagenomic biomarker discovery and explanation. *Genome Biology* 12, R60-R60 (2011).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A method for treating a pancreatic cancer or pancreatic tumor in a subject in need thereof, said method comprising administering to the subject an effective amount of one or more probiotic compositions comprising one or more strains of bacteria from species *Akkermansia muciniphila* and one or more strains of bacteria from species *Lactobacillus reuteri* and further comprising administering a programmed cell death protein 1 (PD-1) inhibitor.

2. The method of claim 1, said method further comprising administering to the subject an effective amount of (i) one or more probiotic compositions comprising one or more strains of bacteria from one or more species selected from the group consisting of *Bifidobacterium pseudolongum, Faecalibacterium prausnitzii,* and *Propionibacterium acnes,* wherein said one or more probiotic compositions are administered to the pancreatic microbiota of the subject, and/or (ii) one or more probiotic compositions comprising one or more strains of bacteria from one or more species selected from the group consisting of *Bacteroides eggerthii, Blautia producta, Candidatus arthromitus, Eubacterium biforme, Lactobacillus ruminis,* and TM7, wherein said one or more compositions are administered to the gastrointestinal (GI) microbiota of the subject, and/or (iii) one or more compounds and/or compositions which inhibit growth and/or activity of one or more strains of bacteria from one or more species selected from the group consisting of *Bacteroides acidifaciens, Bifidobacterium pseudolongum, Elizabethkingia meningoseptica, Mucispirillum schaedleri, Streptococcus anginosus,* and *Veillonella dispar* in the pancreatic microbiota of the subject, and/or (iv) one or more compounds and/or compositions which inhibit growth and/or activity of one or more strains of bacteria from one or more species selected from the group consisting of *Bacteroides acidifaciens, Bifidobacterium animalis, Bifidobacterium pseudolongum, Desulfovibrio* D168, *Elizabethkingia meningoseptica, Escherichia coli, Mucispirilhum schaedleri, Oxalobacter formigenes, Parabacteroides distasoni, Peptostreptococcus anaerobius, Prevotella melaninogenica, Prevotella stercorea, Pyramidobacter piscolens, Rothia mucilaginosa, Streptococcus anginosus,* and *Veillonella dispar* in the gastrointestinal (GI) microbiota of the subject.

3. The method of claim 1, wherein said one or more probiotic composition(s) comprise live bacterial cells, spores, and/or conditionally lethal bacterial cells of *Akkermansia muciniphila* and *Lactobacillus reuteri.*

4. The method of claim 1, said method further comprising administering to the subject an effective amount of one or more compounds and/or compositions, wherein said compounds and/or compositions (i) inhibit growth and/or activity of one or more strains of bacteria from one or more species selected from the group consisting of *Bacteroides acidifaciens, Bifidobacterium pseudolongum, Elizabethkingia meningoseptica, Mucispirillum schaedleri Streptococcus anginosus,* and *Veillonella dispar* in the pancreatic microbiota of the subject, and/or (ii) inhibit growth and/or activity of one or more strains of bacteria from one or more species selected from the group consisting of *Bacteroides acidifaciens, Bifidobacterium animalis, Bifidobacterium pseudolongum, Desulfovibrio* D168, *Elizabethkingia meningoseptica, Escherichia coli, Mucispirillium schaedleri, Oxalobacter formigenes, Parabacteroides distasoni, Peptostreptococcus anaerobius, Prevotella melaninogenica, Prevotella stercorea, Pyramidobacter piscolens, Rothia mucilaginosa, Streptococcus anginosus,* and *Veillonella dispar* in the gastrointestinal (GI) microbiota of the subject.

5. The method of claim 4, wherein the one or more compounds and/or compositions comprise an antibiotic or natural product that inhibits microbial growth.

6. The method of claim 1, wherein said one or more probiotic composition(s) are administered by a route selected from the group consisting of oral, rectal, sublingual, intravenous, and via naso/oro-gastric gavage.

7. The method of claim 1, further comprising administering an additional cancer therapy.

8. The method of claim 7, wherein the additional cancer therapy is selected from the group consisting of surgery, radiotherapy, chemotherapy, immunotherapy, and any combinations thereof.

9. The method of claim 1, wherein said one or more probiotic compositions are administered directly to the pancreatic microbiota.

10. The method of claim 1, wherein the pancreatic cancer is pancreatic ductal adenocarcinoma (PDA).

11. The method of claim 1, wherein the subject is human.

12. The method of claim 1, said method further comprising administering to the subject an effective amount of one or more probiotic compositions comprising one or more strains of bacteria from one or more species selected from the group consisting of *Bifidobacterium pseudolongum, Faecalibacterium prausnitzii, Propionibacterium acnes, Bacteroides eggerthii, Blautia producta, Candidatus arthromitus, Eubacterium biforme, Faecalibacterium prausnitzii, Lactobacillus ruminis,* and TM7.

13. The method of claim 1, wherein the method comprises administering to the subject an effective amount of one or more antibiotics and/or natural products that inhibits microbial growth, prior to administering to the subject said one or more probiotic compositions.

14. The method of claim 1, wherein the method does not comprise administering to the subject a prebiotic.

* * * * *

UNITED STATES PATENT AND TRADEMARK OFFICE
CERTIFICATE OF CORRECTION

PATENT NO. : 11,723,935 B2
APPLICATION NO. : 16/484080
DATED : August 15, 2023
INVENTOR(S) : George Miller et al.

It is certified that error appears in the above-identified patent and that said Letters Patent is hereby corrected as shown below:

In the Specification

At Column 1, beginning in Line 18 and ending in Line 23 please replace:
"This invention was made with government support under Grant Nos. CA206105, CA168611, CA155649, OD10995, and DK034987 awarded by the National Institute of Health and a Department of Defense Peer Reviewed Medical Research Program Grant. The government has certain rights in the invention."
With:
--This invention was made with government support under CA168611, P30 DK034987, CA155649, P40 OD010995, and CA206105 awarded by the National Institutes of Health. The government has certain rights in the invention.--

Signed and Sealed this
First Day of April, 2025

Coke Morgan Stewart
*Acting Director of the United States Patent and Trademark Office*

SEQUENCE LISTING

```
<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (42)..(42)
<223> OTHER INFORMATION: a, c, t, g, unknown or other

<400> SEQUENCE: 1
tcgtcggcag cgtcagatgt gtataagaga cagcctacgg gnggcwgcag              50

<210> SEQ ID NO 2
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtctcgtggg ctcggagatg tgtataagag acaggactac hvgggtatct aatcc          55
```